United States Patent

Kalindjian et al.

[11] Patent Number: 5,919,829
[45] Date of Patent: Jul. 6, 1999

[54] GASTRIN AND CCK RECEPTOR LIGANDS

[75] Inventors: Sarkis Barret Kalindjian, Banstead; Katherine Isobel Mary Steel, Beckenham; Michael John Pether, Oppington; Jonathan Michael Richard Davies, Beckenham; Caroline Minli Rachel Low, Croydon; Martin Lyn Hudson, Brighton; Ildiko Maria Buck, London; Iain Mair McDonald, Paddock Wood; David John Dunstone; Matthew John Tozer, both of London, all of United Kingdom

[73] Assignee: James Black Foundation Limited, London, United Kingdom

[21] Appl. No.: 09/064,849

[22] Filed: Apr. 23, 1998

Related U.S. Application Data

[62] Division of application No. 08/583,008, filed as application No. PCT/GB94/01741, Aug. 9, 1994, Pat. No. 5,795,907.

[30] Foreign Application Priority Data

Aug. 10, 1993 [GB] United Kingdom .................. 9316608
May 27, 1994 [GB] United Kingdom .................. 9410688

[51] Int. Cl.$^6$ ......................... A61K 31/40; A61K 31/415; C07D 415/54; C07D 453/02
[52] U.S. Cl. ......................... 514/682; 514/252; 514/255; 514/259; 514/315; 514/231.2; 514/311; 514/359; 544/235; 544/405; 544/238; 544/370; 544/106; 544/373; 546/314; 548/214; 548/146; 548/215; 548/240; 548/300.1; 549/401; 549/402; 549/429
[58] Field of Search ................................ 514/682, 252, 514/255, 259, 231.2, 311, 359; 544/235, 405, 238, 370, 106, 373; 548/214, 146, 215, 240, 300; 549/401, 402, 429

[56] References Cited

U.S. PATENT DOCUMENTS 5,795,907  8/1998  Kalindjian et al. .................. 514/397

FOREIGN PATENT DOCUMENTS

93/20099  10/1993  WIPO .

Primary Examiner—Richard L. Raymond
Assistant Examiner—Tavanram K. Sripada
Attorney, Agent, or Firm—Foley & Lardner

[57] ABSTRACT

Compounds of formula (Ia), (Ib), or (Ic), wherein A represents a group having two fused rings, or a group of formula (Id), $R^1_{(m)}$ represents up to 6 substituents, K represents —O—, —S—, —CH$_2$—, —N(R$^2$)— or —N(COR$^2$)—, in which R$^2$ is H or C$_1$ to C$_3$ alkyl, W is a carbonyl, sulfonyl or sulfinyl group, provided that at least one of W and X contains carbonyl, Y and Z are as given in the description, and their pharmaceutically acceptable salts are ligands at CCK and/or gastrin receptors.

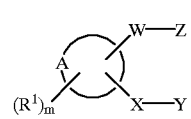

(Ia)

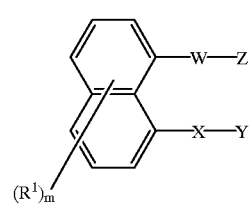

(Ib)

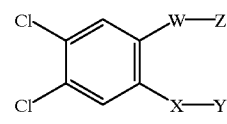

(Ic)

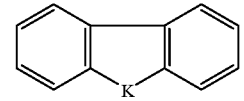

(Id)

11 Claims, No Drawings

GASTRIN AND CCK RECEPTOR LIGANDS

This application is a divisional of application Ser. No. 08/583,008, filed Mar. 18, 1996 which is a national stage of PCT/GB94/01741 filed Aug. 9, 1994 now patented as U.S. Pat. No. 5,795,907.

This invention relates to gastrin and CCK receptor ligands. The invention also relates to methods for preparing such ligands and to compounds which are useful as intermediates in such methods.

Gastrin and the CCK's are structurally-related neuropeptides which exist in gastrointestinal tissue and in the CNS (see Mutt V., *Gastrointestinal Hormones*, Glass G. B. J., ed., Raven Press, N.Y., p 169 and Nisson G., ibid, p. 127).

Gastrin is one of the three primary stimulants of gastric acid secretion. Several forms of gastrin are found 15 including 34-, 17-, and 14-amino acid species with the minimum active fragment being the C-terminal tetrapeptide (TrpMetAspPhe-NH$_2$) which is reported in the literature to have full pharmacological activity (see Tracey H. J. and Gregory R. A., Nature (London), 1964, 204, 935). Much effort has been devoted to the synthesis of analogues of this tetrapeptide (and the N-protected derivative Boc-TrpMetAspPhe-NH$_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal motility, gall bladder contraction, pancreatic enzyme secretion, and are known to have a trophic action on the pancreas. They also inhibit gastric emptying and have various effects in the CNS.

Compounds which bind to cholecystokinin and/or gastrin receptors are important because of their potential pharmaceutical use as antagonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lowered gastrin activity is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa, and the treatment of pancreatic inflammation, biliary tract disease and various psychiatric disorders. Other possible uses are in the potentiation of opiate (e.g. morphine) analgesia, and in the treatment of cancers, especially of the pancreas. Moreover, ligands for cholecystokinin receptors in the brain (so-called CCK$_B$ receptors) have been claimed to possess anxiolytic activity.

According to the present invention, there are provided compounds of the formula

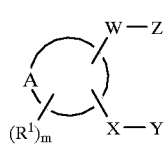

(Ia)

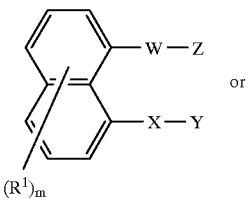

(Ib)

or

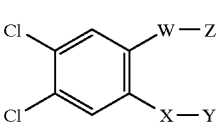

(Ic)

wherein A represents a bicyclic group (meaning a group having two fused rings, in which the atoms which are common to the two rings are joined by a single or multiple bond), W and X replacing hydrogen on adjacent atoms (most usually adjacent carbon atoms), or A is a group of the formula

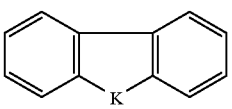

(Id)

in which W and X replace hydrogen on adjacent carbon atoms, m is from 0 to 6, provided that m is not more than 2 unless $R^1$ is exclusively halo, $R^1$ is halo, amino, amidino, nitro, cyano, hydroxy, sulphamoyl, hydroxysulphonyl, carboxy, esterified carboxy, amidated carboxy, tetrazolyl, $C_1$ to $C_8$ alkyl (particularly $C_1$ to $C_6$ alkyl), aryl, substituted aryl, $C_1$ to $C_6$ hydroxyalkyl, $C_1$ to $C_6$ haloalkyl, $C_1$ to $C_6$ alkoxy, $C_1$ to $C_6$ alkylcarboxyamino, HON=C—, $R^{27}$—SO$_2$—NH—, $R^{27}$—SO—NH—CO—, $R^{27}$—CO—, $R^{27}$—CO—NH—, $R^{27}$—CO—NH—SO$_2$—, $R^{27}$—CO—NH—SO— or $R^{26}$—NH—SO$_2$—, wherein $R^{27}$ is H (except when $R^{27}$ is attached to a sulphur atom), $C_1$ to $C_6$ alkyl, $C_1$ to $C_6$ haloalkyl, aryl or substituted aryl, and $R^{28}$ is H, $C_1$ to $C_6$ alkyl, $C_1$ to $C_6$ haloalkyl, aryl, substituted aryl, —OH or —CN (each $R^1$ group, when m is 2 or more, being independently selected from the foregoing), K represents —O—, —S—, —CH$_2$—, —N(R$^2$)— or —N(COR$^2$)—, in which $R^2$ is H or $C_1$ to $C_3$ alkyl, W is a carbonyl, sulphonyl or sulphinyl group, and X is a carbonyl, sulphonyl or sulphinyl group, provided that at least one of W and X contains carbonyl, Y is $R^3$—N(R$^4$)— or $R^3$—O— (wherein $R^3$ is H or $C_1$ to $C_{15}$ hydrocarbyl, one or more hydrogen atoms of the hydrocarbyl moiety optionally being replaced by halogen atoms, and up to two carbon atoms of the hydrocarbyl moiety optionally being replaced by a nitrogen, oxygen or sulphur atom, $R^3$ is $C_6$ to $C_{15}$ hydrocarbyl, one or more hydrogen atoms of the hydrocarbyl moiety optionally being replaced by halogen atoms, and up to two carbon atoms of the hydrocarbyl moiety optionally being replaced by a nitrogen, oxygen or sulphur atom, and $R^4$ is H, $C_1$ to $C_3$ alkyl, carboxymethyl or esterified carboxymethyl), provided that Y does not contain a —O—O— group, and Z is selected from

   i)

wherein $R^5$ is H, $C_1$ to $C_5$ alkyl, phenyl, substituted phenyl, benzyl or substituted benzyl;

ii)

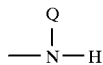

wherein Q is H, $C_1$ to $C_5$ hydrocarbyl, or —$R^6$—U, wherein $R^6$ is a bond or $C_1$ to $C_5$ (eg. $C_1$ to $C_3$) alkylene and U is aryl, substituted aryl, heterocyclic, substituted heterocyclic or cycloalkyl (preferably cyclohexyl or cycloheptyl), iii)

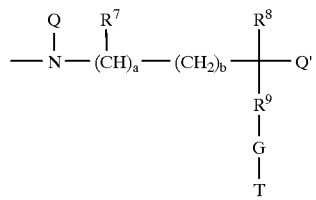

wherein a is 0 or 1 and b is from 0 to 3,
$R^7$ is H or methyl,
$R^8$ is H or methyl; or $R^8$ is $CH_2=$ and Q' is absent; or $R^7$ and $R^8$ are linked to form a 3- to 7-membered ring,
$R^9$ is a bond or $C_1$ to $C_5$ hydrocarbylene,
G is a bond, —CHOH— or —C(O)—
Q' is as recited above for Q or —$R^6$—(C(O))$_d$—L—(C(O))$_e$—$R^5$ (wherein $R^5$ and $R^6$ are as defined above, L is O, S or —N($R^{10}$)—, in which $R^{10}$ is as defined above for $R^4$, and d and e are 0 or 1, provided that d+e<2); or Q' and $R^8$, together with the carbon atom to which they are attached, form a 3- to 7-membered ring,
Q is as defined above; or Q and $R^8$ together form a group of the formula —$(CH_2)_f$—V—$(CH_2)_g$— wherein V is —S—, —S(O)—, —S(O)$_2$—, —$CH_2$—, —CHOH— or —C(O)—, f is from 0 to 2 and g is from 0 to 3; or, when Q' is —$R^6$—U and U is an aromatic group, Q may additionally represent a methylene link to U, which link is ortho to the $R^6$ link to U,
T is H, cyano, $C_1$ to $C_4$ alkyl, —$CH_2OH$, carboxy, esterified carboxy, amidated carboxy or tetrazolyl; or iv)

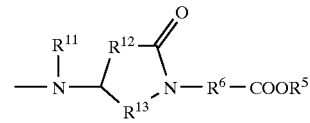

wherein $R^5$ and $R^6$ are as defined above, $R^{11}$ is as defined above for $R^4$, and $R^{12}$ and $R^{13}$ are independently a bond or $C_1$ to $C_3$ alkylene, provided that $R^{12}$ and $R^{13}$ together provide from 2 to 4 carbon atoms in the ring,
and pharmaceutically acceptable salts thereof.

Certain compounds of the invention exist in various regioisomeric, enantiomeric, tautomeric and diastereomeric forms. It will be understood that the invention comprehends the different regioisomers, enantiomers, tautomers and diastereomers in isolation from each other, as well as mixtures.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups, A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl). The term "aryl" is used herein to refer to aromatic carbocyclic groups, including those mentioned above.

A "heterocyclic" group comprises one or more closed chains or rings which have at least one atom other than carbon in the closed chain or ring. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

The term "halogen", as used herein, refers to any of fluorine, chlorine, bromine and iodine. Most usually, however, halogen substituents in the compounds of the invention are chlorine or fluorine substituents.

When reference is made herein to a "substituted" aromatic group, the substituents will generally be from 1 to 3 in number (and more usually 1 or 2 in number), and generally selected from the groups recited above for $R^1$. However, halo substituents may be up to 5 in number.

Preferably, m is 0. However, when m is not 0, $R^1$ is preferably selected from halo, amino, nitro, cyano, sulphamoyl, sulphonyl, trifluoromethyl, $C_1$ to $C_3$ alkyl, hydroxy, $C_1$ to $C_3$ hydroxyalkyl, $C_1$ to $C_3$ alkoxy, $C_1$ to $C_3$ alkylcarboxyamino, carboxy, esterified carboxy, amidated carboxy and tetrazolyl, and more preferably from halo, amino, nitro, cyano, sulphamoyl, $C_1$ to $C_3$ alkyl and $C_1$ to $C_3$ alkoxy. As mentioned above, when m is 2 or more, each $R^1$ group is independent of the others. For example, the compounds of the invention may include two different $R^1$ groups.

An "esterified" carboxy group, as the term is used herein, is preferably of the form —$COOR^{14}$, wherein $R^{14}$ is $C_1$ to $C_5$ alkyl, phenyl, substituted phenyl, benzyl, substituted benzyl, indanyl, or one of the following:

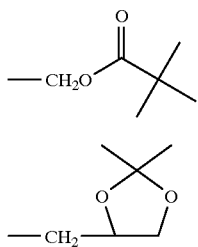

Most commonly, $R^{14}$ is $C_1$ to $C_5$ alkyl, benzyl or substituted benzyl, and particularly $C_1$ to $C_5$ alkyl.

"Amidated" carboxy groups include alkoxyamido groups (particularly $C_1$ to $C_6$ alkoxyamido groups), but are more usually of the form —$CONR^{15}R^{16}$ wherein $R^{15}$ is H, $C_1$ to $C_5$ alkyl, phenyl, substituted phenyl, benzyl or substituted benzyl, and $R^{16}$ is —OH or one of the groups just recited for $R^{15}$.

In the case of the group T, preferred amidated carboxy groups take the form —$CONR^{15}R^{16}$ (wherein $R^{15}$ and $R^{16}$ are as defined above) or

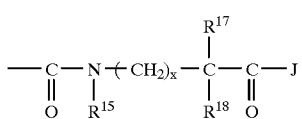

wherein $R^{15}$ is as defined above, $R^{17}$ and $R^{18}$ are independently H or methyl, or $R^{17}$ and $R^{18}$ (together with the carbon atom to which they are attached) form a 3- to 7-membered carbocyclic group, J is —OH, —O—$R^{14}$ or —$NHR^{16}$, wherein $R^{14}$ and $R^{16}$ are as defined above, and x is 0 to 3.

When $R^7$ and $R^8$ are linked to form a ring, such ring will generally be saturated, and usually also carbocyclic. Similarly, when Q' and $R^8$ are linked to form a ring, this will also usually be saturated and carbocyclic.

Exemplary carbocyclic and heterocyclic groups which may form the group U include:

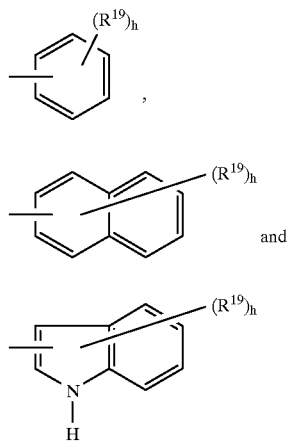

wherein $R^{19}$ is as defined above for $R^1$, and h is from 0 to 3 (or up to 5 when $R^{19}$ is exclusively halo), and

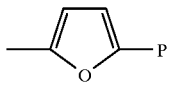

wherein P is H or —$COOR^{20}$, in which $R^{20}$ is as defined above for $R^{15}$.

Z is preferably —$NH_2$, —O—$R^5$ or

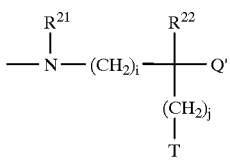

wherein i is from 0 to 4, j is from 0 to 3, $R^{21}$ and $R^{22}$ are independently H or methyl, or $R^{21}$ and $R^{22}$ together form a group of the formula —$(CH_2)_k$—V'—$CH_2$— (wherein V' is —$CH_2$—, —CHOH— or —C(O)—, and k is 0 to 2). Most commonly, i is 0 or 1 and j is 0 to 2.

When W is sulphinyl, Y is preferably $R^3$—NH—.

Preferably, $R^3$ is $C_6$ to $C_8$ straight or branched chain alkyl, or $R^{23}$—$(CH_2)_p$—, wherein $R^{23}$ is selected from phenyl, 1-naphthyl, 2-naphthyl, indolyl, norbornyl, adamantyl, cyclohexyl or cycloheptyl, and p is from 0 to 3.

Favoured bicyclic groups to form A in formula (Ia) above include

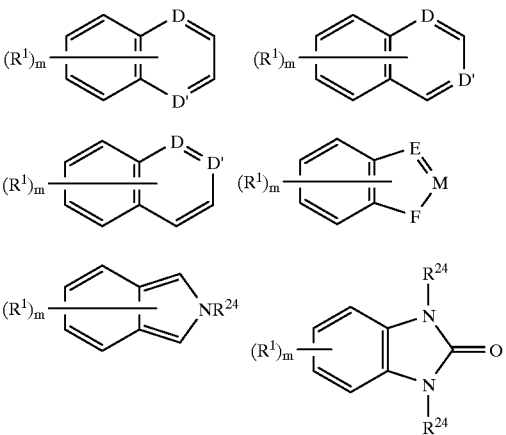

and

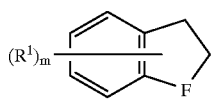

wherein $R^{24}$ is H, $C_1$ to $C_8$ alkyl or $R^{25}$—CO—

$R^{25}$ is H or $C_1$ to $C_8$ (eg. $C_1$ to $C_3$) alkyl

D and D' are independently —CH=, —N= or —$SR^{26}$= ($R^{26}$ being H or $C_1$ to $C_3$ alkyl, or $R^{26}$ is absent and the sulphur atom is positively charged)

E is —CH= or —N=

M is —$CR^{24}$=, —N= or —$C(NR^{24}R^{25})$= (wherein $R^{24}$ and $R^{25}$ are as defined above), and F is —O—, —S—, —$CH_2$— or —$NR^{24}$— (wherein $R^{24}$ is as defined above).

Preferably, the compounds of the invention are of the formula:

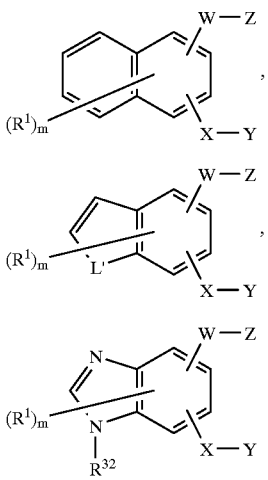

(wherein w and x are attached to adjacent carbon atoms; $R^{32}$ is H, $C_1$ to $C_3$ alkyl or $C_1$ to $C_3$ alkylcarboxy; and L' is $-NR^{32}-$, $-O-$ or $-S-$),

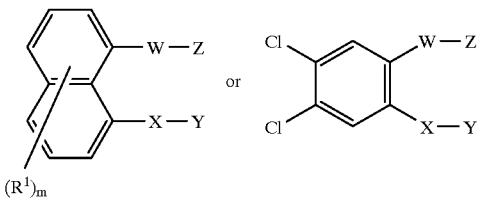

Also preferred are compounds in which

—X—Y is —$CONR^3R^4$ ($R^3$ and $R^1$ being as defined above), and

—W—Z is

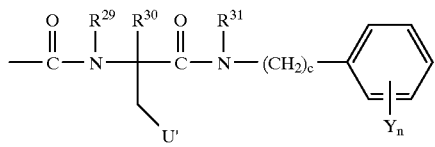

(wherein $R^{29}$, $R^{30}$ and $R^{31}$ are independently H or $C_1$ to $C_3$ alkyl; U' is an (optionally substituted) aromatic group; n is 1 or 2; Y is —$CO_2H$, tetrazolyl, esterified carboxy, amidated carboxy, $R^{27}-SO_2-NH-$, $R^{27}-SO_2-NH-CO-$, $R^{27}-CO-$, $R^{27}-CO-NH-$, $R^{27}-CO-NH-SO_2-$, $R^{27}-CO-NH-SO-$ or $R^{28}-NH-SO_2-$ ($R^{27}$ and $R^{28}$ being as defined above), each Y being independently selected from the foregoing when n is 2; and c is from 0 to 2).

Compounds according to the present invention in which W is a carbonyl group, X is carbonyl or sulphonyl, and Z is OH may conveniently be made by reacting a compound of the formula YH (ie. either an alcohol or an amine) with a compound of the formula

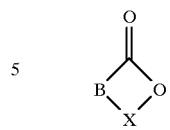
(II)

wherein B represents

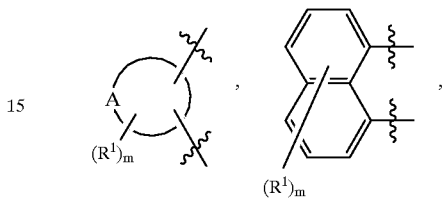

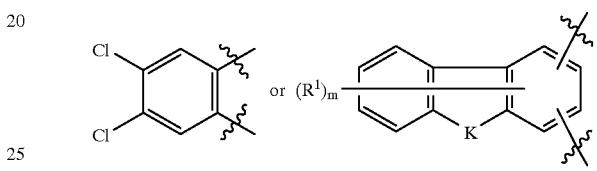

If YH is an amine, the reaction is suitably carried out in a solvent such as THF in the presence of a base such as DMAP. If YH is an alcohol, the reaction may be conducted in pyridine at elevated temperature.

Compounds in which Z is other than OH may of course be made from the acid compound

(III)

by conventional esterification or amidation reactions on suitably protected derivatives. Suitable amidation methods are described in detail in "The Peptides, Vol. 1", Gross and Meinenhofer, Eds., Academic Press, N.Y., 1979. These include the carbodiimide method (using, for example, 1,3-dicyclohexylcarbodiimide [DCC] or 1-(3-dimethylaminopropyl)-3-ethylcarbodiimide hydrochloride [EDCI], and optionally an additive such as 1-hydroxybenzotriazole [HOBT] to prevent racemization), the azide method, the mixed anhydride method, the symmetrical anhydride method, the acid chloride method, the acid bromide method, the use of bis (2-oxo-3-oxazolidinyl) phosphinic chloride [BOP-Cl], the use of PyBOP or PyBrOP, the use of the isopropenylsuccinimido carbonate method and the active ester method (using, for example, N-hydroxysuccinimide esters, 4-nitrophenyl esters or 2,4,5-trichlorophenol esters). The coupling reactions are generally conducted under an inert atmosphere, such as an atmosphere of nitrogen or argon. Suitable solvents for the reactants include methylene chloride, tetrahydrofuran [THF], dimethoxyethane [DME] and dimethylformamide [DMF].

Bisamides according to the present invention may alternatively be prepared by reacting a compound of formula (II) with a suitably protected derivative of ZH, followed by conventional amidation as described above.

An analogous procedure may also be used as the basis for preparing the compounds of the invention in which W is sulphonyl and Y is $R^3$—O—, as depicted in reaction scheme A below:

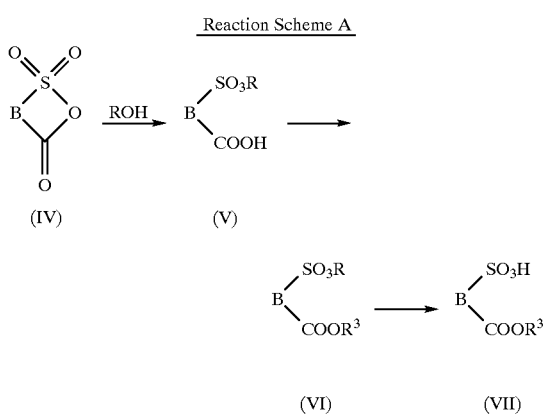

In this case, the mixed anhydride (IV) is opened with an alcohol such as benzyl alcohol (represented as ROH), so that the product is the corresponding sulphonyl ester (V). The free carboxylic acid group of this sulphonyl ester may then be esterified by conventional methods, followed by hydrogenolysis of the product (VI) to yield the desired sulphonic acid carboxylic ester (VII).

The compounds of the invention in which W is sulphonyl and Y is $R^3$—NH— may be prepared by analogous means, in which compound (V) is amidated (rather than esterified) prior to hydrogenolysis. Alternatively, a process such as is depicted in reaction scheme B may be employed:

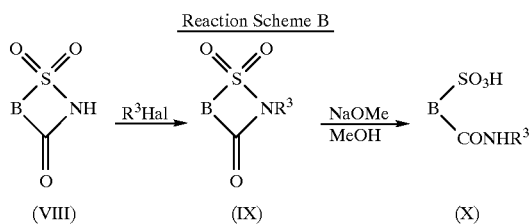

In this scheme, compound (VIII) is reacted with a compound of the formula $R^3$—Hal (wherein Hal represents a halogen atom) to form compound (IX). The N-containing ring may then be opened using an alkoxide (eg. sodium methoxide in methanol) to produce the target compound (X).

The invention therefore also provides a method of making compounds wherein W is sulphonyl and Y is $R^3$—NH—, said method comprising the step of reacting a compound of formula (VIII) with a compound of the formula $R^3$—Hal, and then reacting the product with an alkoxide.

Compounds of the invention wherein W or X is a sulphoxide group may conveniently be prepared by the route shown in reaction scheme C:

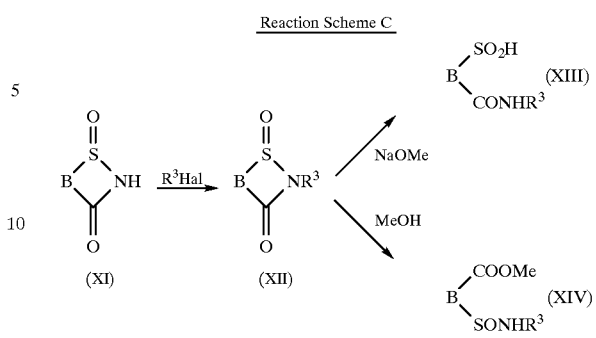

Compound (XII) can then be opened both ways to give on the one hand the sulphinamide acid alkyl ester (XIII), and on the other the sulphinic acid amide (XIV). The free sulphinamide acid can of course be obtained from the alkyl ester (XIII) by conventional methods.

Accordingly, the invention also provides a method of making compounds wherein W or X is sulphoxide, said method comprising the step of reacting a compound of formula (XI) with a compound of the formula $R^3$—Hal, and then reacting the product with an alkoxide.

While reaction schemes B and C above lead to the free sulphonic or sulphinic acid compounds, it will be appreciated that the corresponding ester or amide derivatives can be prepared from the free acid compounds by conventional methods. Most usually, coupling of the sulphonic or sulphinic acid compounds will be via the corresponding sulphonic or sulphinic acid chlorides.

Pharmaceutically acceptable salts of the acidic or basic compounds of the invention can of course be made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated and the weight of the patient. In general, however, the daily dose (whether administered as a single dose or as divided doses) will be in the range 0.001 to 5000 mg per day, and more usually from 1 to 1000 mg per day. Expressed as dosage per unit body weight, a typical dose will be between 0.01 µg/kg and 50 mg/kg, eg between 10 µg/kg and 10 mg/kg.

The invention is now further illustrated by means of the following examples.

EXAMPLE 1
3-(1-adamantanemethylaminocarbonyl)-2-naphthoic acid 2,3-naphthalenedicarboxylic anhydride (198 mg, 1.0 mmol) and 1-adamantanemethylamine (176 mg, 1.0 mmol) were dissolved in dry THF (5 ml) and stirred at room temperature for 1 h. A thick white precipitate was formed and this was isolated by filtration and washed with ether to leave the title compound (229 mg, 69%), $^1$H NMR (d$^6$-DMSO) δ 12.9 (1H, s), 8.3 (2H, s), 8.1 (2H, t), 7.9 (1H, s), 7.6 (2H, m), 2.9 (2H, d), 1.9 (3H, s), 1.6 (6H, q), 1.5 (6H, s).

The material was further characterised and tested as the N-methyl-D-glucamine salt found: C, 62.36; H, 7.77; N, 4.60. $C_{30}H_{42}N_2O_8 \cdot H_2O$ requires C, 62.48; H, 7.69; N, 4:85%

EXAMPLE 2
2-(1S-methoxycarbonyl-ethylaminocarbonyl)-3-(1-adamantanemethylaminocarbonyl)-naphthalene 3-(1-adamantanemethylaminocarbonyl)-2-naphthoic acid (229 mg, 0.52 mmole) (the compound of example 1) and PyBOP (312 mg, 0.6 mmole) were taken up in dry dichloromethane (5 ml) and Hunigs base (0.32 ml, 1.5 mmole) was added. The reaction mixture was stirred under an atmosphere of dry argon for 1 h. L-alanine methyl ester hydrochloride (80 mg, 0.6 mmole) was added and the mixture stirred overnight. The organic layer was washed with 5% potassium hydrogensulphate (5 ml), sodium hydrogencarbonate (5 ml) and saturated brine (5 ml). It was then dried, filtered and evaporated to leave the crude title compound which was further purified by column chromatography (silica 4% methanol and 96% dichloromethane. The title compound (194 mg, 67%) was isolated as a white solid, m.p. 136–8°, found: C, 69.68; H, 7.17; N, 6.04. $C_{27}H_{32}N_2O_4 \cdot H_2O$ requires C, 69.51; H, 7.34; N, 6.00% $^1$H NMR (CDCl$_3$) δ 8.0 (1H, s), 7.9 (1H, s), 7.8 (2H, m), 7.6 (3H, m), 7.0 (1H, t), 4.8 (1H, m), 3.8 (3H, s), 3.2 (2H, m), 2.0 (3H, s), 1.8 (6H, q), 1.6 (6H, s), 1.5 (3H, d).

EXAMPLE 3
3-(2R-carboxypyrrolidino-carbonyl)-2-(1-adamantanemethylaminocarbonyl)-naphthalene a. 3-(2R-benzyloxycarbonyl-pyrrolidino-carbonyl)-2-(1-adamantanemethylaminocarbonyl)-naphthalene The material was made essentially as in example 2 except that D-proline benzyl ester hydrochloride was used as substrate instead of L-alanine methyl ester hydrochloride.

b. 3-(2R-carboxy-pyrrolidino-carbonyl)-2-(1-adamantanemethylaminocarbonyl)-naphthalene The product of step a (195 mg, 0.35 mmol) was dissolved in THF (5 ml) and 10% palladium on charcoal (20 mg) was added. The reaction mixture was stirred overnight under an atmosphere of hydrogen and then filtered through celite and evaporated to yield the title compound (121 mg, 76%), $^1$H NMR (d$^6$-DMSO) δ 12.6 (1H, s), 8.4 (1H, t), 8.2–7.5 (6H, m), 4.3 (1H, m), 3.6–2.2 (6H, m), 2.0 (2H, m), 1.8 (3H, s), 1.5 (6H, q), 1.4 (6H, s).

The material was further characterised and tested as the N-methyl-D-glucamine salt found: C, 60.00; H, 7.60; N, 5.85. $C_{35}H_{49}N_3O_9 \cdot 2.4 H_2O$ requires C, 60.12; H, 7.76; N, 6.00%

EXAMPLE 4
2-(2S-carboxypyrrolidino-carbonyl)-3-(1-adamantanemethylaminocarbonyl)-naphthalene The material was prepared essentially as in example 3 except that L-proline benzyl ester hydrochloride was used in step a instead of D-proline benzyl ester hydrochloride, $^1$H NMR (d$^6$-DMSO) δ 12.6 (1H s), 8.4 (1H, t), 8.2–7.5 (6H, m), 4.3 (1H, m), 3.6–2.2 (6H, m), 2.0 (2H, m), 1.8 (3H, s), 1.5 (6H, q), 1.4 (6H, s).

The material was further characterised and tested as the N-methyl-D-glucamine salt found: C, 61.62; H, 6.98; N, 6.09. $C_{35}H_{49}N_3O_9 \cdot 0.45$ DCM requires C, 61.35; H, 7.24; N, 6.05%

EXAMPLE 5
2-(1R-carboxyethylamino-carbonyl)-3-(1-adamantanemethylaminocarbonyl)-naphthalene The material was prepared essentially as in example 3 except that D-alanine benzyl ester hydrochloride was used in step a instead of D-proline benzyl ester hydrochloride, $^1$H NMR (d$^6$-DMSO) δ 12.6 (1H, s), 8.7 (1H, d), 8.3 (1H, t), 8.1–7.5 (6H, m), 4.4 (1H, m), 2.9 (2H, 2×dd), 1.9 (3H, s), 1.6 (6H, q), 1.5 (6H, s), 1.3 (3H, d).

The material was further characterised and tested as the N-methyl-D-glucamine salt found: C, 61.52; H, 7.54; N, 6.92. $C_{33}H_{47}N_3O_9 \cdot 0.9 H_2O$ requires C, 61.87; H, 7.58; N, 6.56%

EXAMPLE 6
2-(2S-methoxycarbonylpyrrolidino-carbonyl)-3-(1-adamantanemethylaminocarbonyl)-naphthalene The compound of example 4 (88 mg, 0.18 mmol) was dissolved in diethyl ether (30 ml) and an ethereal solution of diazomethane was added until the solution remained yellow. Acetic acid was added to quench the reaction and the solvent was removed by evaporation the last traces by azeotrope with dichloromethane. The solid was dried in vacuo to leave the title compound (61 mg, 67%). found: C, 62.46; H, 6.55; N, 5.19. $C_{29}H_{34}N_2O_4 \cdot 1.22$ DCM requires C, 62.77; H, 6.35; N, 4.84% $^1$H NMR (d$^6$-DMSO) δ 8.4 (1H, t), 8.2–7.5 (6H, m), 4.4 (1H, m), 3.7 (3H, s), 3.6–2.2 (6H, m), 2.0 (2H, m), 1.8 (3H, s), 1.5 (6H, q), 1.4 (6H, s).

EXAMPLE 7
2-(2R-methoxycarbonylpyrrolidino-carbonyl)-3-(1-adamantanemethylaminocarbonyl)-naphthalene The compound was prepared as in example 6 except that the compound of example 3 was used as substrate instead of the compound of example 4. found: C, 69.96; H, 7.06; N, 5.68. $C_{29}H_{34}N_2O_4 \cdot 1.16 H_2O$ requires C, 70.30; H, 7.39; N, 5.65% $^1$H NMR (d$^6$-DMSO) δ 8.4 (1H, t), 8.2–7.5 (6H, m), 4.4 (1H, m), 3.7 (3H, s), 3.6–2.2 (6H, m), 2.0 (2H, m), 1.8 (3H, s), 1.5 (6H, q), 1.4 (6H, s).

EXAMPLE 8

2-(1R-methoxycarbonylethylamino-carbonyl)-3-(1-adamantanemethylaminocarbonyl)-naphthalene The compound was prepared as in example 6 except that the compound of example 5 was used as substrate instead of the compound of example 4. found: C, 71.78; H, 7.37; N, 6.40. $C_{27}H_{32}N_2O_4.0.12\ H_2O$ requires C, 71.95; H, 7.21; N, 6.21% $^1$H NMR (d$^6$DMSO) δ 8.8 (1H, d), 8.3 (1H, t), 8.1 (1H, s), 7.8 (2H, m), 7.5 (3H, m), 4.4 (1H, m), 3.7 (3H, s), 2.9 (2H, 2×dd), 1.9 (3H, s), 1.6 (6H, q), 1.5 (6H, s), 1.4 (3H, d).

EXAMPLE 9

2-(2R-carboxypyrrolidino-carbonyl)-3-(1-adamantanemethyl(N-methyl)aminocarbonyl)-naphthalene a. 3-(1-adamantanemethyl(N-methyl)aminocarbonyl)-2-naphthoic acid This was prepared essentially as in example 1 except that N-methyl-1-adamantanemethylamine was used as substrate instead of 1-adamantanemethylamine.

b. 2-(2R-carboxypyrrolidino-carbonyl)-3-(1-adamantanemethyl(N-methyl)aminocarbonyl)-naphthalene The compound was prepared essentially as in example 3 except that the compound prepared in step a above was used as substrate instead of the compound of example 1 in step a $^1$H NMR (d$^6$-DMSO) δ 12.6 (1H, s), 8.1–7.3 (6H, m), 4.3 (1H, m), 3.6–2.2 (6H, m), 2.86 and 2.84 (3H, 2×s), 2.0 (2H, m), 1.8 (3H, s), 1.5 (6H, q), 1.4 (6H, s).

The material was further characterised and tested as the N-methyl-D-glucamine salt found: C, 61.17; H, 7.98; N, 5.14. $C_{36}H_{51}N_3O_9.1.3\ H_2O.1.4$ dioxan requires C, 61.19; H, 8.00; N, 5.15%

EXAMPLE 10

2-(2R-(1R-carboxyethylaminocarbonyl)pyrrolidino-carbonyl)-3-(1-adamantanemethylaminocarbonyl)-naphthalene a. 2-(2R-(1R-benzyloxycarbonylethylaminocarbonyl)pyrrolidino-carbonyl)-3-(1-adamantanemethylaminocarbonyl)-naphthalene The compound of example 3 (100 mg, 0.22 mmole) and PyBOP (113 mg, 0.22 mmole) were taken up in dry dichloromethane (20 ml) and Hunigs base (0.115 ml, 0.66 mmole) was added. The reaction mixture was stirred under an atmosphere of dry argon for 1 h. D-alanine benzyl ester PTSA salt (76.3 mg, 0.22 mmole) was added and the mixture stirred overnight. The organic layer was washed with 5% potassium hydrogensulphate (5 ml), sodium hydrogencarbonate (5 ml) and saturated brine (5 ml). It was then dried, filtered and evaporated to leave the crude title compound which was further purified by column chromatography (silica and ethyl acetate). The title compound (119 mg, 88%) was isolated as a white solid.

b. 2-(2R-(1R-carboxyethylaminocarbonyl)pyrrolidino-carbonyl)-3-(1-adamantanemethylaminocarbonyl)-naphthalene The compound was prepared as in example 3 step b except that the product of step a above was used as substrate, instead of the product of example 3 step a. $^1$H NMR (d$^6$-DMSO) δ 12.6 (1H, s), 8.6 (1H, m), 8.4 (1H, t), 8.3–7.5 (6H, m), 4.4–3.9 (2H, m), 3.6–3.2 (4H, m), 2.9 (2H, m), 2.0 (2H, m), 1.8 (3H, s), 1.5 (6H, q), 1.4 (6H, s), 1.3 (3H, d)

The material was further characterised and tested as the N-methyl-D-glucamine salt

EXAMPLE 11

2-(2R-carboxymethylaminocarbonylpyrrolidino-carbonyl)-3-(1-adamantanemethylaminocarbonyl)-naphthalene The compound was prepared essentially as in example 10 except that the 4-toluene sulphonic acid salt of glycine benzyl ester was used as substrate in step a instead of the 4-toluene sulphonic acid salt of D-alanine benzyl ester $^1$H NMR (d$^6$-DMSO) δ 12.6 (1H, s), 8.6 (1H, m), 8.4 (1H, t), 8.3–7.5 (6H, m), 4.4–4.2 (1H, m), 3.9–3.2 (6H, m), 2.9 (2H, m), 2.1 (2H, m), 1.8 (3H, S), 1.5 (6H, q), 1.4 (6H, s).

The material was further characterised and tested as the N-methyl-D-glucamine salt

EXAMPLE 12

2-(2R-(1R-carboxyethylaminocarbonyl)pyrrolidino-carbonyl)-3-(1-adamantanemethyl(N-methyl)aminocarbonyl)-naphthalene The compound was prepared essentially as in example 10 except that the compound of example 9 was used as the acidic substrate instead of the compound of example 3 in step a $^1$NMR (d$^6$-DMSO) δ 12.8 (1H, s), 8.3–7.5 (7H, m), 4.3–4.1 (2H, m), 3.6–2.7 (6H, m), 2.92 and 2.91 (3H, 2×s), 2.0 (2H, m), 1.8 (3H, s), 1.5 (6H, q), 1.4 (6H, m), 1.3 (3H, d).

The material was further characterised and tested as the N-methyl-D-glucamine salt found: C, 53.90; H, 8.28; N, 6.52. $C_{39}H_{56}N_4O_{10}.7.2\ H_2O$. requires C, 53.82; H, 8.15; N, 6.44%

EXAMPLE 13

2-(2R-(1S-carboxyethylaminocarbonyl)pyrrolidino-carbonyl)-3-(1-adamantanemethyl(N-methyl)aminocarbonyl)-naphthalene The compound was prepared essentially as in example 12 except that the PTSA salt of L alanine benzyl ester was used as the basic substrate instead of the PTSA salt of D alanine benzyl ester in step a $^1$NMR (d$^6$-DMSO) δ 12.8 (1H, s), 8.3–7.5 (7H, m), 4.3–4.1 (2H, m), 3.6–2.7 (6H, m), 2.92 and 2.91 (3H, 2×s), 2.0 (2H, m), 1.8 (3H, s), 1.5 (6H, q), 1.4 (6H, m), 1.3 (3H, 2×d).

The material was further characterised and tested as the N-methyl-D-glucamine salt found: C, 55.36; H, 7.88; N, 6.40. $C_{39}H_{56}N_4O_{10}.5.7\ H_2O$. 0.1 dioxan requires C, 55.52; H, 8.07; N, 6.57%

EXAMPLE 14

2-(2R-carboxymethylaminocarbonylpyrrolidino-carbonyl)-3-(1-adamantanemethyl(N-methyl)aminocarbonyl)-naphthalene The compound was prepared essentially as in example 12 except that the PTSA salt of glycine benzyl ester was used as the basic substrate instead of the PTSA salt of D alanine benzyl ester in step a $^1$NMR (d$^6$-DMSO) δ 12.7 (1H, s), 8.4–7.5 (7H, m), 4.3–4.1 (1H, m), 3.9–2.7 (8H, m), 2.92 and 2.91 (3H, 2×s), 2.0 (2H, m), 1.8 (3H, s), 1.5 (6H, q), 1.4 (6H, m).

The material was further characterised and tested as the N-methyl-D-glucamine salt found: C, 51.52; H, 7.81; N, 6.29. $C_{38}H_{54}N_4O_{10}$. 8.5 $H_2O$ requires C, 51.84; H, 8.13; N, 6.36%

EXAMPLE 15

2-(1S-(3,5-dicarboxyphenylaminocarbonyl)-2-phenylethylaminocarbonyl)-3-(1-adamantanemethylaminocarbonyl)-naphthalene The compound was prepared essentially as in example 3 except that 1S-(3,5-dibenzyloxycarbonylphenylaminocarbonyl)-2- phenylethylamine (prepared as shown below) was used in step a instead of D-proline benzyl ester. $^1$NMR (d$^6$-DMSO) δ 13.3 (2H, s), 10.1 (1H, s), 9.0 (1H, d), 8.7 (3H, m) 8.2 (2H, m), 8.0 (1H, m), 7.9 (1H, m), 7.6 (2H, m), 7.4 (1H, s), 7.3 (5H, m), 4.8 (1H, m), 3.5–2.9 (4H, m), 1.8 (3H, s), 1.5 (6H, q), 1.4 (6H, m).

The material was further characterised and tested as the di N-methyl-D-glucamine salt found: C, 57.02; H, 7.00; N, 5.63. $C_{54}H_{73}N_5O_{17}$. 3.7 $H_2O$. 0.7 dioxan requires C, 57.21; H, 7.27; N, 5.87%

Preparation of 1S-(3,5-dibenzyloxycarbonylphenylamino-carbonyl)-2-phenylethylamine a. 3,5-dibenzyloxycarbonyl-nitrobenzene 5-nitro-isophthalic acid (21.1 g, 0.1 mol), thionyl chloride (80 ml) and DMF (10 drops) were stirred and heated for about 1 h until a clear solution was obtained. Excess thionyl chloride was removed by evaporation and the residual acid chloride was coevaporated with dichloromethane (2×100 ml) to remove the last traces.

Benzyl alcohol (21.6 g, 0.2 mol) and triethylamine (30.03 g, 0.3 mol) were dissolved in dichloromethane (200 ml) and stirred at 0° under an atmosphere of dry nitrogen and a solution of the acid chloride in dichloromethane (50 ml) was added dropwise over 20 min. The solution was stirred and refluxed for 1 h, and the solution was cooled. The organic layer was washed with water (2×100 ml), saturated sodium hydrogencarbonate solution (100 ml) and dried over magnesium sulphate. The solution was filtered and evaporated to leave the title compound (39.1 g, 100%), $^1$H NMR (CDCl$_3$) δ 9.0 (3H, d), 7.5 (10H, m), 5.5 (4H, s)

b. 3,5-dibenzyloxycarbonyl-aniline 3,5-dibenzyloxycarbonyl-nitrobenzene (3.91 g, 10 mol) was dissolved in ethyl acetate (50 ml) and tin(II)chloride dihydrate (11.27 g, 50 mmol) was added and the mixture stirred and heated at 70 under an atmosphere of nitrogen for 1 h. The mixture was poured carefully onto 5% sodium hydrogencarbonate solution (200 ml) and a further aliquot of ethyl acetate (100 ml) was added. After shaking the organic layer was separated and the aqueous layer was extracted with more ethyl acetate (50 ml). The combined organic layers were washed with brine, and dried, filtered and evaporated to leave a pale yellow solid (3.25 g, 90%), $^1$H NMR (CDCl$_3$) δ 8.1 (1H, d), 7.5 (12H, m), 5.4 (4H, s), 3.8 (2H, bs).

c. N-tert-butyloxycarbonyl-1S-(3,5-dibenzyloxycarbonyl-phenylaminocarbonyl)-2-phenylethylamine BOC-L-phenylalanine (8.76 g, 33 mmol) was dissolved in dry dichloromethane (200 ml) and dry diisopropylethylamine (11.48 ml, 66 mmol) was added followed by PyBROP (15.33 g, 33 mmol). The mixture was stirred at room temperature for 5 min and then 3,5-dibenzyloxycarbonyl-aniline (7.22 g, 20 mmol) was added. The solution was stirred at room temperature for a further 5 h and the solution was then washed sequentially with 2M hydrochloric acid, water, saturated sodium hydrogencarbonate solution and water and finally dried, filtered and evaporated to leave an oil. This was purified by column chromatography (90% dichloromethane and 10% ethyl acetate) to leave the title compound as a white solid (11.0 g, 90%). $^1$H NMR (d$^6$-DMSO) δ 10.5 (1H, s), 8.5 (2H, s), 8.2 (1H, s), 7.3 (15H, m), 5.4 (4H, s), 4.3 (1H, m), 2.9 (2H, m), 1.3 (9H,s)

d. 1S-(3,5-dibenzyloxycarbonylphenylaminocarbonyl)-2-phenylethylamine

N-tert-butyloxycarbonyl-1S-(3,5-dibenzyloxycarbonylphenylaminocarbonyl)-2-phenylethylamine (8.0 g, 13 mmol) was dissolved in trifluoroacetic acid (40 ml) and stirred at room temperature for 30 min. The solvent was removed by evaporation and the residue taken up in dry dichloromethane (50 ml) and basified with diisopropylethylamine. This solution was then used for subsequent transformations.

EXAMPLE 16

2-(2S-(1R-carboxyethylaminocarbonylmethyl)-pyrrolidinocarbonyl)-3-(1-adamantanemethylaminocarbonyl)-naphthalene The compound was prepared essentially as in example 3 except that 2S-(1R-benzyloxycarbonyl-ethylaminocarbonylmethyl)-pyrrolidine in step a instead of D-proline benzyl ester. $^1$NMR (d$^6$-DMSO) δ 8.5 (1H, m), 8.2 (2H, m), 8.0 (3H, m), 7.6 (2H, m), 4.4–3.9 (2H, m), 3.5–2.7 (8H, m), 2.0 (2H, m), 1.8 (3H, s), 1.5 (6H, q), 1.4 (6H, m), 1.2 (3H, 2×d).

The material was further characterised and tested as the N-methyl-D-glucamine salt Found: C, 70.34; H, 6.10; N, 5.36. $C_{42}H_{43}N_3O_7$. 1.0 methanol requires C, 70.39; H, 6.45; N, 5.73%

EXAMPLE 17

2-(1S-(3,5-dimethoxycarbonyl-phenylamino-carbonyl)-2-phenylethylaminocarbonyl)-3-(1-adamantane-methylaminocarbonyl)-naphthalene The compound of example 15 (479 mg, 0.71 mmol) was dissolved in methanol (10 ml) and diazomethane solution in diethyl ether (4.74 ml 0.71 mmol) was added dropwise over 5 min. The solution was evaporated and the crude mixture separated by column chromatography (silica 7.5% methanol and 92.5% dichloromethane) to give two products. The less polar material (rF 0.8) (70 mg) was the title compound of this example. Found: C, 70.34; H, 6.10; N, 5.36. $C_{42}H_{43}N_3O_7$. 1.0 methanol requires C, 70.39; H, 6.45; N, 5.73% $^1$NMR (d$^6$-DMSO) δ 10.2 (1H, s), 9.0 (1H, d), 8.7 (3H, m) 8.2 (2H, m), 8.0 (1H, m), 7.9 (1H, m), 7.6 (2H, m), 7.4 (1H, s), 7.3 (5H, m), 4.8 (1H, m), 3.9 (6H, s), 3.5–2.9 (4H, m), 1.8 (3H, s), 1.5 (6H, q), 1.4 (6H, m).

EXAMPLE 18

2-(1S-(3-methoxycarbonyl-5-carboxy-phenylaminocarbonyl)-2-phenylethylaminocarbonyl)-3-(1-adamantanemethylaminocarbonyl)-naphthalene The more polar material isolated from the chromatography in example 17 (rF 0 3) was designated the title compound of this example. $^1$NMR (d$^6$-DMSO) δ 10.2 (1H, s), 9.0 (1H, d), 8.7 (1H, s), 8.6 (1H, t), 8.4 (1H, s), 8.2 (2H, m), 8.0 (1H, m), 7.9 (1H, m), 7.6 (2H, m), 7.4 (1H, s), 7.3 (5H, m), 4.7 (1H, m), 3.8 (3H, s), 3.5–2.9 (4H, m), 1.8 (3H, s), 1.5 (6H, q), 1.4 (6H, m).

The material was further characterised and tested as the N-methyl-D-glucamine salt Found: C, 57.31; H, 6.28; N, 4.50. $C_{48}H_{58}N_4O_{12}$. 1.8 dicloromethane. 1.9 dioxan requires C, 57.30; H, 6.43; N, 4.66%

EXAMPLE 19

(2R-carboxypyrrolidino-carbonyl)-2-(1-adamantanemethylaminocarbonylmethyl)-4,5-dichlorobenzene a. Preparation of 2-(1-adamantanemethylaminocarbonylmethyl)-4,5-dichlorobenzoic acid The material was prepared essentially as in example 1 except that 4,5-dichlorophthalic anhydride was used as substrate instead of 2,3-naphthalenedicarboxylic anhydride.

b. (2R-carboxypyrrolidino-carbonyl)-2-(1-adamantanemethylaminocarbonylmethyl)-4,5-dichlorobenzene The material was prepared essentially as in example 3 except that the compound of step a above was used as substrate instead of the compound of example 1 in step a $^1$H NMR (d$^6$-DMSO) δ 8.4 (1H, t), 7.9–7.4 (2H, m), 4.2 (1H, m), 3.6–2.7 (6H,m), 2.3 (2H, m), 2.0 (3H, s), 1.7 (6H, q), 1.5 (6H, s)

The material was further characterised and tested as the N-methyl-D-glucamine salt found: C, 52.22; H, 7.20; N, 5.87. $C_{31}H_{45}Cl_2N_3O_9$.2.3 $H_2O$ requires C, 52.03; H, 6.98; N, 5.87%

EXAMPLE 20

1-(1-adamantanemethylaminocarbonyl)-8-naphthoic acid

The material was prepared essentially as in example 1 except that 1,8-naphthalenedicarboxylic anhydride was used as substrate instead of 2,3-naphthalenedicarboxylic anhydride. $^1$H NMR (d$^6$-DMSO) δ 8.5 (1H, m), 8.4 (1H, t), 8.1–7.5 (5H, m), 2.9 (2H, d), 1.9 (3H, s), 1.6 (6H, m), 1.5 (6H, s).

The material was further characterised and tested as the N-methyl-D-glucamine salt found: C, 62.95; H, 7.26; N, 4.86. $C_{30}H_{42}N_2O_8$. $H_2O$ requires C, 62.48; H, 7.69; N, 4.86%

EXAMPLE 21

1/2-(1-adamantanemethylaminocarbonyl)-naphthoic acid Regioisomer 1

The material was prepared essentially as in example 1 except that 1,2-naphthalenedicarboxylic anhydride was used as substrate instead of 2,3-naphthalenedicarboxylic anhydride. Regioisomers were separated by column chromatography (silica 10% methanol and 90% dichloromethane) The less polar compound was designated the compound of this example $^1$H NMR (d$^6$-DMSO) δ 8.4 (1H, t), 8.1–7.5 (6H, m), 2.9 (2H, d), 1.9 (3H, s), 1.6 (6H, m), 1.5 (6H, s).

The material was further characterised and tested as the N-methyl-D-glucamine salt found: C, 61.82; H, 7.74; N, 5.02. $C_{30}H_{42}N_2O_8$.1.3 $H_2O$ requires C, 61.96; H, 7.72; N, 4.81%

EXAMPLE 22

1/2-(1-adamantanemethylaminocarbonyl)-naphthoic acid Regioisomer 2

The more polar regioisomer from the chromatography described in example 21 was designated the compound of this example. $^1$H NMR (d$^6$-DMSO) δ 8.3 (1H, t), 8.1–7.5 (6H, m), 2.9 (2H, d), 1.9 (3H, s), 1.6 (6H, m), 1.5 (6H, s).

The material was further characterised and tested as the N-methyl-D-glucamine salt found: C, 60.93; H, 7.81; N, 5.00. $C_{30}H_{42}N_2O_8$.1.75 $H_2O$ requires C, 61.05; H, 7.77; N, 4.75%

EXAMPLE 23

2-(1R-(3,5-dicarboxyphenylaminocarbonyl)-2-phenylethylaminocarbonyl)-3-(1-adamantanemethylaminocarbonyl)-naphthalene The compound was prepared essentially as in example 3 except that 1R-(3,5-dibenzyloxycarbonylphenylaminocarbonyl)-2-phenyl ethylamine was used in step a instead of D-proline benzyl ester. $^1$NMR (d$^6$-DMSO) δ 13.3 (2H, s), 10.1 (1H, s), 9.0 (1H, d), 8.7 (3H, m) 8.2 (2H, m), 8.0 (1H, m), 7.9 (1H, m), 7.6 (2H, m), 7.4 (1H, s), 7.3 (5H, m), 4.8 (1H, m), 3.5–2.9 (4H, m), 1.8 (3H, s), 1.5 (6H, q), 1.4 (6H, m).

The material was further characterised and tested as the di N-methyl-D-glucamine salt found: C, 57.02; H, 7.00; N, 5.63. $C_{54}H_{73}N_5O_{17}$. 3.7 $H_2O$. 0.7 dioxan requires C, 57.21; H, 7.27; N, 5.87%

EXAMPLE 24

5-(1S-(3,5-dicarboxyphenylaminocarbonyl)-2-phenylethylaminocarbonyl)-6-(1-adamantanemethylaminocarbonyl)-indole a. 4-Methyl-5-nitro-phthalic acid The compound was prepared as in Organic Synthesis collected volume 1, p.408 from 4-methyl phthalic anhydride and fuming nitric acid.

b. Dimethyl 4-methyl-5-nitro-phthalate

The compound prepared in step a (4.4 g, 20 mmol) was suspended in methanol (100 ml) and concentrated sulphuric acid (2 ml) and the resulting suspension was heated under reflux for 48 h. After cooling dichloromethane (100 ml) was added and the organic layer was washed with saturated sodium hydrogencarbonate solution. The aqueous layer was re-extracted with dichloromethane (100 ml) and the combined organic layers were washed with washed with brine and dried. The solution was filtered and evaporated to yield a white solid which was purified by recrystallisation from hot methanol. The title compound was isolated as white needles (3.14 g, 62%).

c. Dimethyl 4-(2-N,N-dimethylaminoethylene)-5-nitrophthalate

The dimethyl ester prepared in step c above (3.14 g, 12.4 mmol) was dissolved in DMF (10 ml) and dimethylformamide dimethyl acetal (4.43 g, 37.2 mmol) was added. The reaction mixture was heated at 150° for 6 h and then allowed to cool. The solution was diluted with ethyl acetate (500 ml) and the solution was washed with brine (6×100 ml), dried filtered and evaporated to leave the title compound as a deep red solid (3.70 g, 97%).

d. 5, 6-Dimethoxycarbonyl-indole

The product of step c (1.50 g) was dissolved in toluene (200 ml) and 10% palladium on charcoal (150 mg) was introduced. The reaction was stirred under an atmosphere of hydrogen at room temperature for 1 h. The catalyst was removed by filtration and the solvent by evaporation to leave the title compound (1.14 g).

e. Indole-5, 6-dicarboxylic acid

To a stirred solution of the dimethyl ester produced in step d (1.14 g, 4.9 mmol) in a 5:1 mixture of ethanol:water (12 ml) was added solid sodium hydroxide (0.49 g, 12.4 mmol). The solution was stirred at a gentle reflux for 3 h. The solution was acidifed on cooling to pH2 with hydrochloric acid and then evaporated. The residue was azeotroped with ethanol and then toluene and dried under vacuum. The residue was then extracted with hot acetone (5×20 ml) and the combined extracts were evaporated to leave the title compound (870 mg).

f. Indole-5, 6-dicarboxylic acid anhydride

The product of step e (870 mg) was heated strongly with a heat gun for 10 minutes under vacuum. This left the title compound (800 mg)

g. 6-(1-adamantanemethylaminocarbonyl)-indole-5-carboxylic acid

The product of step f (2.61 g, 14 mmol) was dissolved in dry THF (50 ml) and triethylamine (2.23 ml, 16 mol) was added followed by 1-adamantanemethylamine (2.5 g, 15.2 mmol). The solution was stirred at room temperature for 1 h. The solution was reduced in volume to ca 30 ml and then partitioned between 2M hydrochloric acid (30 ml) and ethyl acetate (30 ml). the organic layer was dried, filtered and evaporated to leave a 3:2 mixture of regioisomers of which the title compound was the major component.

h. 5-(1S-(3,5-dibenzyloxycarbonylphenylaminocarbonyl)-2-phenylethylaminocarbonyl)-6-(1-adamantanemethylaminocarbonyl)-indole The material was made essentially as in example 2 using the mixture of regioisomers isolated in step g above instead of 3-(1-adamantanemethylaminocarbonyl)-2-naphthoic acid and 1S-(3,5-dibenzyloxycarbonylphenylaminocarbonyl)-2-phenylethylamine (prepared as shown in example 15) instead of L-alanine methyl ester hydrochloride. This led to a 3:2 mixture of regioisomers which were separated by column chromatography (silica 10% ethyl acetate and 90% dichloromethane to 20% ethyl acetate and 80% dichloromethane). The less polar material was designated the title compound.

i. 5-(1S-(3,5-dicarboxyphenylaminocarbonyl)-2-phenylethylaminocarbonyl)-6-(1-adamantanemethylaminocarbonyl)-indole This was prepared essentially as in example 3 step b except that the dibenzyl ester prepared in step h was used as substrate instead of 3-(2R-benzyloxycarbonyl-pyrrolidinocarbonyl)-2-(1-adamantanemethylaminocarbonyl)-naphthalene, $^1$H NMR ($d^6$-DMSO) δ 11.5 (1H, s), 10.2 (1H, s), 8.7 (1H, d), 8.6 (2H, s), 8.4 (1H, t), 8.2 (1H, s), 7.7 (1H, s), 7.5 (1H, s), 7.2 (6H, m), 6.5 (1H, s), 4.8 (1H, m), 3.5 (1H, m), 3.0 (3H, m), 1.8 (3H, s), 1.5 (6H, m), 1.4 (6H, s).

The compound was further characterised and tested as the di-N-methyl-D-glucamine salt. found: C, 58.05; H, 6.99; N, 7.88. $C_{52}H_{72}N_6O_{17}$ $H_2O$ requires C, 58.31; H, 6.96; N, 7.85%

EXAMPLE 25

5-(1S-(3,5-dicarboxyphenylaminocarbonyl)-2-phenylethylaminocarbonyl)-6-(1-adamantanemethylaminocarbonyl)-benzimidazole a. Benzimidazole-5,6-dicarboxylic acid The compound was prepared from 5,6-dimethylbenzimidazole as described in J.Org.Chem. 1987, 52, 2934.

b. Benzimidazole-5,6-dicarboxylic acid anhydride

This was prepared essentially as in example 24 step f except that benzimidazole-5,6-dicarboxylic acid was used as substrate instead of indole-5,6,-dicarboxylic acid.

c. 5-(1-adamantanemethylaminocarbonyl)-benzimidazole-6-carboxylic acid

This was prepared essentially as in example 24 step g except that the product of step b above was used instead of the product of example 24 step f.

d. 5-(1S-(3,5-dibenzyloxycarbonylphenylaminocarbonyl)-2-phenylethylaminocarbonyl)-6-(1-adamantanemethylaminocarbonyl)-benzimidazole This was prepared essentially as in example 24 step h except that 5-(1-adamantanemethylaminocarbonyl)-benzimidazole-6-carboxylic acid was used as substrate instead of 6-(1-adamantanemethylaminocarbonyl)-indole-5-carboxylic acid and no separation of regioisomers was required.

e. 5-(1S-(3,5-dicarboxyphenylaminocarbonyl)-2-phenylethylaminocarbonyl)-6-(1-adamantanemethylaminocarbonyl)-benzimidazole This was prepared essentially as in example 24 step i except that the dibenzyl ester prepared in step d was used as substrate instead of the product of example 24 step h. $^1$H NMR ($d^6$-DMSO) δ 10.2 (1H, m), 8.9 (1H, d), 8.7 (2H, s), 8.5 (1H, t), 8.4 (1H, s), 8.2 (1H, m), 7.9 (1H, br s), 7.3 (7H, m), 4.7 (1H, m), 3.5 (1H, m), 3.0 (3H, m), 1.8 (3H, s), 1.5 (6H, m), 1.4 (6H, s).

The compound was further characterised and tested as the di-N-methyl-D-glucamine salt. found: C, 55.11; H, 7.09; N, 8.82. $C_{51}H_{71}N_7O_{17}$.3.25 $H_2O$ requires C, 55.06; H, 7.02; N, 8.81%

EXAMPLE 26

6-(1S-(3,5-dicarboxyphenylaminocarbonyl)-2-phenylethylaminocarbonyl)-5-(1-adamantanemethylaminocarbonyl)-indole This was prepared essentially as in example 24 except that the more polar dibenzyl ester prepared in step h was used as substrate in step i instead of the product of example 24 step h. $^1$H NMR ($d^6$-DMSO) δ 11.5 (1H, s), 10.2 (1H, s), 8.8 (1H, d), 8.6 (2H, s), 8.4 (1H, t), 8.2 (1H, s), 7.9 (1H, s), 7.5 (1H, t), 7.2–7.4 (5H, m), 7.0 (1H, s), 6.6 (1H, s), 4.7 (1H, m), 3.4 and 2.9 (4H, m), 1.8 (3H, s), 1.5 (6H, m), 1.3 (6H, s).

EXAMPLE 27

5-(1S-(3,5-dicarboxyphenylaminocarbonyl)-2-(2-fluorophenyl)ethylaminocarbonyl)-6-(1-adamantanemethylaminocarbonyl)-indole and regioisomer with substituents at positions 5 and 6 reversed This was prepared essentially as in example 24 except that 1S-(3,5-dibenzyloxycarbonyl-phenylaminocarbonyl)-2-(2-fluorophenyl)ethylamine was used in step h instead of 1S-(3,5-dibenzyloxycarbonylphenylaminocarbonyl)-2-phenylethylamine and the mixture of regioisomers formed during this step were not separated. The 1S-(3,5-dibenzyloxy-carbonylphenylaminocarbonyl)-2-(2-fluorophenyl)ethylamine was prepared essentially as in example 15 steps c and d except that BOC-L-2-fluorophenylalanine was used in step c instead of BOC-L-phenylalanine. $^1$H NMR ($d^6$-DMSO) δ 11.5 (1H, s), 10.3 and 10.2 (1H, 2×s), 8.8 (1H, m), 8.7 (2H, s), 8.5 (1H, m), 8.2 (1H, s) 7.9 and 7.8 (1H, 2×s), 7.5–7.0 (6H, m), 6.6 and 6.5 (1H, 2×s), 4.8 (1H, m), 3.4 and 2.9 (4H, m), 1.8 (3H, s), 1.5 (6H, m), 1.3 (6H, s).

The compound was further characterised and tested as the di-N-methyl-D-glucamine salt found: C, 55.28; H, 7.09; N, 7.41. $C_{52}H_{71}FN_6O_{17}$. 3.33 $H_2O$ requires C, 55.22; H, 6.92; N, 7.43%

EXAMPLE 28

5-(1S-(3,5-dicarboxyphenylaminocarbonyl)-2-(3-fluorophenyl)ethylaminocarbonyl)-6-(1-adamantanemethylaminocarbonyl)-indole and regioisomer with substituents at positions 5 and 6 reversed This was prepared essentially as in example 24 except that 1S-(3,5-dibenzyloxycarbonyl-phenylaminocarbonyl)-2-(3-fluorophenyl)ethylamine was used in step h instead of 1S-(3,5-dibenzyloxycarbonylphenylaminocarbonyl)-2-phenylethylamine and the mixture of regioisomers formed during this step were not separated. The 1S-(3,5-dibenzyloxy-carbonylphenylaminocarbonyl)-2-(3-fluorophenyl)ethylamine was prepared essentially as in example 15 steps c and d except that BOC-L-3-fluorophenylalanine was used in step c instead of BOC-L-phenylalanine. $^1$H NMR ($d^6$-DMSO) δ 11.5 and 11.1 (1H, 2×s), 10.3 and 10.2 (1H, 2×s), 8.8 (1H, m), 8.7 (2H, s), 8.4 (1H, m), 8.2 (1H, s), 7.9 and 7.7 (1H, 2×s), 7.5–7.0 (6H, m), 6.6 and 6.5 (1H, 2×s), 4.8 (1H, m), 3.4 and 2.9 (4H, m), 2.0 and 1.8 (3H, m), 1.5 (6H, m), 1.3 (6H, s).

The compound was further characterised and tested as the di-N-methyl-D-glucamine salt found: C, 55.80; H, 6.84; N, 7.25. $C_{52}H_{71}FN_6O_{17}$. 2.9 $H_2O$ requires C, 55.59; H, 6.89; N, 7.48%

EXAMPLE 29

5-(1R-(3,5-dicarboxyphenylaminocarbonyl)-2-phenylethylaminocarbonyl)-6-(1-adamantanemethylaminocarbonyl)-indole and regioisomer with substituents at positions 5 and 6 reversed This was prepared essentially as in example 24 except that 1R-(3,5-dibenzyloxycarbonyl-phenylaminocarbonyl)-2- phenyl)ethylamine was used in step h instead of 1S-(3,5-dibenzyloxycarbonylphenylaminocarbonyl)-2-phenylethyl amine and the mixture of regioisomers formed during this step were not separated. The 1R-(3,5-dibenzyloxy-carbonylphenylaminocarbonyl)-2-phenylethylamine was prepared essentially as in example 15 steps c and d except that BOC-D-phenylalanine was used in step c instead of BOC-L-phenylalanine. $^1$H NMR (d$^6$-DMSO) δ 11.5 (1H, s), 10.3 and 10.2 (1H, 2×s), 8.8 (1H, m), 8.7 (2H, s), 8.4 (1H, m), 8.2 (1H, s), 7.9 and 7.7 (1H, 25 2×s), 7.5–7.0 (7H, m), 6.6 and 6.5 (1H, 2×s), 4.7 (1H, m), 3.4 and 2.9 (4H, m), 1.8 (3H, m), 1.5 (6H, m), 1.3 (6H, s).

The compound was further characterised and tested as the di-N-methyl-D-glucamine salt found: C, 55.51; H, 7.29; N, 7.34. $C_{52}H_{72}N_6O_7$. 4.1 $H_2O$ requires C, 55.44; H, 7.17; N, 7.46%

EXAMPLE 30

5-(1S-(3,5-dicarboxyphenylaminocarbonyl)-2-(4-hydroxyphenyl)ethylaminocarbonyl)-6-(1-adamantanemethylaminocarbonyl)-indole and regioisomer with substituents at positions 5 and 6 reversed This was prepared essentially as in example 24 except that 1S-(3,5-dibenzyloxycarbonyl-phenylaminocarbonyl)-2-(4-hydroxy phenyl)ethylamine was used in step h instead of 1S-(3,5-dibenzyloxycarbonylphenylaminocarbonyl)-2-phenylethylamine and the mixture of regioisomers formed during this step were not separated. The 1S-(3,5-dibenzyloxy-carbonylphenylaminocarbonyl)-2-(4-hydroxy phenyl)ethylamine was prepared essentially as in example 15 steps c and d except that BOC-L-tyrosine(O-benzyl ether) was used in step c instead of BOC-L-phenylalanine and pentamethylbenzene and trifluoroacetic acid were used together to remove both the BOC group and the tyrosinyl benzyl protection during the course of step d. $^1$H NMR (d$^6$-DMSO) δ 11.5 and 11.4 (1H, 2×s), 10.3 and 10.2 (1H, 2×s), 9.2 (1H, br s), 8.8 (1H, m), 8.7 (2H, s), 8.4 (1H, m), 8.2 (1H, s), 7.9 and 7.7 (1H, 2×s), 7.5 (1H, m), 7.2 (3H, m), 6.7 (2H, m), 6.6 and 6.5 (1H, 2×s), 4.6 (1H, m), 3.4 and 2.9 (4H, m), 2.0 and 1.8 (3H, m), 1.6 (6H, m), 1.4 (6H, s).

The compound was further characterised and tested as the di-N-methyl-D-glucamine salt found: C, 53.41; H, 6.95; N, 6.85. $C_{52}H_{72}N_6O_{18}$. 5.9 $H_2O$ requires C, 53.13; H, 7.19; N, 7.15%

EXAMPLE 31

5-(1S-(3,5-dicarboxyphenylaminocarbonyl)-2(4-aminophenyl)ethylaminocarbonyl)-6-(1-adamantanemethylaminocarbonyl)-indole and regioisomer with substituents at positions 5 and 6 reversed This was prepared essentially as in example 24 except that 1S-(3,5-dibenzyloxycarbonyl-phenylaminocarbonyl)-2-(4-nitrophenyl)ethylamine was used in step h instead of 1S-(3,5-dibenzyloxycarbonylphenylaminocarbonyl)-2-phenylethylamine and the mixture of regioisomers formed during this step were not separated. The nitro group was reduced to the amino group during the final deprotection step. The 1S-(3,5-dibenzyloxy-carbonylphenylaminocarbonyl)-2-(4-nitrophenyl)ethylamine was prepared essentially as in example 15 steps c and d except that BOC-L-4-nitrophenylalanine was used in step c instead of BOC-L-phenylalanine. $^1$H NMR (d$^6$-DMSO) δ 11.5 (1H, 2×s), 10.2 and 10.1 (1H, 2×s), 8.8 (1H, m), 8.7 (2H, s), 8.4 (1H, m), 8.2 (1H, s), 7.9 and 7.7 (1H, 2×s), 7.5–7.0 (4H, m), 6.5 (3H, 2×s), 4.6 (1H, m), 3.2 and 2.8 (4H, m), 1.8 (3H, m), 1.5 (6H, m), 1.4 (6H, s).

The compound was further characterised and tested as the mono-N-methyl-D-glucamine salt found: C, 58.32; H, 6.73; N, 9.00. $C_{45}H_{56}FN_6O_{12}$. 3.0 $H_2O$ requires C, 58.30; H, 6.74; N, 9.06%

EXAMPLE 32

5-(1S-(3,5-dicarboxyphenylaminocarbonyl)-2-(4-iodophenyl)ethylaminocarbonyl)-6-(1-adamantanemethylaminocarbonyl)-indole a. 3,5-di-t-butyloxycarbonyl-nitrobenzene 5-Nitroisophthalic acid (4.22 g, 20 mmol) was suspended in dichloromethane (80 ml) and concentrated sulphuric acid (1 ml) was added. The solution was stirred and then saturated with isobutylene gas. The reaction vessel was stoppered and stirred at room temperature overnight. The solution was filtered and anhydrous potassium carbonate was added to the filtrate. the solution was filtered and evsaporated and the residue recrystallised from ethanol to leave the title compound as a white solid (2.2 g).

b. 3,5-di-t-butyloxycarbonyl-aniline

The nitro compound prepared in step a (2.2 g, 6.8 mmol) was dissolved in a mixture of THF (50 ml) and methanol (50 ml) and 10% palladium on charcoal (100 mg) was added. The reaction mixture was stirred under an atmosphere of hydrogen overnight. The catalyst was removed by filtration and the title compound (1.94 g) isolated by evaporation.

c. N-(9-fluorenylmethoxycarbonyl)-1S-(3,5-di-t-butyloxycarbonylphenylaminocarbonyl)-2-(4-iodophenyl)ethylamine FMOC-L-4-iodophenylalanine (3.85 g, 7.5 mmol) and PyBROP (3.5 g, 7.5 mmol) were stirred in a mixture of dichloromethane (25 ml) and diisopropylethylamine (2.63 ml, 15 mmol) for 5 min. A solution of 3,5-di-t-butyloxycarbonylaniline (1.94 g, 6.6 mmol) in dichloromethane (15 ml) was added followed by DMAP (5 mg). The resulting solution was stirred at room temperature overnight. The solution was washed with 2M hydrochloric acid (2×25 ml) and brine (25 ml) dried filtered and evaporated. The residue was recrystallised from ethanol to leave the title compound as a white solid (1.91 g).

d. 5-(3,5-di-t-butyloxycarbonylphenylaminocarbonyl)-2-(4-modophenyl)ethylamine

The FMOC derivative produced in step c (1.7 g) was dissolved in diethylamine (20 ml) and stirred at room temperature for 2 h. The solution was evaporated and then the residue was purifed by column chromatography (silica 50% dichloromethane and 50% ethyl acetate) to leave the title compound.

e. 5-(1S-(3,5-di-t-butyloxycarbonylphenylaminocarbonyl)-2-(4-iodophenyl)ethylaminocarbonyl)-6-(1-adamantanemethylaminocarbonyl)-indole The product of step d (220 mg, 0.35 mmol) and the product of example 24 step g (73 mg, 0.35 mmol) were dissolved in dry DMF (3 ml) and DCCI (73 mg, 0.35 mmol), HOBT (50 mg, 0.35 mol) and DMAP (5 mg) were added. The solution was stirred at room temperature for 4 h. The DCU produced was removed by filtration and washed with dichloromethane. The filtrate was further diluted with dichloromethane and then washed with 2M hydrochloric acid (2×10 ml), brine (10 ml) and water (10 ml) before being dried (magnesium sulphate) and evaporated to leave a mixture of regioisomers at positions 5 and 6 of the indole ring. The regioisomers were separated by column chromatography (silica 80% dichloromethane and 20% ethyl acetate) to leave the less polar material as title compound (55 mg).

f. 5-(1S-(3,5-di-carboxyphenylaminocarbonyl)-2-(4-iodophenyl)ethylaminocarbonyl)-6-(1-adamantanemethylaminocarbonyl)-indole The product of step e (50 mg) was dissolved in TFA (1 ml) and stirred at room temperature for 1 h. The solution was filtered and evaporated and the residue co-evaporated several times with diethyl ether. The residue was triturated with ether and the solid filtered off and dried. The title compound was left as a white solid. $^1$H NMR (d$^6$-DMSO) δ 11.5 (1H, s), 10.7 (1H, s), 8.8 (1H, d), 8.5 (1H, m), 8.4 (2H, s), 8.2 (1H, s), 7.7 (3H, s), 7.5 (2H, m), 7.2 (2H, m), 7.0 (1H, s), 6.5 (1H, s), 4.7 (1H, m), 3.4 and 2.9 (4H, m), 1.9 (3H, s), 1.5 (6H, m), 1.3 (6H, s).

EXAMPLE 33

5-(1S-(3,5-dipivaloyloxymethyloxycarbonylphenylaminocarbonyl)-2-phenylethylaminocarbonyl)-6-(1-adamantanemethylaminocarbonyl)-indole The compound of example 24 (331 mg, 0.5 mmol) was dissolved in DMF (2.5 ml) and cesium carbonate (168 mg, 0.5 mmol) and pivaloyloxymethyl chloride (0.144 ml, 1.0 mmol) were added. After 30 min at room temperature the reaction mixture was partitioned between ethyl acetate (30 ml) and 2M hydrochloric acid (30 ml). The organic layer was washed with water (3×20 ml), dried (magnesium sulphate) and evaporated to leave a white foam which was purifed by column chromatography (silica 80% dichloromethane and 20% ethyl acetate) to leave the title compound, found: C, 67.29; H, 6.61; N, 6.28. $C_{50}H_{58}N_4O_{11}$ requires C, 67.40; H, 6.56; N, 6.29%, $^1$H NMR (d$^6$-DMSO) δ 11.5 (1H, s), 10.3 (1H, s), 8.8 (3H, m), 8.5 (1H, t), 8.2 (1H, s), 7.7 (1H, s), 7.5 (1H, t), 7.2–7.5 (5H, m), 7.2 (1H, s), 6.5 (1H, s), 6.0 (4H, m), 4.7 (1H, m), 3.4 and 2.9 (4H, m), 1.8 (3H, s), 1.3–1.6 (12H, m), 1.1 (18H, s).

EXAMPLE 34

5-(1S-(3,5-dihydroxyaminocarbonylphenylaminocarbonyl)-2-phenylethylaminocarbonyl)-6-(1-adamantanemethylaminocarbonyl)-indole The compound of example 24 (300 mg, 0.45 mmol) was dissolved in DMF (5 ml). Pentafluorophenol (184 mg, 1.0 mmol) and DCCI (206 mg, 1.0 mmol) were introduced and the mixture stirred at room temperature for 3 h. The solution was filtered and hydroxylamine hydrochloride (100 mg, 1.4 mmol) and triethylamine (0.2 ml) was added. The solution was stirred overnight and then evaporated. The material left was partitioned between ethyl acetate and 2M hydrochloric acid. The organic layer was dried, filtered and evaporated to leave a solid which was triturated with several portions of diethyl ether. The white solid left by this procedure was isolated by filtration and dried. This was then recrystallised from a 1:1 mixture of hexane and ethyl acetate to leave the title compound (110 mg). $^1$H NMR (d$^6$-DMSO) δ 11.6 (1H, s), 11.2 (2H, br s), 10.2 (1H, s), 8.8 (1H, d), 8.5 (3H, m), 8.0–7.1 (9H, m), 6.5 (1H, s), 4.7 (1H, m), 3.4 and 2.9 (4H, m), 1.8 (3H, s), 1.6 (6H, m), 1.3 (6H, s).

EXAMPLE 35

5-(1S-(3,5-dimethoxycarbonylphenylaminocarbonyl)-2-phenylethylaminocarbonyl)-6-(1-adamantanemethylaminocarbonyl)-indole The compound of example 24 (155 mg, 0.23 mmol) was dissolved in methanol (5 ml). A 2M hexane solution of trimethylsilyldiazomethane in hexane (1 ml) was added and left to stir for 30 min. The yellow solution was evaporated and the residue partitioned between ethyl acetate and water. The aqueous phase was extracted with ethyl acetate and the combined organic extracts were dried (magnesium sulphate), filtered and evaporated. The residue was recrystallised from methanol to leave the title compound found: C, 66.00; H, 6.10; N, 7.91. $C_{40}H_{42}N_4O_7$. 1.9 $H_2O$ requires C, 66.27; H, 6.37; N, 7.73%, $^1$H NMR (CDCl$_3$) δ 9.9 (1H, d), 9.2 (1H, s), 8.7 (2H, d), 8.4 (1H, t), 7.5 (1H, s), 7.3 (7H, s), 6.7 (1H, s), 6.4 (2H, m), 5.0 (1H, m), 3.9 (6H, s), 3.4 and 2.9 (4H, m), 1.9 (3H, s), 1.6 (6H, m), 1.4 (6H, s).

EXAMPLE 36

5-(1S-(3,5-dicarboxyphenylaminocarbonyl)-2-phenylethylaminocarbonyl)-6-(1-adamantanemethylaminocarbonyl)-N-methyl-indole a. 5-(1S-(3,5-dibenzyloxycarbonylphenylaminocarbonyl)-2-phenylethylaminocarbonyl)-6-(1-adamantanemethylaminocarbonyl)-N-methyl-indole 5-(1S-(3,5-dibenzyloxycarbonylphenylaminocarbonyl)-2-phenylethylaminocarbonyl)-6-(1-adamantanemethylaminocarbonyl)-indole, the title compound of Example 24 step h. (211 mg, 0.25 mmol) was dissolved in dry THF (1 ml) and dry DMF (0.5 ml). The reaction mixture was stirred under an atmosphere of dry nitrogen and sodium hydride (15 mg, 0.3 =mol) was added. Hydrogen gas was evolved for about 5 min and then methyl iodide (0.04 ml) was added. The mixture was stirred at room temperature for 1 h, diluted with brine (20 ml) and extracted with dichloromethane (20 ml). The organic layer was washed with brine (2×20 ml), dried (magnesium sulphate) and evaporated. The residue was purified by column chromatography (silica 85% dichloromethane and 15% ethyl acetate) to leave the title compound (90 mg).

b. 5-(1S-(3,5-dicarboxyphenylaminocarbonyl)-2-phenylethylaminocarbonyl)-6-(1-adamantanemethylaminocarbonyl)-N-methyl-indole This was prepared essentially as in example 3 step b except that the product of step a above was used as substrate instead of 3-(2R-benzyloxycarbonyl-pyrrolidino-carbonyl)-2-(1-adamantane methylaminocarbonyl)-naphthalene. $^1$H NMR (d$^6$-DMSO) δ 10.2 (1H, s), 8.8 (1H, d), 8.7 (2H, s), 8.4 (1H, t), 8.2 (1H, s), 7.7 (1H, s), 7.5 (1H, d), 7.2–7.4 (5H, m), 7.1 (1H, s), 6.5 (1H, d), 4.7 (1H, m), 3.8 (3H, s), 3.4 and 2.9 (4H, m), 1.8 (3H, s), 1.5 (6H, m), 1.4 (6H, s).

The compound was further characterised and tested as the di-N-methyl-D-glucamine salt found: C, 59.47; H, 7.24; N, 7.79. $C_{53}H_{74}N_6O_{17}$ requires C, 59.65; H, 6.99; N, 7.88%

EXAMPLE 37

6-(1S-(3,5-dicarboxyphenylaminocarbonyl)-2-phenylethylaminocarbonyl)-5-(1-adamantanemethylaminocarbonyl)-N-methyl-indole This was prepared essentially as in example 36 except that the more polar dibenzyl ester prepared in example 24 step h was used as substrate in step a instead of 5-(1S-(3,5-dibenzyloxycarbonylphenylaminocarbonyl)-2-phenylethylaminocarbonyl)-6-(1-adamantanemethylaminocarbonyl)-indole $^1$H NMR (d$^6$-DMSO) δ 10.2 (1H, s), 8.7 (2H, m), 8.4 (1H, t), 8.2 (1H, s), 7.9 (1H, s), 7.5 (1H, d), 7.2–7.4 (5H, m), 6.8 (1H, s), 6.6 (1H, d), 4.7 (1H, m), 3.8 (3H, s), 3.4 and 2.9 (4H, m), 1.8 (3H, s), 1.5 (6H, m), 1.4 (6H, s).

The compound was further characterised and tested as the di-N-methyl-D-glucamine salt found: C. 56.77; H, 7.22; N, 7.61. $C_{53}H_{74}N_6O_{17}$. 3$H_2O$ requires C, 56.77; H, 7.19; N, 7.50%

EXAMPLE 38

5-(1S-(3,5-methoxyaminocarbonylphenylaminocarbonyl)-2-phenylethylaminocarbonyl)-6-(1-adamantanemethylaminocarbonyl)-indole and regioisomer with substituents at positions 5 and 6 reversed The compound was prepared essentially as in example 24 except that 1S-(3,5- dimethoxycarbonylphenylaminocarbonyl)-2-phenylethylamine was used in step h instead of 1S-(3,5-dibenzyloxycarbonylphenylaminocarbonyl)-2-phenylethylamine, DCCI/HOBT coupling conditions were used and the mixture of regioisomers formed during this step were not separated. The 1S-(3,5-dimethoxycarbonylphenylaminocarbonyl)-2-phenylethylamine was prepared by hydrogenation of the product of example 15 steps c followed treatment of the resulting diacid with O-methyl-hydroxamic acid hydrochloride in the presence of PyBROP and diisopropylethylamine. found: C, 61.86; H, 6.70; N, 10.83. $C_{40}H_{44}N_6O_7$. 3.15 $H_2O$ requires C, 61.79; H, 6.52; N, 10.81% $^1$H NMR ($d^6$-DMSO) δ 11.8 (2H, br s), 11.5 (1H, s), 10.3 and 10.2 (1H, 2xs), 8.8 (1H, m), 8.5 (3H, m), 8.0–7.1 (9H, m), 6.5 (1H, m), 4.7 (1H, m), 3.7 (6H, 2xs), 3.6–2.7 (4H, m), 1.8 (3H, s), 1.5 (6H, m), 1.4 (6H, s).

EXAMPLE 39

5-(1S-(3-methoxycarbonyl-5-pivaloyloxymethyloxycarbonyl-phenylaminocarbonyl)-2-phenylethylaminocarbonyl)-6-(1-adamantanemethylaminocarbonyl)-indole and regioisomer with substituents at positions 5 and 6 reversed The compound was prepared essentially as in example 38 except that 1S-(3-methoxycarbonyl-5-pivaloyloxymethyloxycarbonyl-phenylaminocarbonyl)-2-phenylethylamine was used in step h instead of 1S-(3,5-dimethoxycarbonylphenylaminocarbonyl)-2-phenylethylamine. 1S-(3-methoxycarbonyl-5-pivaloyloxymethyloxycarbonylphenylaminocarbonyl)-2-phenylethylamine was prepared essentially as in example 15 step c except that 3-methoxycarbonyl-5-pivaloyloxymethyloxycarbonyl-aniline was used as substrate instead of 3,5-dibenzyloxycarbonylaniline. This in turn was prepared by the treatment of monomethyl-5-nitroisophthalate with cesium carbonate and chloromethylpivalate followed by catalytic hydrogenation, found: C, 68.01; H, 6.42; N, 6.84. $C_{45}H_{50}N_4O_9$ requires C, 68.34; H, 6.37; N, 7.08% $^1$H NMR ($d^6$-DMSO) δ 11.5 (1H, s), 10.3 and 10.2 (1H, 2xs), 8.8 (3H, m), 8.5 (1H, m), 8.2 (1H, s), 7.9 and 7.7 (1H, 2xs), 7.5–7.0 (7H, m), 6.5 (1H, m), 5.9 (2H, s), 4.7 (1H, m), 3.9 (3H, s), 3.4 and 2.7 (4H, m), 1.8 (3H, s), 1.5 (6H, m), 1.4 (6H, s), 1.1 (9H, s)

EXAMPLE 40

5-(1S-(3-methoxycarbonyl-5-carboxy-phenylaminocarbonyl)-2-phenylethylaminocarbonyl)-6-(1-adamantanemethylaminocarbonyl)-indole and regioisomer with substituents at positions 5 and 6 reversed The compound of example 39 (300 mg) was treated with a saturated solution of ammonia in methanol (20 ml). The solution was stirred for 1 h and on evaporation the residue was purified by column chromatography (silica 95% dichloromethane and 5% methanol) to leave the title compound (52 mg), $^1$H NMR ($d^6$-DMSO) δ 11.5 (1H, s), 10.3 and 10.2 (1H, 2xs), 8.8 (1H, m), 8.6 (2H, m), 8.5 (1H, m), 8.2 (1H, s), 7.9 and 7.7 (1H, 2xs), 7.5–7.0 (7H, m), 6.7 (1H, s), 4.7 (1H, m), 3.8 (3H, s), 3.4 and 2.7 (4H, m), 1.8 (3H, s), 1.5 (6H, m), 1.4 (6H, s).

The compound was further characterised and tested as the N-methyl-D-glucamine salt found: C, 60.71; H, 6.96; N, 7.89. $C_{46}H_{57}N_5O_{12}$.2$H_2O$ requires C, 60.85; H, 6.77; N, 7.71%

EXAMPLE 41

5-(1S-(3,5-dicarboxyphenylaminocarbonyl)-2-phenylethylaminocarbonyl)-6-(1-adamantanemethyl-N-methyl-aminocarbonyl)-indole and regioisomer with substituents at positions 5 and 6 reversed The material was prepared essentially as in example 24 except that N-methyl-1-adamantanemethylamine was used in step g instead of 1-adamantanemethylamine and that the regioisomers were not separated at the end of step h, $^1$H NMR ($d^6$-DMSO) δ 11.5 and 11.3 (1H, 2xs), 10.3 and 10.2 (1H, 2xs), 8.7 (1H, m), 8.6 (2H, m), 8.5 (1H, m), 8.2 (1H, s), 7.9 and 7.8 (1H, 2xs), 7.5–7.0 (7H, m), 6.5 (1H, m), 4.7 (1H, m), 3.2 (4H, m), 2.7 (3H, m), 1.8 (3H, s), 1.5 (12H, m).

The compound was further characterised and tested as the di-N-methyl-D-glucamine salt found: C, 59.76; H, 7.04; N, 7.68. $C_{53}H_{74}N_6O_{17}$ requires C, 59.65; H, 6.99; N, 7.88%

EXAMPLE 42

5-(1S-(3,5-dicarboxyphenylaminocarbonyl)-2-phenylethylaminocarbonyl)-6-(cycloheptanemethylaminocarbonyl)-indole and regioisomer with substituents at positions 5 and 6 reversed The material was prepared essentially as in example 24 except that cycloheptanemethylamine was used in step g instead of 1-adamantanemethylamine and that the regioisomers were not separated at the end of step h, $^1$H NMR ($d^6$-DMSO) δ 11.5 (1H, s), 10.3 and 10.2 (1H, 2xs), 8.7 (3H, m), 8.5 (1H, m), 8.2 (1H, s), 7.8 and 7.6 (1H, 2xs), 7.5–7.0 (7H, m), 6.5 (1H, m), 4.7 (1H, m), 3.2–2.7 (4H, m), 1.7–1.0 (13H, m).

The compound was further characterised and tested as the di-N-methyl-D-glucamine salt found: C, 54.09; H, 7.17; N, 7.41. $C_{49}H_{70}N_6O_{17}$.4.3$H_2O$ requires C, 53.85; H, 7.25; N, 7.69%

EXAMPLE 43

5-(1S-(3,5-diaminophenylaminocarbonyl)-2-phenylethylaminocarbonyl)-6-(1-adamantanemethyl-N-methylaminocarbonyl)-indole and regioisomer with substituents at positions 5 and 6 reversed a. N-tert-butyloxycarbonyl-1S-(3,5-dinitrophenylaminocarbonyl)-2-phenylethylamine 3,5-Dinitroaniline (3.44 g, 18.7 mmol) and BOC-L-phenylalanine methyl ester (5.24 g, 18.7 mmol) were dissolved in 1,2-dichloroethane (50 ml) and cooled to −10°. Trimethylaluminium (3.6 ml, 37.4 mmol) was added and the mixture was allowed to warm to room temperature and stirred for 10d. 2M sodium hydroxide solution (20 ml) was added and the reaction mixture filtered through celite, washed with brine and treated with three aliquots of magnesium sulphate, charcoal and celite. After evaporation, the residual material was chromatographed (silica gradient 5–10% ethyl acetate and dichloromethane) and recrystallised from a mixture of dichloromethane and hexane to leave the title compound as a pale yellow solid (2.99 g)

b. 5-(1S-(3,5-diaminophenylaminocarbonyl)-2-phenylethylaminocarbonyl)-6-(1-adamantanemethyl-N-methylaminocarbonyl)-indole and regioisomer with substituents at positions 5 and 6 reversed The material was prepared essentially as in example 24 except that the product of step a above was used in step h after the BOC group had been removed with trifluoroacetic acid, instead of 1S-(3,5-dibenzyloxycarbonylphenylaminocarbonyl)-2-phenylethylamine and the mixture of regioisomers formed during this step were not separated. The amine groups were formed by the final hydrogenation step, $^1$H NMR ($d^6$-DMSO) δ 11.5 (1H, 2xs), 9.4 (1H, d), 8.5 (1H, dd), 8.3 (1H, m), 7.8–6.5 (9H, m), 6.4 (2H, dd), 5.6 (1H, d), 4.7 (1H, m), 4.6 4H, br s), 3.0–2.8 (4H, m), 2.7 (3H, m), 1.9 (3H, m), 1.6 (6H, m), 1.5 (6H, m).

The compound was further characterised and tested as the di hydrochloride salt found: C, 54.90; H, 6.63; N, 10.88. $C_{36}H_{42}Cl_2N_6O_3.6H_2O$ requires C, 55.18; H, 6.92; N, 10.73%

EXAMPLE 44
5-(1S-(3,5-dicarboxyphenylaminocarbonyl)-2-phenylethylaminocarbonyl)-6-(1-adamantanemethylaminocarbonyl)-N-acetyl-indole The unseparated mixture of diastereomers isolated at the end of example 24 step h (251 mg, 0.3 mmol) was dissolved in DMF (0.5 ml) and 60% sodium hydride (14 mg, 0.36 mmol) was added. This was accompanied with effervescence. To the yellow solution was added acetyl chloride (0.026 ml, 0.36 mmol) and the mixture was stirred for 2 h at RT. A few drops of water were introduced before the whole reaction mixture was poured into water (0.5 ml). The aqueous mixture was extracted with diethyl ether (5×5 ml) and the combined organic layers dried (magnesium sulphate). The product was finally purifed by column chromatography (silica 10% ethyl acetate and 90% dichloromethane) to leave the dibenzyl ester of the title compound (92 mg). This was converted to the title compound by hydrogenation essentially as described in example 3 step b. $^1$H NMR ($d^6$-DMSO) δ 13.3 (2H, br s), 10.2 (1H, 2×s), 8.9 (1H, m), 8.6 (3H, m), 8.1 (1H, s), 8.1–7.9 (2H, m), 7.4–7.1 (6H, m), 6.8 (1H, m), 4.7 (1H, m), 3.4–2.9 (4H, m), 2.7 (3H, 2×s), 1.9 (3H, m), 1.6 (6H, m), 1.5 (6H, m).

The compound was further characterised and tested as the di-N-methyl-D-glucamine salt found: C, 56.96; H, 7.11; N, 7.44. $C_{54}H_{74}N_6O_{18}.2.6H_2O$ requires C, 56.79; H, 6.99; N, 7.36%

EXAMPLE 45
5-(1S-(3,5-dicarboxyphenylaminocarbonyl)-2-phenylethylaminocarbonyl)-6-(1-adamantanemethylaminocarbonyl)-N-phenylsulphonyl-indole The material was prepared essentially as in example 44 except that phenylsulphonyl chloride was used instead of acetyl choride, $^1$H NMR ($d^6$-DMSO) δ 13.3 (2H, br s), 10.1 (1H, 2×s), 9.2 and 8.9 (1H, 2×d), 8.7–8.6 (3H, m), 8.2 (2H, s), 8.0 (2H, m), 7.9–7.1 (10H, m), 6.9 (1H, m), 4.7 (1H, m), 3.5–2.9 (4H, m), 1.9 (3H, m), 1.6 (6H, m), 1.5 (6H, m).

The compound was further characterised and tested as the di-N-methyl-D-glucamine salt found: C, 55.23; H, 6.88; N, 6.72. $C_{58}H_{76}N_6O_{19}S.4.0H_2O$ requires C, 56.07; H, 6.69; N, 6.64%

EXAMPLE 46
5-(1S-(3,5-dicarboxyphenylaminocarbonyl)-2-phenylethylaminocarbonyl)-6-(2,2-dimethylpropylaminocarbonyl)-indole and regioisomer with substituents at positions 5 and 6 reversed The material was prepared essentially as in example 24 except that 2,2-dimethyl-propylamine was used in step g instead of 1-adamantanemethylamine and that the regioisomers were not separated at the end of step h, $^1$H NMR ($d^6$-DMSO) δ 11.5 (1H, s), 10.3 and 10.2 (1H, 2×s), 8.7 (3H, m), 8.5 (1H, m), 8.2 (1H, s), 7.8 and 7.7 (1H, 2×s), 7.5–7.0 (7H, m), 6.5 (1H, m), 4.7 (1H, m), 3.2–2.9 (4H, m), 0.8 (9H, s)

The compound was further characterised and tested as the di-N-methyl-D-glucamine salt found: C, 53.21; H, 7.12; N, 8.08. $C_{46}H_{66}N_6O_{17}.3.5H_2O$ requires C, 53.19; H, 7.09; N, 8.09%

EXAMPLE 47
5-(1S-(3,5-dicarboxyphenylaminocarbonyl)-2-phenylethylaminocarbonyl)-6-(1-adamantanemethylaminocarbonyl)-indole The material was prepared essentially as in example 24 except that 1S-(3,5-dibenzyloxycarbonylphenylaminocarbonyl)-ethylamine was used in step h instead of 1S-(3,5-dibenzyloxycarbonylphenylaminocarbonyl)-2-phenylethylamine. The less polar regioisomer after this step was taken through to the title compound by hydrogenation. The 1S-(3,5-dibenzyloxycarbonylphenylaminocarbonyl)-ethylamine was prepared essentially as in example 15 steps c and d except that BOC-L-alanine was used in step c instead of BOC-L-phenylalanine. $^1$H NMR ($d^6$-DMSO) δ 11.5 (1H, s), 10.1 (1H, s), 8.7 (3H, m), 8.5 (1H, m), 8.2 (1H, s), 7.7 (1H, s), 7.6 (1H, s), 7.5 (1H, s), 6.5 (1H, s), 4.5 (1H, m), 2.9 (2H, m), 1.8 (3H, s), 1.5 (15H, m).

The compound was further characterised and tested as the di-N-methyl-D-glucamine salt found: C, 53.04; H, 7.26; N, 8.05. $C_{46}H_{68}N_6O_{17}.3.6H_2O$ requires C, 53.05; H, 7.27; N, 8.06%

EXAMPLE 48
6-(1S-(3,5-dicarboxyphenylaminocarbonyl)-2-phenylethylaminocarbonyl)-5-(1-adamantanemethylaminocarbonyl)-indole The material was prepared essentially as in example 47 except that the more polar regioisomer after this step was taken through to the title compound by hydrogenation, $^1$H NMR ($d^6$-DMSO) δ 11.5 (1H, s), 10.2 (1H, s), 8.7 (3H, m), 8.4 (1H, m), 8.2 (1H, s), 7.9 (1H, s), 7.5 (2H, m), 6.6 (1H, s), 4.5 (1H, m), 2.9 (2H, m), 1.8 (3H, s), 1.5 (15H, m).

The compound was further characterised and tested as the di-N-methyl-D-glucamine salt found: C, 56.32; H, 7.27; N, 8.42. $C_{46}H_{68}N_6O_{17}$ requires C, 56.55; H, 7.02; N, 8.60%

EXAMPLE 49
5-(1S-(trans 3,4-dimethoxycarbonylpyrrolidinocarbonyl)-2-phenylethylaminocarbonyl)-6-(1-adamantanemethylaminocarbonyl)-indole and regioisomer with substituents at 10 positions 5 and 6 reversed The material was prepared essentially as in example 24 except that 1S-(trans 3,4-dimethoxycarbonylpyrrolidinocarbonyl)-2-phenylethylamine was used in step h instead of 1S-(3,5-dibenzyloxycarbonylphenylaminocarbonyl)-2-phenylethyl amine. The mixture of regioisomers was not separated and no hydrogenation was performed as a final step as no deprotection was required. $^1$H NMR ($d^6$-DMSO) δ 11.4 (1H, m), 9.9 (0.5H, m), 8.6 (0.5H, m), 8.2 (1H, m), 7.7–7.1 (8H, m), 6.5 (1H, m), 4.8 and 4.6 (1H, 2×m), 3.6 (6H s), 3.2–2.9 (8H, m), 1.9 (3H, s), 1.8 (2H, t), 1.5 (6H, m), 1.4 (6H, m).

EXAMPLE 50
5-(1S-(trans 3,4-dicarboxypyrrolidinocarbonyl)-2-phenylethylaminocarbonyl)-6-(1-adamantanemethylaminocarbonyl)-indole and regioisomer with substituents at positions 5 and 6 reversed The material of example 49 (200 mg, 0.3 mmol) was dissolved in a 1:1 mixture of methanol and water (10 ml) and lithium hydroxide (28 mg, 0.6 mmol) was added. The temperature of the reaction vessel was raised to 80° for two minutes and on cooling the reaction mixture was evaporated and acidified to pH3 with 2M hydrochloric acid. The precipitated material was filtered and dried to leave the title compound (44 mg), $^1$H NMR ($d^6$-DMSO) δ 12.7 (2H, br s), 11.4 (1H, m), 8.6 (1H, m), 8.2 (1H, m), 7.7–7.1 (8H, m), 6.5

(1H, m), 4.8 (1H, m), 3.2–2.9 (8H, m), 1.9 (5H, m), 1.5 (6H, m), 1.4 (6H, s).

The compound was further characterised and tested as the di-N-methyl-D-glucamine salt found: C, 58.27; H, 7.38; N, 8.06. $C_{50}H_{74}N_6O_{17}$ requires C, 58.24; H, 7.23; N, 8.15%

EXAMPLE 51
3-(1S-(3,5-dicarboxyphenylaminocarbonyl)-2-phenylethylaminocarbonyl)-2-(1-adamantanemethylaminocarbonyl)-carbazole This was prepared essentially as in example 24 except that the dimethyl ester of carbazole-2,3-dicarboxylic acid was used in step e instead of the dimethyl ester of indole-5,6-dicarboxylic acid. The carbazole substrate was made as in J.Chem.Res., 1990, 1919. $^1$H NMR ($d^6$-DMSO) δ 13.2 (2H, br s), 11.6 (1H, s), 10.2 (1H, s), 8.8 (1H, d), 8.7 (2H, s), 8.6 (1H, t), 8.2 (1H, s), 8.0 (1H, d), 7.7 (1H, s), 7.6 (1H, t), 7.5–7.3 (7H, m), 7.2 (1H, t), 4.8 (1H, m), 3.4 and 3.0 (4H, m), 1.9 (3H, s), 1.5 (6H, m), 1.4 (6H, s).

EXAMPLE 52
2-(1S-(3,5-dicarboxyphenylaminocarbonyl)-2-phenylethylaminocarbonyl)-3-(1-adamantanemethylaminocarbonyl)-carbazole This was prepared essentially as in example 26 except that the dimethyl ester of carbazole-2,3-dicarboxylic acid was used in step e instead of the dimethyl ester of indole-5,6-dicarboxylic acid. The carbazole substrate was made as in J.Chem.Res., 1990, 1919. $^1$H NMR ($d^6$-DMSO) δ 11.7 (1H, s), 10.3 (1H, s), 9.0 (1H, d), 8.7 (2H, s), 8.5 (1H, t), 8.2 (1H, m), 7.9 (1H, s), 7.6–7.3 (8H, m), 7.0 (1H, s), 4.8 (1H, m), 2.8 and 2.5 (4H, m), 1.9 (3H, s), 1.5 (6H, m), 1.3 (6H, s).

EXAMPLE 53
3-(1S-(3,5-dicarboxyphenylaminocarbonyl)-2-phenylethylaminocarbonyl)-2-(1-adamantanemethylaminocarbonyl)-5,7-diacetoxy-naphthalene, arbitrary assignment of regioisomers at positions 2 and 3.

This was prepared essentially as in example 24 except that 5,7-diacetoxy-naphthalene-2,3-dicarboxylic acid anhydride was used in step f instead of indole-5,6-dicarboxylic acid anhydride. The naphthalene substrate was made in several steps from naphthalene-2,3-dicarboxylic acid. $^1$H NMR ($d^6$-acetone) δ 10.2 (1H, s), 9.0 (2H, s), 8.6–8.1 (3H, m), 7.6–7.1 (9H, m), 5.0 (1H, m), 3.2 (4H, m), 2.4 (6H, dd), 1.8 (3H, s), 1.6 (12H, m).

The compound was further characterised and tested as the di-N-methyl-D-glucamine salt found: C, 55.31; H, 6.62; N, 5.64. $C_{58}H_{77}N_5O_{22}$.4.1 $H_2O$ requires C, 55.54; H, 6.85; N, 5.58%

EXAMPLE 54
2-(1S-(3,5-dicarboxyphenylaminocarbonyl)-2-phenylethylaminocarbonyl)-3-(1-adamantanemethylaminocarbonyl)-5,7-diacetoxy-naphthalene, arbitrary assignment of regioisomers at positions 2 and 3.

This was prepared essentially as in example 26 except that 5,7-diacetoxy-naphthalene-2,3-dicarboxylic acid anhydride was used in step f instead of indole-5,6-dicarboxylic acid anhydride. The naphthalene substrate was made in several steps from naphthalene-2,3-dicarboxylic acid. $^1$H NMR ($d^6$-acetone) δ 10.2 (1H, s), 9.0 (2H, s), 8.6–8.1 (3H, m), 7.6–7.1 (9H, m), 5.0 (1H, m), 3.2 (4H, m), 2.4 (6H, m), 1.8 (3H, s), 1.6 (12H, m).

The compound was further characterised and tested as the di-N-methyl-D-glucamine salt found: C, 53.14; H, 6.75; N, 5.61. $C_{58}H_{77}N_5O_{21}$.6.9 $H_2O$ requires C, 53.40 H, 7.02; N, 5.40%

EXAMPLE 55
3-(1S-(3,5-dicarboxyphenylaminocarbonyl)-2-phenylethylaminocarbonyl)-2-(1-adamantanemethylaminocarbonyl)-5-nitronaphthalene and its regioisomer with groups at positions 2 and 3 reversed.

This was prepared essentially as in example 24 except that 5-nitronaphthalene-2,3-dicarboxylic acid anhydride was used in step f instead of indole-5,6-dicarboxylic acid anhydride and no attempt was made to separate the regioisomers in step h. The naphthalene substrate was made in several steps from naphthalene-2,3-dicarboxylic acid. The deprotection of the dibenzyl ester without reduction of the nitro group was performed using phase transfer hydrogenation over 10% palladium on charcoal using formic acid as a source of hydrogen. $^1$H NMR ($d^6$-DMSO) δ 10.2 (1H, 2×s), 9.0 and 8.8 (1H, 2×d), 8.6–8.0 (4H, m), 7.6–7.1 (10H, m), 4.7 (1H, m), 3.2 (4H, m), 1.8 (3H, s), 1.5 (12H, m).

The compound was further characterised and tested as the di-N-methyl-D-glucamine salt found: C, 51.97; H, 6.70; N, 6.12. $C_{54}H_{72}N_6O_{19}$.3.5 $H_2O$. 3.5 HCOOH requires C, 51.80; H, 6.50; N, 6.30%

EXAMPLE 56
3-(1S-(3,5-dicarboxyphenylaminocarbonyl)-2-phenylethylaminocarbonyl)-2-(1-adamantanemethylaminocarbonyl)-1-phenylnaphthalene and its regioisomer with groups at positions 2 and 3 reversed.

This was prepared essentially as in example 24 except that 1-phenylnaphthalene-2,3-dicarboxylic acid anhydride was used in step f instead of indole-5,6-dicarboxylic acid anhydride and no attempt was made to separate the regioisomers in step h. The naphthalene substrate was made from 2-phenylpropiolic acid as described in J.Het.Chem., 1974, 11(5), 687–90. $^1$H NMR ($d^6$-DMSO) δ 10.1 (1H, s), 9.8 (1H, d), 9.4 (2H, s), 8.2 (1H, s), 8.0–7.0 (16H, m), 4.8 (1H, m), 3.1 (2H, m), 2.4 (2H, m), 1.6 (3H, s), 1.4 (6H, m), 0.9 (6H, s).

The compound was further characterised and tested as the N-methyl-D-glucamine salt found: C, 65.46; H, 6.89; N, 5.41. $C_{53}H_{60}N_4O_{12}$.1.7 $H_2O$ requires C, 65.23; H, 6.55; N, 5.74%

EXAMPLE 57
3-(1S-(3,5-dicarboxyphenylaminocarbonyl)-2-phenylethylaminocarbonyl)-2-(1-adamantanemethylaminocarbonyl)-1,2,3,4-tetrahydroisoquinoline a. —N-tert-butyloxycarbonyl-3-(1S-( 3,5-dibenzyloxycarbonylphenylaminocarbonyl)-2-phenylethylaminocarbonyl)-1,2,3,4-tetrahydroisoquinoline (±)—N-tert-butyloxycarbonyl-1,2,3,4-tetrahydroisoquinoline-3-carboxylic acid (831 mg, 3 mmol) was suspended in dichloromethane (30 ml) and diisopropylethylamine (1.56 ml, 9 mmol) and PyBOP (500 mg, 3 mmol) was added. After stirring for 5 min, 1S-(3,5-dibenzyloxycarbonylphenylaminocarbonyl)-2-phenylethylamine (prepared as indicated in example 15) (1.52 g, 3 mol) was added. After stirring the mixture for 2 h the organic solution was washed with 5% potassium hydrogensulphate solution (30 ml) and brine (30 ml) and dried over magnesium sulphate. The organic solution was filtered and evaporated to leave a gum that was purified by column chromatography (silica dichloromethane 85% and ethyl acetate 15%) to leave the title compound (1.87 g).

b. 3-(1S-(3,5-dibenzyloxycarbonylphenylaminocarbonyl)-2-phenylethylaminocarbonyl)-1,2,3,4-tetrahydroisoquinoline The product of step a (1.87 g) was treated with trifluoroacetic acid (20 ml) for 20 min. After evaporation the material was partitioned between 5% sodium hydrogencarbonate solution and ethyl acetate. The insoluble white solid formed was filtered off and dried in vacuo (0.92 g).

c. 3-(1S-(3,5-dibenzyloxycarbonylphenylaminocarbonyl)-2-phenylethylaminocarbonyl)-2-(1-adamantanemethylaminocarbonyl)-1,2,3,4-tetrahydroisoquinoline The product of step b (1.75 g, 2.6 mmol) was dissolved in dichloromethane (40 ml) and 1-adamantanemethylisocyanate (0.6 g, 3.1 mmol) was added. The solution was stirred at room temperature overnight. The solution was then washed with 2M hydrochloric acid and brine, dried and evaporated to leave a solid that was purified by recrystallisation from ethanol followed by column chromatography (silica dichloromethane 80% and ethyl acetate 20%) to leave the title compound.

d. 3-(1S-(3,5-dicarboxyphenylaminocarbonyl)-2-phenylethylaminocarbonyl)-2-(1-adamantanemethylaminocarbonyl)-1,2,3,4-tetrahydroisoquinoline This was prepared essentially as described in example 3 step b except that the product of step c was used as substrate instead of 3-(2R-benzyloxycarbonyl-pyrrolidino-carbonyl)-2-(1-adamantanemethylaminocarbonyl)-naphthalene. $^1$H NMR (d$^6$-DMSO) δ 10.1 (1H, 2×s), 8.5 (2H, 2×s), 8.3 and 7.8 (1H, 2×d), 8.2 (1H, s), 7.3–6.8 (9H, m), 6.5 and 6.4 (1H, 2×t), 4.7–4.2 (4H, m), 3.2–2.7 (6H, m), 1.8 (3H, m), 1.5 (6H, m), 1.3 (6H, m).

The compound was further characterised and tested as the di-N-methyl-D-glucamine salt found: C, 57.23; H, 7.42; N, 7.61. $C_{53}H_{76}N_6O_{17}$.2.5 $H_2O$ requires C, 57.13; H, 7.33; N, 7.54%

EXAMPLE 58

5-(1S-(3,5-dicarboxyphenylaminocarbonyl)-ethylaminocarbonyl)-6-(cycloheptanemethylaminocarbonyl)-indole and regioisomer with substituents at positions 5 and 6 reversed The material was prepared essentially as in example 42 except that 1S-(3,5-dibenzyloxycarbonylphenylaminocarbonyl)-ethylamine was used in step h instead of 1S-(3,5-dibenzyloxycarbonylphenylaminocarbonyl)-2-phenylethylamine and that no attempt was made to separate the regioisomers at the end of this stage. The 1S-(3,5-dibenzyloxycarbonylphenylaminocarbonyl)-ethylamine was prepared essentially as in example 15 steps c and d except that BOC-L-alanine was used in step c instead of BOC-L-phenylalanine. $^1$H NMR (d$^6$-DMSO) δ 11.5 (1H, s), 10.2 (1H, s), 8.7 (4H, m), 8.2 (1H, s), 7.6 (3H, m), 6.5 (1H, s), 4.5 (1H, m), 3.1 (2H, m), 1.6–1.0 (16H, m).

The compound was further characterised and tested as the di-N-methyl-D-glucamine salt found: C, 54.88; H, 7.16; N, 8.98. $C_{43}H_{66}N_6O_{17}$ requires C, 55.00; H, 7.09; N, 8.95%

EXAMPLE 59

5-(1R-(3,5-dicarboxyphenylaminocarbonyl)-ethylaminocarbonyl)-6-(cycloheptanemethylaminocarbonyl)-indole and regioisomer with substituents at positions 5 and 6 reversed The material was prepared essentially as in example 58 except that 1R-(3,5-dibenzyloxycarbonylphenylaminocarbonyl)-ethylamine was used in step h instead of 1S-(3,5-dibenzyloxycarbonylphenylaminocarbonyl)-ethylamine.

The 1R-(3,5-dibenzyloxycarbonylphenylaminocarbonyl)-ethylamine was prepared essentially as in example 15 steps c and d except that BOC-D-alanine was used in step c instead of BOC-L-phenylalanine. $^1$H NMR (d$^6$-DMSO) δ 11.5 (1H, s), 10.2 (1H, s), 8.7 (4H, m), 8.2 (1H, s), 7.6 (3H, m), 6.5 (1H, s), 4.5 (1H, m), 3.1 (2H, m), 1.6–1.0 (16H, m).

The compound was further characterised and tested as the di-N-methyl-D-glucamine salt found: C, 52.76; H, 7.24; N, 8.60. $C_{43}H_{66}N_6O_{17}$.2H$_2$O requires C, 52.96; H, 7.24; N, 8.62%

EXAMPLE 60

5-(1S-(3,5-dicarboxyphenylaminocarbonyl)-2-(4-hydroxyphenyl)ethylaminocarbonyl)-6-(1-adamantanemethylaminocarbonyl)-benzimidazole This was prepared essentially as in example 25 except that 1S-(3,5-dibenzyloxycarbonyl-phenylaminocarbonyl)-2-(4-hydroxyphenyl)ethylamine was used in step d instead of 1S-(3,5-dibenzyloxycarbonylphenylaminocarbonyl)-2-phenylethylamine. The 1S-(3,5-dibenzyloxycarbonylphenylaminocarbonyl1)-2-(4-hydroxyphenyl)ethylamine was prepared as outlined in example 30. $^1$H NMR (d$^6$-DMSO) δ 13.0 (3H, br s), 10.2 (1H, s), 9.3 (1H, br s), 8.8 (1H, d), 8.7 (2H, s), 8.5 (1H, t), 8.4 (1H, s), 8.2 (1H, s), 7.9 (1H, s), 7.2 (1H, s), 7.1 (2H, d), 6.7 (2H, d), 4.6 (1H, m), 3.0–2.3 (4H, m), 1.8 (3H, s), 1.6 (6H, m), 1.4 (6H, m).

The compound was further characterised and tested as the di-N-methyl-D-glucamine salt found: C, 56.79; H, 6.75; N, 8.98. $C_{51}H_{71}N_7O_{18}$ requires C, 57.24; H, 6.69; N, 9.16%

EXAMPLE 61

5-(1R-(3,5-dicarboxyphenylaminocarbonyl)-2-phenylethylaminocarbonyl)-6-(1-adamantanemethylaminocarbonyl)-benzimidazole This was prepared essentially as in example 25 except that 1R-(3,5-dibenzyloxycarbonyl-phenylaminocarbonyl)-2-phenylethylamine was used in step d instead of 1S-(3,5-dibenzyloxycarbonylphenylaminocarbonyl)-2-phenylethylamine. The 1R-(3,5-dibenzyloxycarbonylphenylaminocarbonyl)-2-phenylethylamine was prepared as outlined in example 29. $^1$H NMR (d$^6$-DMSO) δ 13.0 (3H, br s), 10.2 (1H, s), 8.9 (1H, d), 8.7 (2H, s), 8.5 (1H, t), 8.4 (1H, s), 8.2 (1H, s), 7.9 (1H, s), 7.4 (5H, m), 7.1 (1H, s), 4.7 (1H, m), 3.5–2.6 (4H, m), 1.8 (3H, s), 1.4 (12H, m).

The compound was further characterised and tested as the di-N-methyl-D-glucamine salt found: C, 54.96; H, 7.33; N, 8.83. $C_{51}H_{71}N_7O_{17}$.3.5H$_2$O requires C, 54.79; H, 7.04; N, 8.77%

EXAMPLE 62

5-(1S-(3,5-dicarboxyphenylaminocarbonyl)-2-phenylethylaminocarbonyl)-6-(1-cycloheptanemethylaminocarbonyl)-benzimidazole The material was prepared essentially as in example 25 except that cycloheptanemethylamine was used in step c instead of 1-adamantanemethylamine, $^1$H NMR (d$^6$-DMSO) δ 13.2 (2H, br s), 12.8 (1H, br s), 10.2 (1H, s), 8.9 (1H, d), 8.7 (2H, s), 8.6 (1H, t), 8.4 (1H, s), 8.2 (1H, s), 8.0 (1H, m), 7.4 (5H, m), 7.1 (1H, s), 4.7 (1H, m), 3.5–2.9 (4H, m), 1.7–1.4 (13H, m).

The compound was further characterised and tested as the di-N-methyl-D-glucamine salt found: C, 56.48; H, 6.73; N, 9.40. $C_{48}H_{69}N_7O_{17}$.requires C, 56.74; H, 6.84; N, 9.65%

EXAMPLE 63

5-(1S-(3,5-dicarboxyphenylaminocarbonyl)-2-(2-fluorophenyl) ethylaminocarbonyl)-6-(1-adamantanemethylaminocarbonyl)-benzimidazole This was prepared essentially as in example 25 except that 1S-(3,5-dibenzyloxycarbonyl-phenylaminocarbonyl)-2-(2-fluorophenyl)ethylamine was used in step d instead of 1S-(3,5-dibenzyloxycarbonylphenylaminocarbonyl)-2-phenylethyl amine. The 1S-(3,5-dibenzyloxycarbonylphenylaminocarbonyl)-2-(2-fluorophenyl)ethylamine was prepared as outlined in example 27. $^1$H NMR (d$^6$-DMSO) δ 13.0 (3H, br s), 10.2 (1H, s), 8.9 (1H, d), 8.7 (2H, s), 8.6 (1H, t), 8.4 (1H, s), 8.2 (1H, s), 7.9 (1H, d), 7.4–7.2 (4H, m), 7.1 (1H, s), 4.8 (1H, m), 3.6–2.9 (4H, m), 1.8 (3H, s), 1.6 (6H, m), 1.3 (6H, m).

The compound was further characterised and tested as the di-N-methyl-D-glucamine salt found: C, 55.19; H, 6.77; N, 8.66. $C_{51}H_{70}FN_7O_{18}$ requires C, 55.10; H, 6.75; N, 8.82%

EXAMPLE 64

5-(1S-(3,5-dicarboxyphenylaminocarbonyl)-2-(4-aminophenyl)-ethylaminocarbonyl)-6-(1-adamantanemethylaminocarbonyl)-benzimidazole This was prepared as outlined in example 31 except that benzimidazole-5,6-dicarboxylic acid anhydride was used as substrate in step g instead of indole-5,6-dicarboxylic acid anhydride and there was no need to separate any regioisomers as these could not arise in this reaction. $^1$H NMR (d$^6$-DMSO) δ 12.8 (1H, br s), 10.2 (1H, s), 8.8 (1H, d), 8.7 (2H, s), 8.5 (1H, t), 8.4 (1H, s), 8.2 (1H, s), 7.9 (1H, br s), 7.3 (1H, s), 7.0 (2H, d), 6.6 (2H, d), 4.6 (1H, m), 3.3–2.8 (4H, m), 1.9 (3H, s), 1.6 (6H, m), 1.2 (6H, m).

The compound was further characterised and tested as the N-methyl-D-glucamine salt found: C, 56.83; H, 6.49; N, 10.79. $C_{44}H_{55}N_7O_{12}$.3.0 $H_2O$ requires C, 57.04; H, 6..62; N, 11.22%

EXAMPLE 65

5-(1S-(3,5-dicarboxyphenylaminocarbonyl)-5-aminopentylaminocarbonyl)-6-(1-adamantanemethylaminocarbonyl)-indole and regioisomer with substituents at positions 5 and 6 reversed This was prepared essentially as in example 24 except that 1S-(3,5-dibenzyloxycarbonyl-phenylaminocarbonyl)-5-benzyloxycarbonylaminopentylamine was used in step h instead of 1S-(3,5-dibenzyloxycarbonylphenylaminocarbonyl)-2-phenylethylamine and the mixture of regioisomers formed during this step were not separated. The 1S-(3,5-dibenzyloxycarbonylphenylaminocarbonyl)-5-benzyloxycarbonylaminopentylamine was prepared essentially as in example 15 steps c and d except that α-BOC-ε-Z-lysine was used in step c instead of BOC-L-phenylalanine. $^1$H NMR (d$^6$-DMSO) δ 11.5 (1H, 2×s), 10.2 (1H, 2×s), 8.8–8.2 (4H, m), 7.9–7.2 (4H, m), 6.5 (1H, 2×s), 5.3 (1H, s), 5.0 (1H, s), 4.5 (1H, m), 3.2 (4H, m), 2.0–1.0 (21H, m).

The compound was further characterised and tested as the N-methyl-D-glucamine salt found: C, 60.36; H, 7.02; N, 9.98. $C_{42}H_{58}N_6O_{12}$ requires C, 60.13; H, 6.97; N, 10.02%

EXAMPLE 66

5-(1S-(3,5-diethoxycarbonylphenylaminocarbonyl)-2-phenylethylaminocarbonyl)-6-(1-adamantanemethylaminocarbonyl)-indole and regioisomer with substituents at positions 5 and 6 reversed This was prepared essentially as in example 24 except that 1S-(3,5-ethoxycarbonyl-phenylaminocarbonyl)-2-phenylethylamine was used in step h instead of 1S-(3,5-dibenzyloxycarbonylphenylaminocarbonyl)-2-phenylethylamine and the mixture of regioisomers formed during this step were not separated. No hydrogenation was required. 1S-(3,5-ethoxycarbonyl-phenylaminocarbonyl)-2-phenylethylamine was prepared as outlined in example 15 steps c and d except that 3,5-diethoxycarbonylaniline was used in step c instead of 3,5-dibenzyloxycarbonylaniline. found: C, 69.88; H, 6.59; N, 7.67. $C_{42}H_{46}N_4O_7$ requires C, 70.18; H, 6.45; N, 7.79% $^1$H NMR (d$^6$-DMSO) δ 11.5 (1H, s), 10.3 and 10.2 (1H, 2×s), 8.8 (3H, m), 8.5 (1H, t), 8.2 (1H, s), 7.9 and 7.7 (1H, 2×s), 7.5–7.2 (6H, m), 7.0 (1H, 2×s), 6.5 (1H, 2×s), 4.7 (1H, m), 4.4 (4H, q), 3.4 and 2.9 (4H, m), 1.8 (3H; s), 1.5 (6H, m), 1.4 (6H, s), 1.3 (6H, t).

EXAMPLE 67

5-(1S-(4-fluorophenylmethylaminocarbonyl)-2-phenylethylaminocarbonyl)-6-(1-adamantanemethylaminocarbonyl)-benzimidazole This was prepared essentially as in example 25 except that 1S-($^4$-fluorophenylmethylaminocarbonyl)-2-phenylethylamine was used in step d instead of 1S-(3,5-dibenzyloxycarbonylphenylaminocarbonyl)-2-phenylethylamine and no final deprotection step was required. The 1S-(4-fluorophenylmethylaminocarbonyl)-2-phenylethylamine was prepared by coupling BOC-L-phenylalanine NHS ester with 4-fluorobenzylamine in DME followed by treatment with trifluoroacetic acid. Found: C, 71.14; H, 6.43; N, 11.39. $C_{36}H_{38}FN_5O_3$ requires C, 71.15; H, 6.30; N, 11.52% $^1$H NMR (d$^6$-DMSO) δ 11.3 (1H, br s), 8.7 (2H, m), 8.5 (2H, br s), 7.8 (1H, s), 7.4–7.1 (10H, m), 4.6 (1H, m), 4.4 (2H, m), 3.4 (2H, m), 2.8 (2H, m), 1.9 (3H, s), 1.6 (6H, m), 1.4 (6H, s).

EXAMPLE 68

5-(1S-(4-fluorophenylaminocarbonyl)-2-phenylethylaminocarbonyl)-6-(1-adamantanemethylaminocarbonyl)benzimidazole This was prepared essentially as in example 25 except that 1S-(4-fluorophenylaminocarbonyl)-2-phenylethylamine was used in step d instead of 1S-(3,5-dibenzyloxycarbonylphenylaminocarbonyl)-2-phenylethyl amine and no final deprotection step was needed. The 1S-(4-fluorophenylaminocarbonyl)-2-phenylethylamine was prepared by coupling BOC-L-phenylalanine with 4-fluoroaniline using PyBrOP, followed by treatment with trifluoroacetic acid. Found: C, 70.62; H, 6.26; N, 11.75. $C_{35}H_{36}FN_5O_3$ requires C, 70.81; H, 6.11; N, 11.80% $^1$H NMR (d$^6$-DMSO) δ 12.8(1H, br s), 10.0 (1H, br s), 8.8 (1H, m), 8.6 (1H, br s), 8.4 (1H, s), 7.9 (3H, m), 7.8–5 7.1 (8H, m), 4.7 (1H, m), 3.5 (1H, m), 3.1 (1H, m), 2.9 (2H, m), 1.9 (3H, s), 1.6 (12H, m).

EXAMPLE 69

5-(1S-(3,5-dicarboxyphenylaminocarbonyl)-2-(2,4-imidazolyl)ethylaminocarbonyl)-6-(1-adamantanemethylaminocarbonyl)-benzimidazole This was prepared essentially as in example 25 except that 1S-(3,5-dibenzyloxycarbonylphenylaminocarbonyl)-2-(2,4-imidazolyl)ethylamine was used in step d instead of 1S-(3, 5-dibenzyloxycarbonylphenylaminocarbonyl)-2-phenylethyl amine. The 1S-(3,5-dibenzyloxycarbonylphenylaminocarbonyl)-2-(2,4-imidazolyl)ethylamine was prepared by coupling BOC-L-histidine (with the aromatic ring nitrogen protected with a BOM group) to 3,5-dibenzyloxycarbonylaniline using PyBrOP, followed by treatment with trifluoroacetic acid. $^1$H NMR (d$^6$-DMSO) δ 10.1(1H, br s), 8.8 (1H, m), 8.6 (2H, br s), 8.5 (1H, br s), 8.4 (1H, s), 8.2 (1H, s), 7.9 (1H, s), 7.6 (1H, s), 7.5 (1H, s), 6.9 (1H, s), 4.7 (1H, m), 3.2–3.0 (4H, m), 1.8 (3H, s), 1.5 (12H, m).

EXAMPLE 70

5-(1S-(3,5-dicarboxyphenylaminocarbonyl)-2-(2-fluorophenyl)ethylaminocarbonyl)-6-(cycloheptanemethylaminocarbonyl)-benzimidazole This was prepared essentially as in example 63 except that cycloheptanemethylamine was used instead of 1-adamantanemethylamine in step c, $^1$H NMR (d$^6$-DMSO) δ 13.0 (3H, br s), 10.2 (1H, br s), 8.9 (1H, d), 8.74 (2H, s), 8.7 (1H, t), 8.4 (1H, s), 8.2 (1H, s), 7.8 (1H, s), 7.5–7.1 (5H, m), 4.8 (1H, m), 3.5 (1H, m), 3.3–3.1 (3H, m), 1.6–1.1 (13H, m).

The compound was further characterised and tested as the di-N-methyl-D-glucamine salt. Found: C, 55.39; H, 6.85; N, 9.17. $C_{48}H_{68}FN_7O_{17}$ requires C, 55.75; H, 6.63; N, 9.48%

EXAMPLE 71

5-(1S-(3,5-dicarboxyphenylaminocarbonyl)ethylaminocarbonyl)-6-(1-adamantanemethylaminocarbonyl)-benzimidazole This was prepared essentially as in example 25 except that 1S-(3,5-dibenzyloxycarbonylphenylaminocarbonyl)-ethylamine was used in step d instead of 1S-(3,5-dibenzyloxycarbonylphenylaminocarbonyl)-2-phenylethylamine. The 1S-(3,5-dibenzyloxycarbonylphenylaminocarbonyl)-ethylamine was prepared by coupling BOC-L-alanine to 3,5-dibenzyloxycarbonylaniline using PyBrOP, followed by treatment with trifluoroacetic acid. $^1$H NMR (d$^6$-DMSO) δ 13.0 (3H, br s), 10.1(1H, br s), 8.8 (1H, d), 8.7 (2H, s), 8.5 (1H, t), 8.4 (1H, s), 8.2 (1H, s), 7.9 (1H, s), 7.7 (1H, s), 4.5 (1H, m), 3.0 (2H, m), 1.8 (3H, s), 1.6–1.1 (15H, m).

The compound was further characterised and tested as the di-N-methyl-D-glucamine salt. Found: C. 50.76; H, 7.23; N, 8.97. $C_{45}H_{67}N_7O_{17}$ requires C, 50.60; H, 7.27; N, 9.18%

EXAMPLE 72

5-(1S-(3,5-dicarboxyphenylaminocarbonyl)-ethylaminbcarbonyl)-6-(cycloheptanemethylaminocarbonyl)-benzimidazole This was prepared essentially as in example 71 except that cycloheptanemethylamine was used instead of 1-adamantanemethylamine in step c, $^1$H NMR (d$^6$-DMSO) δ 13.0 (3H, br s), 10.2 (1H, br s), 8.8 (1H, d), 8.7 (2H, s), 8.6 (1H, t), 8.4 (1H, s), 8.2 (1H, s), 7.9 (1H, s), 7.7 (1H, br s), 4.5 (1H, m), 3.1 (2H, m), 1.8–1.1 (16H, m).

The compound was further characterised and tested as the di-N-methyl-D-glucamine salt. Found: C, 51.34; H, 7.29; N, 9.89. $C_{42}H_{65}FN_7O_{17}$.2.5 $H_2O$ requires C, 51.25; H, 7.16; N, 9.96%

EXAMPLE 73

5-(1S-(3,5-dicarboxyphenyl-N-(methyl)aminocarbonyl)-2-phenylethylaminocarbonyl)-6-(1-adamantanemethylaminocarbonyl)-benzimidazole This was prepared essentially as in example 25 except that 1S-(3,5-dibenzyloxycarbonylphenyl-N-(methyl)-aminocarbonyl)-2-phenylethylamine was used in step d instead of 1S-(3,5-dibenzyloxycarbonylphenylaminocarbonyl)-2-phenylethylamine. The 1S-(3,5-dibenzyloxycarbonylphenyl-N-(methyl)-aminocarbonyl)-2-phenylethylamine was prepared by treatment of N-t-butyloxycarbonyl-1S-(3,5-dibenzyloxycarbonylphenylaminocarbonyl)-2-phenylethylamine sodium hydride and methyl iodide, followed by treatment with trifluoroacetic acid. $^1$H NMR (d$^6$-DMSO) δ 13.0 (3H, br s), 8.8 (1H, d), 8.4 (2H, s), 8.0 (3H, m), 7.7 (2H, m), 7.2 (3H, m), 6.9 (2H, s), 4.5 (1H, m), 3.3–2.8 (7H, m), 1.9 (3H, s), 1.6–1.4 (12H, m).

The compound was further characterised and tested as the di-N-methyl-D-glucamine salt. Found: C, 56.43; H, 7.25; N, 8.82. $C_{52}H_{73}N_7O_{17}$ requires C, 56.27; H, 7.05; N, 8.83%

EXAMPLE 74

N-methyl-5-(1S-(3,5-dicarboxyphenylaminocarbonyl)-2-phenylethylaminocarbonyl)-6-(1-adamantanemethylaminocarbonyl)-benzimidazole, mixture of regioisomers This was prepared essentially as in example 25 except that N-methyl-benzimidazole-5,6-dicarboxylic acid anhydride was used in step c instead of benzimidazole-5,6-dicarboxylic acid anhydride. This was prepared by treatment of dimethylbenzimidazole-5,6-dicarboxylate with sodium methoxide and methyl iodide, followed by saponification with potassium hydroxide, and anydride formation with acetic anhydride. $^1$H NMR (d$^6$-DMSO) δ 13.0 (2H, br s), 10.2 (1H, s), 8.8 (1H, m), 8.7 (2H, s), 8.6 (2H, m), 8.2 (1H, s), 8.0 and 7.9 (1H, 2×s), 7.4–7.0 (6H, m), 4.8 (1H, m), 3.9 (3H, 2×s), 3.6–2.5 (4H, m), 1.8 (3H, s), 1.6–1.4 (12H, m).

The compound was further characterised and tested as the di-N-methyl-D-glucamine salt. Found:. C, 55.64; H, 7.15; N, 8.81. $C_{52}H_{73}N_7O_{17}$.3$H_2O$ requires C, 55.65; H, 7.10; N, 8.74%

EXAMPLE 75

5-(1S-(3-carboxy-4-fluoro-phenylaminocarbonyl)-2-phenylethylaminocarbonyl)-6-(1-adamantanemethylaminocarbonyl)-benzimidazole This was prepared essentially as in example 25 except that 1S-(3-benzyloxycarbonyl-4-fluoro-phenylaminocarbonyl)-2-phenylethylamine was used in step d instead of 1S-(3,5-dibenzyloxycarbonylphenylaminocarbonyl)-2-phenylethyl amine. The 1S-(3-benzyloxycarbonyl-4-fluoro-phenylaminocarbonyl)-2-phenylethylamine was prepared by coupling BOC-L-phenylalanine with 3-benzyloxycarbonyl-4-fluoroaniline using PyBrOP, followed by treatment with trifluoroacetic acid. $^1$H NMR (d$^6$-DMSO) δ 13.2 (1H, br s), 12.8 (1H, br s), 10.1 (1H, s), 8.8 (1H, d), 8.6 (1H, t), 8.4 (2H, m), 8.1 (1H, m), 8.0 (1H, m), 7.4 (4H, s), 7.3 (2H, m), 7.1 (1H, br s), 4.5 (1H, m), 3.3–2.8 (4H, m), 1.9 (3H, s), 1.6–1.4 (12H, m).

The compound was further characterised and tested as the N-methyl-D-glucamine salt. Found: C, 59.00; H, 7.08; N, 8.55. $C_{43}H_{53}N_6O_{10}$.2.9 $H_2O$. 1.3 dioxan requires C, 56.27; H, 7.05; N, 8.83%

EXAMPLE 76

5-(2R-carboxymethylaminocarbonylpyrrolidinocarbonyl)-6-(1-adamantanemethylaminocarbonyl)-benzimidazole This was prepared essentially as in example 25 except that 2R-benzyloxycarbonylmethylaminocarbonylpyrrolidine was used in step d instead of 1S-(3,5-dibenzyloxycarbonylphenylaminocarbonyl)-2-phenylethylamine. $^1$H NMR (d$^6$-DMSO) δ 12.8 (1H, br s), 12.5 (1H, br s), 8.7–7.5 (5H, m), 4.5 (1H, m), 3.9 (1H, dd), 3.6 (2H, m), 3.3 (2H, m), 2.9 (1H, m), 2.1–1.5 (19H, m).

The compound was further characterised and tested as the N-methyl-D-glucamine salt. Found: C, 56.93; H, 7.42; N, 10.76. $C_{34}H_{50}N_6O_{10}$.1.4$H_2O$ requires C, 57.25; H, 7.48; N, 10.43%

EXAMPLE 77

5-(2S-(3,5-dicarboxyphenylaminocarbonyl)-pyrrolidinocarbonyl)-6-(1-adamantanemethylaminocarbonyl)-benzimidazole This was prepared essentially as in example 25 except that 2S-(3,5-dibenzyloxycarbonylphenylaminocarbonyl)-pyrrolidine was used in step d instead of 1S-(3,5-dibenzyloxycarbonylphenylaminocarbonyl)-2-phenylethyl amine. The 2S-(3,5-dibenzyloxycarbonylphenylaminocarbonyl)-pyrrolidine was prepared by coupling BOC-L-proline with 3,5-dibenzyloxycarbonylaniline using PyBrOP, followed by treatment with trifluoroacetic acid. $^1$H NMR (d$^6$-DMSO) δ 13.0 (3H, br s), 10.1 (1H, s), 8.7 (3H, m), 8.4 (1H, s), 8.2 (1H, s), 7.6 (1H, br s), 4.6 (1H, m), 3.7–3.1 (2H, m), 3.0 (2H, d), 2.3 and 2.1 (2H, m), 1.8 (3H, s), 1.7–1.4 (12H, m).

The compound was further characterised and tested as the di N-methyl-D-glucamine salt. Found: C, 56.93; H, 7.42; N, 10.76. $C_{47}H_{69}N_7O_{17}$·1.4 $H_2O$. requires C, 57.25; H, 7.48; N, 10.43%

EXAMPLE 78

5-(1S-(2,5-dicarboxyphenylaminocarbonyl)-2-phenylethylaminocarbonyl)-6-(1-adamantanemethylaminocarbonyl)-benzimidazole This was prepared essentially as in example 25 except that 1S-(2,5-dibenzyloxycarbonylphenylaminocarbonyl)-2-phenylethyl amine was used in step d instead of 1S-(3,5-dibenzyloxycarbonylphenylaminocarbonyl)-2-phenylethyl amine. The 1S-(2,5-dibenzyloxycarbonylphenylaminocarbonyl)-2-phenylethyl amine was prepared by coupling FMOC-L-phenylalanine acid chloride with 2,5-dibenzyloxycarbonylaniline, followed by treatment with piperidine. $^1$H NMR (d$^6$-DMSO) δ 13.2 (2H, br s), 11.7 (1H, br s), 9.1 (1H, d), 9.0 (1H, s), 8.4 (1H, s), 8.0 (2H, m), 7.7 (3H, m), 7.4 (3H, m), 7.3 (2H, m), 7.2 (1H, m), 4.7 (1H, m), 3.4 (1H, dd), 3.1 (1H, dd), 2.8 (2H, m), 1.8 (3H, s), 1.6 (.6H, q), 1.4 (6H, m).

The compound was further characterised and tested as the di-N-methyl-D-glucamine salt. Found: C, 59.00; H, 7.08; N, 8.55. $C_{43}H_{53}N_6O_{10}$·2.9 $H_2O$. 1.3 dioxan requires C, 59.03; H, 7.11; N, 8.57%

EXAMPLE 79

5-(1S-(3-carboxyphenylaminocarbonyl)-2-phenylethylaminocarbonyl)-6-(1-adamantanemethylaminocarbonyl)-benzimidazole a. 5-(1S-(3-benzyloxycarbonylphenylaminocarbonyl)-2-phenylethylaminocarbonyl)-benzimidazole-6-carboxylic acid The product of example 25 step b (1.23 g, 6.5 mmol) and 1S-(3-benzyloxycarbonylphenylaminocarbonyl)-2-phenylethylamine (3.97 g, 6.5 mmol) were dissolved in acetonitirile (50 ml) and stirred and heated at reflux for 1 h. After cooling a yellow crystalline solid was formed which was isolated by filtration, washed with acetonitirile and dried to yield the title compound (3.65 g). The 1S-(3-benzyloxycarbonylphenylaminocarbonyl)-2-phenylethylamine had been prepared by coupling BOC-L-phenylalanine and 3-benzyloxycarbonylaniline in the presence of PyBROP followed by treatment with trifluoroacetic acid.

b. 5-(1S-(3-benzyloxycarbonylphenylaminocarbonyl)-2-phenylethylaminocarbonyl)-6-(1-adamantanemethylaminocarbonyl)-benzimidazole The product of step a (1.12 g, 2 mmol), 4-hydroxybenzotriazole (270 mg, 2 mmol), EDC (409 mg, 2 mmol), 1-adamantanemethylamine (495 mg, 3 mmol) and DMAP (20 mg) were dissolved in dry DMF (4 ml). After stirring overnight at room temperature the mixture was poured onto water (30 ml) and the resulting white precipitate was filtered and dried in vacuo to yield the title compound (1.51 g).

c. 5-(1S-(3-carboxyphenylaminocarbonyl)-2-phenylethylaminocarbonyl)-6-(1-adamantanemethylaminocarbonyl)-benzimidazole This was prepared essentially as in example 24 step i except that the benzyl ester prepared in step b above was used as substrate instead of the product of example 24 step h. $^1$H NMR (d$^6$-DMSO) δ 13.2 (2H, br s), 10.1 (1H, d), 8.9 (1H, d), 8.6 (2H, m), 8.4 (1H, s), 8.1 (1H, m), 7.9 (1H, s), 7.7 (1H, m), 7.4 (6H, m), 7.1 (1H, s), 4.8 (1H, m), 3.2–2.9 (4H, m), 1.9 (3H, s), 1.6 (6H, q), 1.4 (6H, m).

The compound was further characterised and tested as the N-methyl-D-glucamine salt. Found: C, 60.70; H, 6.92; N, 9.89. $C_{43}H_{54}N_6O_{10}$·2.0 $H_2O$ requires C, 60.69; H, 6.87; N, 9.88%

EXAMPLE 80

5-(1S-(3,5-ditetrazolylphenylaminocarbonyl)-2-phenylethylaminocarbonyl)-6-(1-adamantanemethylaminocarbonyl)-benzimidazole a. Bis pivaloyloxymethyl derivative of 1S-(3,5-ditetrazolylphenylaminocarbonyl)-2-phenylethylamine 5-nitro isophthalic acid was converted to 5-nitro-3-cyanobenzonitirle via the bis primary amide. Treatment with sodium azide in hot DMF gave the bis tetrazole which was derivatised with POM chloride. Catalytic hydrogenation of the nitro group gave the aniline, which was coupled with BOC-L-phenylalanine using PyBROP and treated with trifluoroacetic acid to leave the title compound.

b. Bis pivaloyloxymethyl derivative of 5-(1S-(3,5-ditetrazolylphenylaminocarbonyl)-2-phenylethylaminocarbonyl)-6-(1-adamantanemethylaminocarbonyl)-benzimidazol This was prepared essentially as in example 79 steps a and b but using the product of this example step a as substrate in step a instead of 1S-(3-benzyloxycarbonylphenylaminocarbonyl)-2-phenylethylamine c. 5-(1S-(3,5-ditetrazolylphenylaminocarbonyl)-2-phenylethylaminocarbonyl)-6-(1-adamantanemethylaminocarbonyl)-benzimidazole The bis POM derivative prepared in step b (890 mg) was dissolved in saturated methanolic ammonia solution (20 ml) and stirred at room temperature for 5 h. The volatile material was removed by evaporation to leave the title compound (740 mg) as its bis ammonium salt. Found: C, 57.36; H, 6.06; N, 27.17. $C_{37}H_{43}N_{15}O_3$·1.5 $H_2O$ requires C, 57.50; H, 5.99; N, 27.18% , $^1$H NMR (d$^6$-DMSO) δ 10.2 (1H, s), 8.8 (1H, d), 8.6 (2H, d), 8.4 (2H, m), 7.9 (1H, s3,7.4–7.2 (7H, m), 4.8 (1H, m), 3.5–3.0 (4H, m), 1.8 (3H, s), 1.5 (6H, q), 1.4 (6H, s).

EXAMPLE 81

5-(1S-(3,5-dimethoxycarbonylphenylaminocarbonyl)-2-phenylethylaminocarbonyl)-6-(1-adamantanemethylaminocarbonyl)-benzimidazole This was prepared essentially as in example 79 except that 1S-(3,5-dimethoxycarbonylphenylaminocarbonyl)-2-phenylethylamine was used in step a instead of 1S-(3-benzyloxycarbonylphenylaminocarbonyl)-2-phenylethylamine, $^1$H NMR (d$^6$-DMSO) δ 12.8 (1H, 2×s), 10.3 and 10.2 (1H, 2×s), 8.9 (1H, t), 8.8 (2H, s), 8.6 (1H, m), 8.4 (1H, s), 8.2 (1H, s), 8.0 and 7.8 (1H, 2×s), 7.3 (5H, m), 7.2 and 7.1 (1H, 2×s), 4.8 (1H, m), 3.9 (6H, s), 3.4 (1H, m), 3.0 (3H, m), 1.8 (3H, s), 1.6–1.4 (12H, m).

EXAMPLE 82
5-(1S-(2-methyl-5-carboxyphenylaminocarbonyl)-2-phenylethylaminocarbonyl)-6-(1-adamantanemethylaminocarbonyl)-benzimidazole This was prepared essentially as in example 79 except that 1S-(2-methyl-5-benzyloxycarbonylphenylaminocarbonyl)-2-phenyl ethylamine was used in step a instead of 1S-(3-benzyloxycarbonylphenylaminocarbonyl)-2-phenylethylamine, $^1$H NMR (d$^6$-DMSO) δ 12.8 (2H, s), 9.7(1H, m), 8.9 (1H, m), 8.5 (1H, s), 8.4 (1H, s), 8.0 (1H, m) 7.7 (2H, m) 7.3 (7H, m), 4.7 (1H, m), 3.4–2.7(4H, m), 2.3 (3H, s), 1.8 (3H, s), 1.6–1.4 (12H, m).

The compound was further characterised and tested as the N-methyl-D-glucamine salt. Found: C, 56.87; H, 6.89; N, 9.08. $C_{44}H_{56}N_6O_{10}$.5.2 H2O requires C, 57.23; H, 7.26; N, 9.10%

EXAMPLE 83
5-(1S-(3-tetrazolylphenylaminocarbonyl)-2-phenylethylaminocarbonyl)-6-(1-adamantanemethylaminocarbonyl)-benzimidazole This was prepared essentially as in example 79 except that the POM derivative of 1S-(3-tetrazolylphenylaminocarbonyl)-2-phenylethylamine was used in step a instead of 1S-(3-benzyloxycarbonylphenylaminocarbonyl)-2-phenylethylamine. The POM derivative of 1S-(3-tetrazolylphenylaminocarbonyl)-2-phenylethylamine was prepared essentially as in example 80 step a except that the synthetic manipulations were carried out using the commercially available 3-nitrobenzonitrile as starting material. The compound was isolated and tested as its ammonium salt. Found: C, 62.48; H, 6.42; N, 19.72. $C_{36}H_{40}N_{10}O_3$.1.8 H$_2$O requires C, 62.38; H, 6.34; N, 20.20% , $^1$H NMR (d$^6$-DMSO) δ 10.0 (1H, s), 8.8 (1H, d), 8.6 (1H, s), 8.5 (1H, t), 8.4 (1H, s), 7.9 (1H, s), 7.8 (1H, m), 7.7 (1H, d), 7.4–7.2 (7H, m), 4.8 (1H, m), 3.5–2.9 (4H, m), 1.9 (3H, s), 1.5 (6H, q), 1.4 (6H, s).

EXAMPLE 84
5-(1S-(3,5-ditetrazolylphenylaminocarbonyl)-2-(2-fluorophenyl)ethylaminocarbonyl)-6-(1-adamantanemethylaminocarbonyl)-benzimidazole This was prepared essentially as in example 80 except that BOC-L-2-fluorophenylalanine was used in step a instead of BOC-L-phenylalanine. The compound was isolated and tested as its bis ammonium salt. Found: C, 54.97; H, 5.92; N, 26.06. $C_{37}H_{42}FN_{15}O_3$.2.5 H$_2$O requires C, 54.94; H, 5.85; N, 25.97% $^1$H NMR (d$^6$-DMSO) δ 10.1 (1H, s), 8.8 (1H, d), 8.4 (5H, m), 7.9 (1H, s), 7.5 (1H, t), 7.4 (1H, t), 7.3 (3H, m), 4.8 (1H, m), 3.6–2.9 (4H, m), 1.8 (3H, s), 1.5 (6H, q), 1.4 (6H, s).

EXAMPLE 85
(±)-5-(1-(3,5-dicarboxyphenylaminocarbonyl)-2-(2,4-difluorophenyl)ethylaminocarbonyl)-6-(1-adamantanemethylaminocarbonyl)-benzimidazole This was prepared essentially as in example 79 except that (±)-1-(3,5-dibenzyloxycarbonylphenylaminocarbonyl)-2-(2,4-difluorophenyl)ethylamine was used in step a instead of 1S-(3-benzyloxycarbonylphenylaminocarbonyl)-2-phenylethylamine. (±)-1-(3,5-dibenzyloxycarbonylphenylaminocarbonyl)-2-(2,4-difluorophenyl)ethylamine was prepared by coupling BOC-2,4-difluorophenylalanine with 3,5-dibenzyloxycarbonylaniline using PyBrOP, followed by treatment with trifluoroacetic acid, $^1$H NMR (d$^6$-DMSO) δ 13.2 (3H, br s), 10.2 (1H, s), 8.9 (1H, d), 8.7 (2H, d), 8.6 (1H, t), 8.4 (1H, s), 8.2 (1H, t), 7.5 (1H, m), 7.3 (2H, m), 7.2 (1H, s), 7.1 (1H, m), 4.8 (1H, m), 3.5 (1H, dd), 3.0 (3H, m), 1.9 (3H, s), 1.6 (6H, q), 1.5 (6H, s).

The compound was further characterised and tested as the di-N-methyl-D-glucamine salt. Found: C, 52.83; H, 6.76; N, 8.26. $C_{51}H_{69}F_2N_7O_{17}$.4H$_2$O requires C, 52.67; H, 6.68; N, 8.43%

EXAMPLE 86
5-(1S-(3,5-dicarboxyphenylaminocarbonyl)-2-phenylethyl-(N-methylamino)-carbonyl)-6-(1-adamantanemethylaminocarbonyl)-benzimidazole This was prepared essentially as in example 79 except that 1S-(3,5-dibenzyloxycarbonylphenylaminocarbonyl)-2-phenyl ethyl-N-methylamine was used in step a instead of 1S-(3-benzyloxycarbonylphenylaminocarbonyl)-2-phenylethylamine. 1S-(3,5-dibenzyloxycarbonylphenylaminocarbonyl)-2-phenylethyl-N-methylamine was prepared by coupling BOC-N-methyl-L-phenylalanine with 3,5-dibenzyloxycarbonylaniline using PyBrOP, followed by treatment with trifluoroacetic acid.

The compound was further characterised and tested as the di-N-methyl-D-glucamine salt. Found: C, 55.69; H, 7.04; N, 8.65. $C_{52}H_{73}N_7O_{17}$.2H$_2$O requires C, 56.56; H, 7.03; N, 8.88%

EXAMPLE 87
5-(1S-(3,5-dicarboxyphenylaminocarbonyl)-2-(2-fluorophenyl)ethylaminocarbonyl)-6-(1-adamantanemethyl-aminocarbonyl)-indole This was prepared essentially as in example 26 except that the less polar regioisomer prepared in step h was used as the substrate in step i instead of the mixture used in example 26. $^1$H NMR (d$^6$-DMSO) δ 13.3 (2H, br s), 11.8 (1H, s), 10.2 (1H, s), 8.74 (1H, d), 8.7 (2H, s), 8.5 (1H, t), 8.2 (1H, s), 7.8 (1H, s), 7.6–7.2 (6H, m), 6.5 (1H, s), 4.8 (1H, m), 3.6 (1H, m), 3.0 (3H, m), 1.9 (3H, br s), 1.6 (12H, m).

The compound was further characterised and tested as the di-N-methyl-D-glucamine salt found: C, 55.55; H, 6.89; N, 7.61. $C_{52}H_{71}FN_6O_{17}$. 2.8 H$_2$O requires C, 55.67; H, 6.89; N, 7.49%

EXAMPLE 88
5-(1S-(3,5-dicarboxyphenylaminocarbonyl)-2-(2-fluorophenyl)ethylaminocarbonyl)-6-(1-adamantanemethylaminocarbonyl)-indole This was prepared essentially as in example 26 except that the more polar regioisomer prepared in step h was used as the substrate in step i instead of the mixture used in example 26. $^1$H NMR (d$^6$-DMSO) δ 13.3 (2H, br s), 11.5 (1H, s), 10.3 (1H, s), 8.8 (1H, d), 8.7 (2H, s), 8.4 (1H, t), 8.2 (1H, s), 7.9 (1H, s), 7.5–7.2 (5H, m), 7.0 (1H, s), 6.6 (1H, s), 4.8 (1H, m), 3.6 (1H, m), 3.0 (3H, m), 1.8 (3H, br s), 1.6 (12H, m).

The compound was further characterised and tested as the di-N-methyl-D-glucamine salt found: C, 55.27; H, 7.03; N, 7.49. $C_{52}H_{71}FN_6O_{17}$. 3.3 H$_2$O requires C, 55.22; H, 6.92; N, 7.43%

EXAMPLE 89
5-(2R-(1R-carboxyethylaminocarbonyl)pyrrolidinocarbonyl)-6-(1-adamantanemethylaminocarbonyl)-indole Mixture of regioisomers at positions 5 and 6

This was prepared essentially as in example 24 except that 2R-(1R-benzyloxycarbonylethylaminocarbonyl)pyrrolidine was used in step h instead of 1S-(3,5-dibenzyloxycarbonylphenylaminocarbonyl)-2-phenylethyl amine. $^1$H NMR (d$^6$-DMSO) δ 11.4 (1H, 2×s), 9.0–7.0 (6H, m), 6.5 (1H, 2×s), 4.5 and 4.2 (2H, 2×m), 3.6 (2H, m), 3.3 (2H, m), 2.9 (1H, m), 2.1–1.5 (20H, m).

The compound was further characterised and tested as the N-methyl-D-glucamine salt. Found: C, 54.22; H, 7.28; N, 6.48. $C_{36}H_{53}N_5O_{10}$.1.3 DCM. 2.8 dioxan requires C, 54.29; H, 7.33; N, 6.53%

EXAMPLE 90

5-(1S-(3-carboxyphenylaminocarbonyl)-2-phenylethylaminocarbonyl)-6-(1-adamantanemethylaminocarbonyl)-indole Mixture of regioisomers at positions 5 and 6

This was prepared essentially as in example 79 except that indole-5,6-dicarboxylic acid anhydride was used as substrate instead of benzimidazole-5,6-dicarboxylic acid anhydride in step a. $^1$H NMR (d$^6$-DMSO) δ 11.5 (1H, br s), 10.2 and 10.1 (1H, 2×s), 8.8 (1H, m), 8.5 (2H, m), 8.1 (1H, m), 7.9 and 7.7 (1H, 2×s), 7.7–7.4 (8H, m), 7.1 and 7.0 (1H, 2×s), 6.6 and 6.5 (1H, 2×s), 4.7 (1H, m), 3.5–2.9 (4H, m), 1.9 (3H, s), 1.6 (6H, q), 1.5 (6H, m).

The compound was further characterised and tested as the N-methyl-D-glucamine salt. Found: C, 61.67; H, 7.11; N, 7.90. $C_{44}H_{55}N_5O_{10}$.2.5 $H_2O$ requires C, 61.52; H, 7.04; N, 8.15%

EXAMPLE 91

2S-(1R-(carboxymethylaminocarbonyl)-2-phenylethylaminocarbonyl)-6-(1-adamantanemethylaminocarbonyl)-indole Mixture of regioisomers at positions 5 and 6

This was prepared essentially as in example 90 except that the benzyl ester of D-phenylalanyl-glycine was used as substrate instead of 1S-(3-benzyloxycarbonylphenylaminocarbonyl)-2-phenylethylamine in step a. $^1$H NMR (d$^6$-DMSO) δ 11.4 (1H, 2×s), 8.6 (1H, m), 8.5 (1H, m), 8.3 (1H, m), 7.8 and 7.6 (1H, 2×s), 7.5–7.1 (7H, m), 6.6 and 6.5 (1H, 2×s), 4.6 (1H, m), 3.9–2.9 (6H, m), 1.9 (3H, s), 1.6 (6H, q), 1.5 (6H, m).

The compound was further characterised and tested as the N-methyl-D-glucamine salt. Found: C, 52.75; H, 7.77; N, 7.52. $C_{39}H_{55}N_5O_{10}$.7.5 $H_2O$ requires C, 52.81; H, 7.73; N, 7.89%

EXAMPLE 92

5-(1S-(3,5-di-methylsulphonylaminophenylaminocarbonyl)-2-phenylethylaminocarbonyl)-6-(1-adamantanemethylaminocarbonyl)-indole Mixture of regioisomers at positions 5 and 6 a. 1S-(3,5-di-methylsulphonylaminophenylaminocarbonyl)-2-phenylethylamine

This was prepared by in several steps by coupling BOC-L-phenylalaninemethyl ester with 3,5-dinitroaniline using trimethylaluminium in toluene, followed by catalytic hydrogenation to yield the bis aniline. Treatment with methanesulphonic anhydride and subsequent deprotection with TFA gave the title compound.

b. 5-(1S-(3,5-di-methylsulphonylaminophenylaminocarbonyl)-2-phenylethylaminocarbonyl)-6-(1-adamantanemethylaminocarbonyl)-indole Mixture of regioisomers at positions 5 and 6

The title compound was prepared essentially as in example 24 step h except that the product of step a above was used as substrate rather than 1S-( 3,5-dibenzyloxycarbonylphenylaminocarbonyl)-2-phenylethylamine. $^1$H NMR (d$^6$-DMSO) δ 11.5 (1H, br s), 10.1 and 10.0 (1H, 2×s), 8.7 (1H, dd), 8.3 (1H, m), 8.1–6.5 (14H, m), 4.8 (1H, m), 3.5 (6H, s), 3.5–3.0 (4H, m), 1.9 (3H, s), 1.6 (6H, q), 1.5 (6H, m)

EXAMPLE 93

5-(1S-(3,5-di-trifluoromethylsulphonylaminophenylaminocarbonyl)-2-phenylethylaminocarbonyl)-6-(1-adamantanemethylaminocarbonyl)-indole Mixture of regioisomers at positions 5 and 6

This was prepared essentially as in example 92 except that trifluoromethanesulphonic anhydride was used in the course of step a instead of methanesulphonic anhydride Found: C, 51.34; H, 4.48; N, 9.49. $C_{18}H_{18}F_6N_6O_7S_2$.1.1 $H_2O$ requires C, 51.41 H, 4.55; N, 9.47% $^1$H NMR (d$^6$-DMSO) δ 11.5 (1H, br s), 10.1 (1H, 2×s), 8.7 (1H, m), 8.4 (1H, m), 8.1–6.5 (14H, m), 4.7 (1H, m), 3.5–2.7 (4H, m), 1.9 (3H, s), 1.6 (6H, q), 1.5 (6H, m).

EXAMPLE 94

5-(1S-(3,5-di-trifluoromethylcarbonylaminophenylaminocarbonyl)-2-phenylethylaminocarbonyl)-6-(1-adamantanemethylaminocarbonyl)-indole Mixture of regioisomers at positions 5 and 6

This was prepared essentially as in example 92 except that trifluoroacetic anhydride was used in the course of step a instead of methanesulphonic anhydride Found: C, 54.26; H, 5.66; N, 9.29. $C_{40}H_{38}F_6N_6O_5$.5 $H_2O$ requires C, 54.13 H, 5.46; N, 9.47% $^1$H NMR (d$^6$-DMSO) δ 11.5 (1H, br s), 11.4 (2H, br s), 10.2 (1H, 2×s), 8.7 (1H, m), 8.5 (1H, m), 8.1–6.5 (12H, m), 4.8 (1H, m), 3.5–2.8 (4H, m), 1.8 (3H, s), 1.6 (6H, q), 1.5 (6H, m).

EXAMPLE 95

5-(1S-(3,5-di-tert-butylaminosulphonylphenylaminocarbonyl)-2-phenylethylaminocarbonyl)-6-(1-adamantanemethylaminocarbonyl)-indole Mixture of regioisomers at positions 5 and 6 a. 1S-(3,5-di-tert-butylaminosulphonylphenylaminocarbonyl)-2-phenylethylamine

This was prepared in several steps starting with benzene-1,3-disulphonyl chloride. This was nitrated with oleum in nitric acid to give the 5-nitro-1,3-bis sulphonic acid derivative. This was converted to the bis sulphonyl chloride compound with phosphorus pentachloride, and then reacted with tert-butylamine to give the bis tert-butylsulphonamide. Hydrogenation, followed by coupling with Z-L-phenylalanine using PyBROP, gave the title compound as a Z-protected derivative. This was converted to the title compound by hydrogenation.

b. 5-(1S-(3,5-di-tert-butylaminosulphonylphenylaminocarbonyl)-2-phenylethylaminocarbonyl)-6-(1-adamantanemethylaminocarbonyl)-indole Mixture of regioisomers at positions 5 and 6

The title compound was prepared essentially as in example 24 step h except that the product of step a above was used as substrate rather than 1S-(3,5-dibenzyloxycarbonylphenylaminocarbonyl)-2-phenylethylamine. Found: C, 54.39; H, 6.22; N, 8.07. $C_{44}H_{56}N_6O_7S_2$. 2 DCM. 0.3 ethyl acetate requires C, 54.44 H, 6.04; N, 8.07% $^1$H NMR (d$^6$-DMSO) δ 11.4 (2H, m), 8.7 (1H, m), 8.4–6.5 (15H, m), 5.4 (1H, m), 3.1–2.6 (4H, m), 1.9 (3H, s), 1.6 (6H, q), 1.5 (6H, m), 1.1 (18H, m).

EXAMPLE 96

5-(1S-(3,5-di-aminosulphonylphenylaminocarbonyl)-2-phenylethylaminocarbonyl)-6-(1-adamantanemethylaminocarbonyl)-indole Mixture of regioisomers at positions 5 and 6

The compound of example 95 (30 mg, 0.36 mmol) was treated with trifluoroacetic acid (1 ml) and allowed to stir for 24 h at room temperature. The solvent was removed by evaporation and theresidue was then azeotroped with toluene (3×1 ml). It was then taken up in dichloromethane (2 ml), and the residual solid that resulted was isolated by filtration, washed with diethyl ether and then dried to yield the title compound (21 mg), $^1$H NM (d$^6$-DMSO) δ 11.8 (1H, br s), 11.4 (2H, m), 8.7 (1H, m), 8.4–6.5 (16H, m), 4.8 (1H, m), 3.1–2.6 (4H, m), 1.9 (3H, m), 1.6 (6H, m), 1.5 (6H, m).

EXAMPLE 97

5-(1S-(3,5-ditetrazolylphenylaminocarbonyl)-2-(2-fluorophenyl)ethylaminocarbonyl)-6-(1-adamantanemethylaminocarbonyl)-indole This was prepared essentially as in example 84 except that indole-5,6-dicarboxylic anhydride was used in in step b instead of benzimidazole-5,6-dicarboxylic anhydride. After the anhydride opening step, the mixture of regioisomers formed was separated by chromatography (silica 5% methanol and 95% dichloromethane) and the more polar regioisomer was taken through the subsequent coupling with 1-adamantanemethylamine and deprotection. $^1$H NMR (d$^6$-DMSO) δ 11.5 (1H, s), 10.2 (1H, s), 8.7 (1H, d), 8.6 (2H, s), 8.4 (1H, s), 8.3(1H, t), 7.7 (1H, s), 7.5–7.0 (6H, m), 6.5 (1H, s), 4.8 (1H, m), 3.6–2.9 (4H, m), 1.8 (3H, s), 1.5 (6H, q), 1.4 (6H, s).

EXAMPLE 98

6-(1-(3,5-ditetrazolylphenylaminocarbonyl)-2-(2-fluorophenyl)ethylaminocarbonyl)-5-(1-adamantanemethylaminocarbonyl)-indole This was prepared essentially as in example 97 except that the less polar regioisomer following anhydride opening was used as substrate for subsequent transformatons. $^1$H NMR (d$^6$-DMSO) δ 11.5 (1H, s), 10.3 (1H, s), 8.8 (1H, d), 8.6 (2H, s), 8.4 (1H, s), 8.3(1H, t), 7.9 (1H, s), 7.5–7.0 (6H, m), 6.6 (1H, s), 4.8 (1H, m), 3.6–2.9 (4H, m), 1.8 (3H, s), 1.5 (6H, q), 1.4 (6H, s).

EXAMPLE 99

5-(1S-(3-trifluoroacetylaminosulphonylphenylaminocarbonyl)-2-phenylethylaminocarbonyl)-6-(1-adamantanemethylaminocarbonyl)-indole Mixture of regioisomers at positions 5 and 6 a. 1S-(3-trifluoroacetylaminosulphonylphenylaminocarbonyl)-2-phenylethylamine

This was prepared in several steps starting with nitrobenzene-3-sulphonyl chloride. This was converted into the sulphonamide using ammonia in benzene. Trfluoroacetic anhydride was used to introduce the trifluoroacetyl group onto the sulphonamide. Catalytic hydrogenation reduced the nitro group to an amino function and this material was coupled to BOC-L-phenylalananine using the PyBROP method. Removal of the BOC group was achieved with trifluoroacetic acid.

b. 5-(1S-(3,5-di-tert-butylaminosulphonylphenylaminocarbonyl)-2-phenylethylaminocarbonyl)-6-(1-adamantanemethylaminocarbonyl)-indole Mixture of regioisomers at positions 5 and 6

The title compound was prepared essentially as in example 24 step h except that the product of step a above was used as substrate rather than 1S-(3,5-dibenzyloxycarbonylphenylaminocarbonyl)-2-phenylethylamine. $^1$H NMR (d$^6$-DMSO) δ 11.5 (1.5H, m), 10.5–9.8 (1.5 H, m), 8.5–7.0 (14H, m), 6.6 and 6.5 (1H, 2×s), 4.8 (1H, m), 3.5–2.9 (4H, m), 1.9 (3H, s), 1.7 (6H, m), 1.5 (6H, m).

EXAMPLE 100

5-(1S-(3-tetrazolylphenylaminocarbonyl)-2-phenylethylaminocarbonyl)-6-(1-adamantanemethylaminocarbonyl)-indole This was prepared essentially as in example 83 except that indole-5,6-dicarboxylic acid anhydride was used as substrate rather than benzimidazole-5,6-dicarboxylic acid anhydride. After the anhydride opening step, the mixture of regioisomers formed was separated by chromatography (silica 5% methanol and 95% dichloromethane) and the more polar regioisomer was taken through the subsequent coupling with 1-adamantanemethylamine.

The compound was isolated and tested as its ammonium salt. Found: C, 64.58; H, 6.51; N, 18.01. $C_{37}H_{41}N_9O_3$.1.5 $H_2O$ requires C, 64.71; H, 6.46; N, 18.35%, $^1$H NMR (d$^6$-DMSO) δ 11.5 (1H, s), 10.1 (1H, s), 8.7 (1H, d), 8.6 (1H, s), 8.5 (1H, t), 7.9 (1H, d), 7.7 (2H, s), 7.5 (1H, t), 7.4–7.2 (7H, m), 6.5 (1H, s), 4.8 (1H, m), 3.5–2.9 (4H, m), 1.9 (3H, s), 1.6 (6H, q), 1.5 (6H, s).

EXAMPLE 101

6-(1S-(3-tetrazolylphenylaminocarbonyl)-2-phenylethylaminocarbonyl)-5-(1-adamantanemethylaminocarbonyl)-indole This was prepared essentially as in example 100 except that the less polar regioisomer following anhydride opening was used as substrate for subsequent transformations. Found: C, 64.74; H, 6.46; N, 18.07. $C_{37}H_{41}N_9O_3$.1.5 $H_2O$ requires C, 64.71; H, 6.46; N, 18.35%, $^1$H NMR (d$^6$-DMSO) δ 11.5 (1H, s), 10.1 (1H, s), 8.8 (1H, d), 8.6 (1H, s), 8.4 (1H, t), 7.9 (2H, m), 7.7 (1H, d), 7.5 (1H, t), 7.4–7.2 (7H, m), 6.6 (1H, s), 4.8 (1H, m), 3.5–2.9 (4H, m), 1.9 (3H, s), 1.6 (6H, q), 1.5 (6H, s).

EXAMPLE 102

5-(1S-(3-trifluoromethylsulphonylaminophenylaminocarbonyl)-2-phenylethylaminocarbonyl)-6-(1-adamantanemethylaminocarbonyl)-indole. Mixture of regioisomers at positions 5 and 6

This was prepared essentially as in example 93 except that 3-nitroaniline was used in the course of step a instead of 3,5-dinitroaniline, Found: C, 61.42; H, 5.58; N, 9.65. $C_{37}H_{38}F_3N_5O_5S$ requires C, 61.57 H, 5.31; N, 9.70% $^1$H NMR (d$^6$-DMSO) δ 11.7 (1H, br s), 11.5 (1H, s), 10.1 and 10.0 (1H, 2×s), 8.7 (1H, m), 8.5 (1H, m), 8.1 (1H, m), 7.9 and 7.8 (1H, 2×s), 7.8 (1H, m), 7.5 (1H, m), 7.4 (6H, m), 7.2–7.0 (2H, m), 6.6 and 6.5 (1H, 2×s), 4.7 (1H, m), 3.5–2.8 (4H, m), 1.9 (3H, s), 1.7 (6H, q), 1.5 (6H, m).

EXAMPLE 103

5-(1S-(3,5-dihydroxy-N-(methyl)aminocarbonylphenylaminocarbonyl)-2-phenylethylaminocarbonyl)-6-(1-adamantanemethylaminocarbonyl)-indole. Mixture of regioisomers at positions 5 and 6

This was prepared essentially as in example 24 except that 1S-(3,5-dibenzyloxy-N-(methyl)aminocarbonyl-phenylaminocarbonyl)-2-phenylethylamine was used in step h instead of 1S-(3,5-dibenzyloxycarbonylphenylaminocarbonyl)-2-phenylethyl amine and the mixture of regioisomers formed during this step were not separated $^1$H NMR (d$^6$-DMSO) δ 11.5 (1H, s), 10.1 (1H, s), 8.7 (1H, dd), 8.5 (1H, m), 8.2 (2H, s), 7.9 and 7.7 (1H, 2×s), 7.6–6.5 (9H, m), 6.5 (1H, s), 4.7 (1H, m), 3.5–2.7 (10H, m), 1.9 (3H, s), 1.6 (6H, m), 1.5 (6H, m).

EXAMPLE 104
5-(1S-(3,5-ditetrazolylphenylaminocarbonyl)-2-phenylethylaminocarbonyl)-6-(1-adamantanemethylaminocarbonyl)-indole This was prepared essentially as in example 97 except that L-phenylalanine was used in step a instead of L-2-fluorophenylalanine and the regioisomers were separated immediately prior to final deprotection by column chromatography (silica 75% dichloromethane 25% ethyl acetate). The less polar regioisomer was converted to the compound of this example. $^1$H NMR (d$^6$-DMSO) δ 11.5 (1H, s), 10.4 (1H, s), 8.8 (3H, m), 8.5 (2H, m), 7.7 (1H, s), 7.5 (1H, t), 7.4–7.0 (6H, m), 6.5 (1H, s), 4.8 (1H, m), 3.5–2.9 (4H, m), 1.8 (3H, s), 1.5 (6H, q), 1.3 (6H, s).

The compound was further characterised and tested as the N-methyl-D-glucamine salt

EXAMPLE 105
6-(1S-(3,5-ditetrazolylphenylaminocarbonyl)-2-phenylethylaminocarbonyl)-5-(1-adamantanemethylaminocarbonyl)-indole This was prepared essentially as in example 104 except that the more polar regioisomer isolated when regioisomers were separated was converted to the title compound. $^1$H NMR (d$^6$-DMSO) δ 11.5 (1H, s), 10.4 (1H, s), 8.8 (3H, m), 8.5 (2H, m), 7.9 (1H, s), 7.5 (1H, t), 7.4–7.0 (6H, m), 6.6 (1H, s), 4.8 (1H, m), 3.6–2.9 (4H, m), 1.8 (3H, s), 1.5 (6H, q), 1.3 (6H, s).

The compound was further characterised and tested as the N-methyl-D-glucamine salt

EXAMPLE 106
5-(1S-(3,5-di-(cis-4-phenyl-3,5-dioxacyclohexaneoxycarbonyl)-phenylaminocarbonyl)-2-phenylethylaminocarbonyl)-6-(1-adamantanemethylaminocarbonyl)-indole.

The product of example 24 (100 mg, 0.15 mmol) and cis-4-phenyl-3,5-dioxacyclohexanol (54 mg, 0.3 mmol) were dissolved in dichloromethane (20 ml) and DCCI (69 mg, 0.3 mmol) was added, followed by DMAP. The mixture was stirred overnight at room temperature and filtered to remove the DCU that had formed. Evaporation, followed by column chromatography (silica 50% ethyl acetate and 50% dichloromethane) followed by trituration with hexane and ethanol gave the title compound as a colorless solid (36 mg), $^1$H NMR (d$^6$-DMSO) δ 11.5 (1H, s), 10.4 (1H, s), 8.9 (2H, m), 8.8 (1H, d), 8.4 (2H, m), 7.8–6.5 (19H, m), 5.7 (2H, s), 5.0 (2H, s), 4.8 (1H, m), 4.3 (8H, q), 3.5–2.8 (4H, m), 1.8 (3H, s), 1.5 (6H, q), 1.4 (6H, m).

EXAMPLE 107
5-(1S-(3,5-di-(5-indanoloxycarbonyl)phenylaminocarbonyl)-2-phenylethylaminocarbonyl)-6-(1-adamantanemethyl-aminocarbonyl)-indole.

This material was prepared essentially as in example 106 except that 5-indanol was used instead of cis-4-phenyl-3,5-dioxacyclohexanol. Found: C, 73.48; H, 6.22; N, 6.17. $C_{56}H_{54}N_4O_7$ requires C, 73.52 H, 6.19; N, 6.12%, $^1$H NMR (d$^6$-DMSO) δ 11.5 (1H, s), 10.3 (1H, s), 9.0 (2H, d), 8.5 (1H, t), 8.4 (1H, t), 7.8 (1H, d), 7.7–6.5 (15H, m), 4.8 (1H, m), 3.6–2.8 (4H, m), 2.5 (12H, m), 1.8 (3H, S), 1.5 (6H, q), 1.4 (6H, m).

EXAMPLE 108
5-(1S-(3,5-dicarboxyphenylaminocarbonyl)-2-phenylethylaminocarbonyl)-6-(1-azabicyclo[2.2.2]oct-3-ylmethylaminocarbonyl)-indole a. 5-(1S-(3,5-dibenzyloxycarbonylphenylaminocarbonyl)-2-phenylethylaminocarbonyl)-indole-6-carboxylic acid.

Indole-5,6-dicarboxylic acid anhydride (1.87 g, 10.0 mmol) and 1S-(3,5-dibenzyloxycarbonylphenylaminocarbonyl)-2-phenylethyl amine (4.96 g, 9.8 mmol) were dissolved in acetonitirile (100 ml) and stirred and heated at reflux for 30 min. After cooling a yellow crystalline solid was formed which was isolated by filtration, washed with acetonitirile and dried to yield the title compound (3.25 g). This was mainly the regioisomer indicated in the title. The mother liquors when evaporated yielded mainly the other regioisomer. This was not used further in this example.

b. 5-(1S-(3,5-dibenzyloxycarbonylphenylaminocarbonyl)-2-phenylethylaminocarbonyl)-6-(1-azabicyclo[2.2.2]oct-3-ylmethylaminocarbonyl)-indole This was prepared essentially as in example 79 step b except that the product of step a above was used instead of the product of example 79 step a, and 1-azabicyclo[2.2.2]oct-3-ylmethylamine instead of 1-adamantanemethylamine.

c. 5-(1S-(3,5-dicarboxyphenylaminocarbonyl)-2-phenylethylaminocarbonyl)-6-(1-azabicyclo[2.2.2]oct-3-ylmethylaminocarbonyl)-indole This was prepared essentially as in example 24 step i except that the dibenzyl ester prepared in step b above was used as substrate instead of the product of example 24 step h. $^1$H NMR (d$^6$-DMSO) δ 11. 5 (1H, s), 10.1 (1H, 2×s), 8.7 (4H, m), 8.2 (1H, m), 7.7–6.5 (9H, m), 4.8 (1H, m), 3.6–2.7 (10H, m), 2.4–1.5 (6H, m).

The compound was further characterised and tested as the N-methyl-D-glucamine salt. Found: C, 55.61; H, 6.70; N, 9.40. $C_{42}H_{52}N_6O_{12}$ requires C, 55.74; H, 6.68; N, 9.29%

EXAMPLE 109
5-(1S-(3,5-dicarboxyphenylaminocarbonyl)-2-phenylethylaminocarbonyl)-6-(4-hydroxycyclohexanemethylaminocarbonyl)-indole Isomer 1 (unknown whether hydroxy group is cis or trans to the methylaminocarbonyl group)

This was prepared essentially as in example 108 except that 4-benzyloxycyclohexanemethylamine was used in step b instead of 1-azabicyclo[2.2.2]oct-3-ylmethylamine and the cis and trans isomers were separated but not assigned at the end of step b the less polar isomer being used in this example, $^1$H NMR (d$^6$-DMSO) δ 10.3 (1H, s), 8.7 (3H, m), 8.5 (1H, t), 8.2 (1H, m), 7.7 (1H, s), 7.5–7.2 (7H, m), 6.5 (1H, s), 4.8 (1H, m), 3.7–2.7 (5H, m), 1.5 and 1.4 (9H, m).

The compound was further characterised and tested as the di-N-methyl-D-glucamine salt. Found: C, 53.29; H, 7.02; N, 8.12. $C_{48}H_{68}N_6O_{18}$·3.1 H$_2$O requires C, 52.93; H, 7.03; N, 7.71%

EXAMPLE 110
5-(1S-(3,5-dicarboxyphenylaminocarbonyl)-2-phenylethylaminocarbonyl)-6-(4-hydroxycyclohexanemethylaminocarbonyl)-indole. Isomer 2 (unknown whether hydroxy group is cis or trans to the methylaminocarbonyl group)

This was prepared essentially as in example 109 except that the more polar isomer isolated in step b was used as substrate in step c instead of the less polar material. $^1$H NMR (d$^6$-DMSO) δ 10.2 (1H, s), 8.7 (3H, m), 8.5 (1H, t), 8.2 (1H, m), 7.7 (1H, s), 7.5 (1H, t), 7.4–7.2 (7H, m), 6.5 (1H, s), 4.8 (1H, m), 3.5–3.0 (5H, m), 1.7–1.0 (9H, m).

The compound was further characterised and tested as the di-N-methyl-D-glucamine salt. Found: C, 51.93; H, 6.87; N, 8.01. $C_{48}H_{68}N_6O_{18}$·4.8 H$_2$O requires C, 52.28 H, 7.08; N, 7.67%

EXAMPLE 111

5-(1S-(3,5-dicarboxyphenylaminocarbonyl)-2-phenylethylaminocarbonyl)-6-(1-adamantanemethylaminocarbonyl)-2-methylbenzimidazole a. 2-Methyl-benzimidazole-5,6-dicarboxylic acid anhydride This was prepared in several steps from 3,4-dimethoxycarbonylacetanilide by nitration with fuming nitric acid, followed by treatment with sulphuric acid to remove the acetyl group selectively. Catalytic hydrogenation, followed by treatment with hot acetic acid gave the benzimidazole skeleton. Saponification followed by anhydride formation by heating of the diacid gave the title compound.

b. 5-(1S-(3,5-dibenzyloxycarbonylphenylaminocarbonyl)-2-phenylethylaminocarbonyl)-2-methyl-benzimidazole-6-carboxylic acid This was prepared essentially as in example 108 step a except that the product of step a above was used as substrate instead of indole-5,6-dicarboxylic acid anhydride. The isolated filtrate was the pure carboxylic acid.

c. 5-(1S-(3,5-dibenzyloxycarbonylphenylaminocarbonyl)-2-phenylethylaminocarbonyl)-6-(1-adamantanemethylaminocarbonyl)-2-methylbenzimidazole This was prepared essentially as in example 108 step b except that the product of step b above was used as substrate instead of the product of example 108 step a.

d. 5-(1S-(3,5-dicarboxyphenylaminocarbonyl)-2-phenylethylaminocarbonyl)-6-(1-adamantanemethylaminocarbonyl)-2-methylbenzimidazole This was prepared essentially as in example 108 step c except that the product of step c above was used as substrate instead of the product of example 108 step b. $^1$H NMR (d$^6$-DMSO) δ 10.2 (1H, m), 8.8 (1H, d), 8.7 (2H, s), 8.5 (1H, t), 8.2 (1H, s), 7.8 (1H, br s), 7.4 (5H, m), 7.0 (1H, s), 4.8 (1H, m), 3.5 (1H, m), 3.0 (3H, m), 2.5 (3H, s), 1.8 (3H, s), 1.6 (6H, m), 1.4 (6H, s).

The compound was further characterised and tested as the di-N-methyl-D-glucamine salt. Found: C, 55.75; H, 7.05; N, 8.62. $C_{52}H_{73}N_7O_{17}$.3 $H_2O$ requires C, 55.65 H, 7.10; N, 8.74%

EXAMPLE 112

5-(1S-(3,5-dicarboxyphenylaminocarbonyl)-2-phenylethylaminocarbonyl)-4-(1-adamantanemethylaminocarbonyl)-benzimidazole. Regioisomer 1 (assignment of regioisomer uncertain)

a. Benzimidazole-4,5-dicarboxylic acid anhydride

This was prepared essentially as in example 111 step a except that 3,4-dimethoxycarbonyl-2-nitroaniline was used instead of 3,4-dimethoxycarbonyl-6-nitroaniline and formic acid was used instead of acetic acid in the course of formation of the second ring. 3,4-dimethoxycarbonyl-2-nitroaniline was isolated as a more minor product during the course of the hydrogenation described in example 111 step a.

b. 5-(1S-(3,5-dicarboxyphenylaminocarbonyl)-2-phenylethylaminocarbonyl)-4-(1-adamantanemethylaminocarbonyl)-benzimidazole This was prepared essentially as described in example 111 steps b to d except that benzimidazole-4,5-dicarboxylic acid anhydride was used in step b instead of benzimidazole-5,6-dicarboxylic acid anhydride. The two regioisomers formed during the course of these reactions were separated at the end of step c by column chromatography (silica 5% methanol and 95% dichloromethane) with the less polar regioisomer being taken through and designated as the compound of this example. $^1$H NMR (d$^6$-DMSO) δ 13.0 (1H, br s), 10.5 (2H, m), 8.6 (4H, m), 8.2 (1H, s), 7.9–7.1 (7H, m), 6.6 (1H, m), 4.8 (1H, m), 3.6–3.0 (4H, m), 1.9 (3H, s), 1.6 (12H, m).

The compound was further characterised and tested as the di-N-methyl-D-glucamine salt. Found: C, 55.29; H, 6.98; N, 8.93. $C_{51}H_{71}N_7O_{17}$.3 $H_2O$ requires C, 55.28 H, 7.00; N, 8.85%

EXAMPLE 113

4-(1S-(3,5-dicarboxyphenylaminocarbonyl)-2-phenylethylaminocarbonyl)-5-(1-adamantanemethylaminocarbonyl)-benzimidazole. Regioisomer 2 (assignment of regioisomer uncertain) The material was prepared essentially as in example 112 except that the more polar regioisomer isolated after chromatography was used in the final deprotection step, $^1$H NMR (d$^6$-DMSO) δ 13.0 (2H, br s), 10.7 and 9.5 (1H, 2×s), 8.6 (4H, m), 8.2 (1H, s), 7.7 (1H, br s), 7.4 (1H, m), 7.3 (6H, m), 4.8 (1H, m), 3.6 (1H, m), 3.0 (3H, m), 1.9 (3H, s), 1.6 (6H, m), 1.4 (6H, s).

The compound was further characterised and tested as the di-N-methyl-D-glucamine salt. Found: C, 56.22; H, 7.00; N, 9.03. $C_{51}H_{71}N_7O_{17}$.2 $H_2O$ requires C, 56.18 H, 6.93; N, 8.99%

EXAMPLE 114

5-(1S-(3,5-dicarboxyphenylaminocarbonyl)-2-phenylethylaminocarbonyl)-6-(1-adamantanemethylaminocarbonyl)-2-n-butylbenzimidazole This was prepared essentially as in example 111 except that n-pentanoic acid was used in step a instead of acetic acid, $^1$H NMR (d$^6$-DMSO) δ 13.0 (3H, m), 10.2 (1H, s), 8.8 (1H, d), 8.7 (2H, s), 8.5 (1H, t), 8.2 (1H, s), 7.8 (1H, br s), 7.3 (5H, m), 7.0 (1H, s), 4.8 (1H, m), 3.5–2.7 (6H, m), 1.8–1.3 (19H, m), 0.9 (3H, t).

The of and was further characterised and tested as the di-N-methyl-D-glucamine salt. Found: C, 57.39; H, 7.62; N, 8.59. $C_{55}H_{79}N_7O_{17}$.2 $H_2O$ requires C, 57.63 H, 7.30; N, 8.55%

EXAMPLE 115

2-(1S-(3,5-dicarboxyphenylaminocarbonyl)-2-phenylethylaminocarbonyl)-3-(1-adamantanemethylaminocarbonyl)-5-aminonaphthalene. Regioisomer 1 (regiochemistry unassigned)

This was prepared essentially as in example 24 steps g to i except that 5-nitronaphthalene-2,3-dicarboxylic acid anhydride was used as substrate instead of indole-5,6-dicarboxylic acid anhydride. The less polar regioisomer isolated at the penultimate stage was used to prepare the compound of this example. The final deprotection also served to reduce the nitro group, $^1$H NMR (d$^6$-DMSO) δ 13.5 (2H, br s), 10.2 (1H, s), 8.8 (1H, d), 8.7 (2H, d), 8.5 (1H, t), 8.2 (1H, d), 8.0–6.8 (10H, m), 5.7 (2H, br s), 4.8 (1H, m), 3.6–2.9 (4H, m), 1.9–1.5 (15H, m).

The compound was further characterised and tested as the di-N-methyl-D-glucamine salt. Found: C, 56.90; H, 7.14; N, 7.42. $C_{54}H_{74}N_7O_{17}$.3.3 $H_2O$ requires C, 56.94 H, 7.14; N, 7.38%

EXAMPLE 116

3-(1S-(3,5-dicarboxyphenylaminocarbonyl)-2-phenylethylaminocarbonyl)-2-(1-adamantanemethylaminocarbonyl)-5-aminonaphthalene. Regioisomer 2 (opposite regiochemistry to example 115)

This was prepared essentially as in example 115 except that the more polar regioisomer was taken through the final step $^1$H NMR (d$^6$-DMSO) δ 13.5 (2H, br s), 10.2 (1H, s), 8.9

(1H, d), 8.7 (2H, s), 8.4 (2H, m), 8.2–6.8 (10H, m), 5.9 (2H, br s), 4.8 (1H, m), 3.5–2.8 (4H, m), 1.8–1.5 (15H, m).

The compound was further characterised and tested as the di-N-methyl-D-glucamine salt. Found: C, 51.21; H, 7.26; N, 6.76. $C_{54}H_{74}N_7O_{17}.10\ H_2O$ requires C, 51.51 H, 7.52 N, 6.67%

EXAMPLE 117
5-(1S-(3,5-diaminocarbonylphenylaminocarbonyl)-2-phenylethylaminocarbonyl)-6-(1-adamantanemethylaminocarbonyl)-benzimidazole This was prepared essentially as in example 25 except that 1S-(3,5-diaminocarbonyl-phenylaminocarbonyl)-2-phenylethylamine was used in step d instead of 1S-(3,5-dibenzyloxycarbonylphenylaminocarbonyl)-2-phenylethyl amine and no final deprotection was required, Found: C, 54.67; H, 5.72; N, 12.58. $C_{37}H_{39}N_7O_5.2.2\ CH_2Cl_2.1.8$ DMF requires C, 54.65 H, 5.76 N, 12.78% $^1H$ NMR ($d^6$-DMSO) δ 12.8 (1H, br s), 10.2 (1H, s), 8.8 (1H, d), 8.5 (1H, t), 8.4 (2H, m), 8.1–7.9 (5H, m), 7.4–7.1 (8H, m), 4.8 (1H, m), 3.4 (2H, m), 2.9 (2H, m), 1.8 (3H, s), 1.4 (6H, m), 1.3 (6H, m).

EXAMPLE 118
5-(1S-(3,5-dihydroxyiminomethylenephenylaminocarbonyl)-2-phenylethylaminocarbonyl)-6-(1-adamantanemethylaminocarbonyl)-benzimidazole This was prepared essentially as in example 25 except that 1S-(3,5-diahydroxyiminomethylenephenylaminocarbonyl)-2-phenyl ethylamine was used in step d instead of 1S-(3,5-dibenzyloxycarbonylphenylaminocarbonyl)-2-phenylethyl amine and no final deprotection was required, Found: C, 63.18; H, 6.18; N, 14.01. $C_{37}H_{39}N_7O_5.2.3\ H_2O$ requires C, 63.25 H, 6.25 N, 13.95% $^1H$ NMR ($d^6$-DMSO) δ 12.8 (1H, br s), 11.3 (2H, s), 10.0 (1H, m), 8.8 (1H, d), 8.6 (1H, t), 8.4 (1H, s), 8.1 (4H, m), 7.9 (1H, m), 7.5 (1H, s), 7.3 (5H, m), 7.2 (1H, m), 4.8 (1H, m), 3.5 (1H, m), 3.1–2.8 (3H, m), 1.8 (3H, s), 1.5 (6H, m), 1.4 (6H, m).

EXAMPLE 119
5-(1S-(3,5-dihydroxymethylphenylaminocarbonyl)-2-phenylethylaminocarbonyl)-6-(1-adamantanemethylaminocarbonyl)-benzimidazole a. 5-(1S-(3,5-dihydroxymethylphenylaminocarbonyl)-2-phenylethylaminocarbonyl)-6-(1-adamantanemethylaminocarbonyl)-benzimidazole diacetoxy carbonate derivative.

This was prepared essentially as example 79 except that the diacetoxycarbonate derivative of 1S-(3,5-dihydroxymethylphenylaminocarbonyl)-2-phenylethylamine was used instead of 1S-(3-benzyloxycarbonylphenylaminocarbonyl)-2-phenylethylamine in step a.

b. 5-(1S-(3,5-dihydroxymethylphenylaminocarbonyl)-2-phenylethylaminocarbonyl)-6-(1-adamantanemethylaminocarbonyl)-benzimidazole The product of step a above (1.91 g, 2.5 mmol) was dissolved in methanol (210 ml) and was treated with a 1% solution of potassium carbonate in water (105 ml). After stirring overnight, the methanol was removed by evaporation and the resulting solid extracted with ethyl acetate. The organic layer was washed with brine, dried, filtered and evaporated to leave the title compound, Found: C, 69.69; H, 6.61; N, 11.19. $C_{37}H_{41}N_5O_8$ requires C, 69.90 H, 6.50 N, 11.02% $^1H$ NMR ($d^6$-DMSO) δ 12.8 (1H, br s), 9.8 (1H, s), 8.8 (1H, d), 8.5 (1H, t), 8.4 (1H, s), 7.9 (1H, m), 7.7 (2H, s), 7.3 (5H, m), 7.1 (1H, s), 7.0 (1H, s), 5.2 (2H, t), 4.7 (1H, m), 4.5 (4H, d), 3.3 (2H, m), 2.9 (2H, m), 1.9 (3H, s), 1.6 (6H, m), 1.5 (6H, m).

EXAMPLE 120
5-(1S-(3,5-hydrogencarbonylphenylaminocarbonyl)-2-phenylethylaminocarbonyl)-6-(1-adamantanemethylaminocarbonyl)-benzimidazole The compound of example 119 was oxidised by treatment with oxalyl chloride in DMSO and triethylamine using dichloromethane as solvent, following the Swern oxidation protocol in 45% yield, Found: C, 67.23; H, 6.08; N, 10.41. $C_{37}H_{37}N_5O_5$. 1.7 $H_2O$ requires C, 67.13 H, 6.15 N, 10.58% $^1H$ NMR ($d^6$-DMSO) δ 12.8 (1H, br s), 10.3 (1H, s), 10.1 (2H, s), 8.9 (1H, d), 8.7 (2H, s), 8.6 (1H, t), 8.4 (1H, s), 8.2 (1H, s), 7.8 (1H, s), 7.4 (5H, m), 7.1 (1H, s), 4.8 (1H, m), 3.3 (2H, m), 3.0 (2H, m), 2.0 (3H, s), 1.6 (6H, m), 1.4 (6H, m).

EXAMPLE 121
5-(1S-(3,5-di-t-butylcarbonyloxymethyloxycarbonyl phenylaminocarbonyl)-2-phenylethylaminocarbonyl)-6-(1-adamantanemethylaminocarbonyl)-benzofuran. Mixture of regioisomers at positions 5 and 6 a. 3,4-dimethoxycarbonyl-2-iodophenol

The dimethyl ester of 4-hydroxyphthallic acid (4.20 g, 20 mmol), was dissoved in triflic acid (15 g, 100 mmol), and cooled to 0° C. N-iodosuccinimide (4.5 g, 20 mmol) was added portionwise and stirred at room temperature for 2 h. The reaction mixture was poured onto a mixture of ice and water and the aqueous layer was extracted with dichloromethane (3×75 ml). The combined organic layers were washed succesively with 5% sodium bisulphite solution and brine before being dried, filtered and evaporated, to yield the title compound 4.51 g.

b. 5,6-Dimethoxycarbonyl-2-trimethylsilyl-benzofuran

The product of step a (4.5 g, 13.4 mmol) and TMS-acetylene (1.71 g, 17.4 mmol) in triethylamine (50 ml) and dioxan (80 ml) was degassed with argon for 15 min. Copper I iodide (152 mg, 0.8 mmol), was added followed by bis triphenylphosphine palladium dichloride. (564 mg, 0.8 mmol). The reaction was stirred at 60° C. overnight under an atmosphere of argon. The solvents were removed by evaporation and the resulting oil was redissolved in dichloromethane and washed sequentially with 10% citric acid solution and brine. The organic layer was dried, filtered and evaporated and passed through a short silica column to give the title compound.

c. Benzofuran-5,6-dicarboxylic acid anhydride

This was prepared from the product of step b in several steps by treatment with hydrogen fluoride/pyridine complex to remove the silicon group, followed by saponification to generate the diacid. Anhydride ring formation occurred on heating the diacid to approximately 100° C.

d. 6-(1-adamantanemethylaminocarbonyl)-benzofuran-5-carboxylic acid. Mixture of regioisomers at positions 5 and 6

This was prepared essentially as in example 24 step g except that benzofuran-5,6-dicarboxylic acid anhydride was used as substrate instead of indole-5,6-dicarboxylic acid anhydride.

e. 5-(1S-(3,5-di-t-butylcarbonyloxymethyloxycarbonyl-phenylaminocarbonyl)-2-phenylethylaminocarbonyl)-6-(1-adamantanemethylaminocarbonyl)-benzofuran. Mixture of regioisomers at positions 5 and 6

This was prepared essentially as in example 24 step h except that 6-(1-adamantanemethylaminocarbonyl)-benzofuran-5-carboxylic acid was used instead of 6-(1-adamantanemethylaminocarbonyl)-indole-5-carboxylic acid and 1S-(3,5-di-t-butylcarbonyloxymethyloxycarbonyl-phenylaminocarbonyl)-2-phenylethylamine was used instead of 1S-(3,5-di-benzyloxycarbonylphenylaminocarbonyl)-2- phenylethylamine. No attempt was made to separate the regioisomers at this point, $^1$H NMR (d$^6$-DMSO) δ 10.2 (1H, s), 9.0 (1H, d), 8.8 (2H, s), 8.6 (1H, t), 8.2 (2H, m), 7.9 (1H, 2×s), 7.3 (5H, m), 7.1 (2H, m), 6.0 (4H, s), 4.7 (1H, m), 3.4 (2H, m), 2.9 (2H, m), 1.4–1.3 (15H, m), 1.2 (18H, s).

EXAMPLE 122

5-(1S-(3,5-dicarboxyphenylaminocarbonyl)-2-phenylethylaminocarbonyl)-6-(1-adamantanemethylaminocarbonyl)-benzofuran. Mixture of regioisomers at positions 5 and 6 a. 5-(1S-(3,5-di-allyloxycarbonylphenylaminocarbonyl)-2-phenylethylaminocarbonyl)-6-(1-adamantanemethylaminocarbonyl)-benzofuran. Mixture of regioisomers at positions 5 and 6

This was prepared essentially as in example 121 except that 1S-(3,5-di-allyloxycarbonylphenylaminocarbonyl)-2-phenylethyl amine was used in step e instead of 1S-(3,5-di-t-butylcarbonyloxymethyloxycarbonylphenylaminocarbonyl)-2-phenylethylamine b. 5-(1S-(3,5-dibenzyloxycarbonylphenylaminocarbonyl)-2-phenylethylaminocarbonyl)-6-(1-adamantanemethylaminocarbonyl)-benzofuran The product of step a above was de-esterifeied by treatment with diethylamine in THF in the presence of palladium tetrakis triphenylphosphine. The product was initially isolated as the bis diethylamine salt, $^1$H NMR (d$^6$-DMSO) δ 10.2 (1H, s), 9.0 (1H, d), 8.8 (2H, s), 8.4 (3H$_1$, m), 8.1 (2H, m), 7.9 (1H, 2×s), 7.4–7.1 (6H, m), 7.0 (1H, m), 4.7 (1H, m), 3.4 (1H, m), 2.9 (3H, m), 1.8 (3H, s), 1.5 (6H, q), 1.3 (6H, s).

The compound was further characterised and tested as the di-N-methyl-D-glucamine salt. Found: C, 69.29; H, 6.05 N, 5.86. C$_{52}$H$_{71}$N$_5$O$_{18}$ requires C, 69.45; H, 5.97; N, 6.07%

EXAMPLE 123

5-(1S-(3,5-dicarboxyphenylaminocarbonyl)-2-phenylethylaminocarbonyl)-6-(1-adamantanemethylaminocarbonyl)-2,3-dihydro-benzofuran. Mixture of regioisomers at positions 5 and 6

This was prepared by hydrogenation of the dibenzyl ester of the compound of example 122 using 10% palladium on charcoal as catalyst. $^1$H NMR (d$^6$-DMSO) δ 10.1 (1H, 2×s), 8.8 and 8.7 (1H, m), 8.5 (2H, m), 8.2 (2H, m), 7.5–7.2 (6H, m), 6.9 (1H, m), 4.7 (1H, m), 4.6 (2H, m), 3.4 (2H, m), 3.0 (4H, m), 1.8 (3H, s), 1.5 (6H, m), 1.4 (6H, s).

The compound was further characterised and tested as the di-N-methyl-D-glucamine salt. Found: C, 55.84; H, 6.99; N, 6.61. C$_{52}$H$_{73}$N$_5$O$_{18}$.3.0 H$_2$O requires C, 56.16; H, 7.18; N, 6.30%

EXAMPLE 124

5-(1S-(3,5-dimethoxycarbonylphenylaminocarbonyl)-2-phenylethylaminocarbonyl)-6-(1-adamantanemethylaminocarbonyl)-benzofuran This was prepared by treatment of the compound of example 121 with ammonia in methanol, $^1$H NMR (d$^6$-DMSO) δ 10.2 (1H, m), 8.9 (1H, m), 8.8 (2H, s), 8.2 (2H, m), 8.0 (1H, s), 7.9 (1H, 2×s), 7.4–7.0 (7H, m), 4.7 (1H, m), 3.9 (6H, s), 3.4–2.9 (4H, m), 1.9 (3H, s), 1.5 (6H, q), 1.4 (6H, s).

EXAMPLE 125

5-(1S-(3,5-dicarboxyphenylaminocarbonyl)-2-phenylethylaminocarbonyl)-6-(1-adamantanemethylaminocarbonyl)-benzothiophene. Mixture of regioisomers at positions 5 and 6 a. Benzothiophene-5,6-dicarboxylic acid anhydride

This was prepared in several steps starting from 3-methyl-2-carboxy-thiophene. Esterification and allylic bromination gave a material which on treatment with the sodium salt of 4-toluenesulphonic acid gave 3-toluenesulphonylmethyl-2-methoxycarbonyl-thiophene. The methyl ester was reduced with superhydride and the resulting alcohol oxidised to the aldehyde using PDC. Cycloaddition with dimethyl fumarate using potassium t-butoxide as base gave benzothiophene-5,6-dicarboxylic acid. This was converted to the title compound by treatment with acetic anhydride.

b. 5-(1S-(3,5-di-t-butyloxycarbonylphenylaminocarbonyl)-2-phenylethylaminocarbonyl)-6-(1-adamantanemethylaminocarbonyl)-benzothiophene.

This was prepared essentially as in example 121 steps d and e except that benzothiophene-5,6-dicarboxylic acid anhydride was used in step d instead of benzofuran-5,6-dicarboxylic acid anhydride and 1S-(3,5-di-t-butyloxycarbonylphenylaminocarbonyl)-2-phenylethylamine was used in step e instead of 1S-(3,5-di-t-butylcarbonyloxymethyloxycarbonylphenylaminocarbonyl)-2-phenylethylamine.

c. 5-(1S-(3,5-dicarboxyphenylaminocarbonyl)-2-phenylethylaminocarbonyl)-6-(1-adamantanemethylaminocarbonyl)-benzothiophene The product of step b was treated with trifluoroacetic acid for 2 h. The volatile material was removed by evaporation and the residue azeotroped several times with diethyl ether to leave the title compound, $^1$H NMR (d$^6$-DMSO) δ 13.2 (2H, br s), 10.2 (1H, s), 8.9 (1H, m), 8.7 (2H, m), 8.4 (1H, m), 8.3 (2H, m), 8.2 (2H, m), 8.0 (1H, m), 7.5–7.0 (5H, m), 4.8 (1H, m), 3.3–2.9 (4H, m), 1.8 (3H, s), 1.6 (6H, q), 1.4 (6H, s).

The compound was further characterised and tested as the di-N-methyl-D-glucamine salt

EXAMPLE 126

(±)-6-(1S-(3,5-dicarboxyphenylaminocarbonyl)-2-phenylethylaminocarbonyl)-5-(1-adamantanemethylaminocarbonyl)-4,5,6,7-tetrahydro-5-aza-benzimidazole.

a. (±)-N-1,5-di-t-Butyloxycarbonyl-6-carboxy-4,5,6,7-tetrahydro-5-aza-benzimidazole This was prepared by treatment of D/L-histidine with aqueous formaldehyde using standard Pictet-Spengler conditions. The product was treated with BOC anhydride to give the title compound.

b (±)-N-1,5-di-t-Butyloxycarbonyl-6-(1S-(3,5-dibenzyloxycarbonylphenylaminocarbonyl)-2-phenylethylaminocarbonyl)-4,5,6,7-tetrahydro-5-aza-benzimidazole This was prepared by treatment of the product of step a with one equivalent of 1S-(3,5-dibenzyloxycarbonylphenylaminocarbonyl)-2-phenylethylamine and 1.2 equivalents of DCCI. The product was isolated by filtration, evaporation and column chromatography (silica, ethyl acetate: DCM 1:2).

c (±)-6-(1S-(3,5-dibenzyloxycarbonylphenylaminocarbonyl)-2-phenylethylaminocarbonyl)-5-(1-adamantanemethylaminocarbonyl)-4,5,6,7-tetrahydro-5-aza-benzimidazole This was prepared by treating the product of step b with TFA and then with one equivalent of 1-adamantanemethylisocyanate in the presence of DMAP. After stirring overnight the reaction mixture was evaporated to dryness and the residue chromatographed (silica, acetone-:toluene 1:2). The most polar product was the title compound.

d. (±)-6-(1S-(3,5-dicarboxyphenylaminocarbonyl)-2-phenylethylaminocarbonyl)-5-(1-adamantanemethylaminocarbonyl)-4,5,6,7-tetrahydro-5-aza-benzimidazole.

This was prepared essentially as in example 24 step i except that the dibenzyl ester prepared above was used as substrate instead of the product of example 24 step h, $^1$H NMR (d$^6$-DMSO) δ 10.3 (1H, m), 8.4 (2H, m), 8.2 (1H, s), 8.0–7.7 (1H, m), 7.4 (1H, m), 7.2 (6H, m), 6.5 (1H, m), 5.1 (1H, m), 4.5 (1H, m), 4.2 (1H, m), 3.3–2.8 (6H, m), 1.8 (3H, m), 1.6 (6H, q), 1.4 (6H, m).

The compound was further characterised and tested as the di-N-methyl-D-glucamine salt. Found: C, 53.86; H, 7.40; N, 9.53. $C_{50}H_{74}N_8O_{17}$.3.5 H$_2$O requires C, 53.91 H, 7.28; N, 9.98%

EXAMPLE 127

5-(1S-(2-chloro-5-carboxyphenylaminocarbonyl)-2-phenylethylaminocarbonyl)-6-(1-adamantanemethylaminocarbonyl)-benzimidazole This was prepared essentially as in example 25 except that 1S-(2-chloro-5-benzyloxycarbonylphenylaminocarbonyl)-2-phenyl ethylamine was used in step d instead of 1S-(3,5-dibenzyloxycarbonylphenylaminocarbonyl)-2-phenylethylamine. 1S-(2-chloro-5-benzyloxycarbonylphenylaminocarbonyl)-2-phenyl ethylamine was prepared by coupling BOC-L-phenylalanine with 2-chloro-5-benzyloxycarbonylaniline using PyBrOP, followed by treatment with trifluoroacetic acid, $^1$H NMR (d$^6$-DMSO) δ 13.2 (1H, br s), 12.8 (1H, br s), 10.0 (1H, s), 8.9 (1H, d). 8.4 (2H, s), 8.2 (1H, s), 8.0–7.6 (3H, m), 7.4–7.1 (6H, m), 4.8 (1H, m), 3.4 (1H, m), 2.9 (3H, m), 1.8 (3H, s), 1.6 (6H, q), 1.4 (6H, s).

The compound was further characterised and tested as the N-methyl-D-glucamine salt. Found: C, 58.33; H, 6.49; N, .9.09. $C_{43}H_{53}ClN_6O_{10}$.2.3 H$_2$O requires C, 58.01 H, 6.51; N, 9.44%

EXAMPLE 128

5-(1S-(3-trifluoroacetylaminosulphonylphenylaminocarbonyl)-2-phenylethylaminocarbonyl)-6-(1-adamantanemethylaminocarbonyl)-benzimidazole This was prepared essentially as in example 99 except that the product of example 25 step c was used in step b instead of the product of example 24 step g, Found: C, 55.01; H, 5.27; N, 10.33. $C_{37}H_{37}F_3N_6O_6S$.2.3 H$_2$O requires C, 58.01 H, 6.51; N, 9.44% $^1$H NMR (d$^6$-DMSO) δ 10.1 (1H, s), 8.9 (1H, d), 8.5 (5H, m), 8.0–7.0 (10H, m), 4.8 (1H, m), 3.6–2.9 (4H, m), 1.9 (3H, s), 1.6 (6H, m), 1.5 (6H, m).

EXAMPLE 129

5-(3S-(3,5-dicarboxyphenylaminocarbonyl)-1,2,3,4-tetrahydroisoquinolino-2-carbonyl)-6-(1-adamantanemethylaminocarbonyl)-benzimidazole This was prepared essentially as in example 79 except that 3S-(3,5-dibenzyloxyphenylaminocarbonyl)-1,2,3,4-tetrahydroisoquinoline was used as substrate instead of 1S-(3-benzyloxycarbonylphenyl-aminocarbonyl)-2-phenylethylamine in step a. The 3S-(3,5-dibenzyloxyphenylaminocarbonyl)-1,2,3,4-tetrahydroisoquinoline was prepared by coupling BOC-3S-carboxy-1,2,3,4-tetrahydroisoquinoline and 3,5-dibenzyloxycarbonylaniline in the presence of PyBROP, followed by treatment with trifluoroacetic acid, $^1$H NMR (d$^6$-DMSO) δ 13.0 (3H, br s), 11.5 and 10.0 (1H, 2×s), 9.0–7.0 (11H, m), 5.4 (1H, m), 4.8–4.2 (2H, m), 3.5–2.8 (4H, m), 1.9 (3H, m), 1.5 (6H, m), 1.4 (6H, m).

The compound was further characterised and tested as the di-5 N-methyl-D-glucamine salt. Found: C, 55.51; H, 6.89 N, 8.80. $C_{52}H_{71}N_7O_{17}$.3.2 H$_2$O requires C, 55.58 H, 6.94; N, 8.73%

EXAMPLE 130

5-(1S-(3,5-dicarboxyphenylaminocarbonyl)-2-phenylethylaminocarbonyl)-6-(2-naphthalenemethylaminocarbonyl)-benzimidazole This was prepared essentially as in example 79 except that 1S-(3,5-di-benzyloxycarbonylphenylaminocarbonyl)-2-phenylethylamine was used in step a instead of 1S-(3-benzyloxycarbonylphenylaminocarbonyl)-2-phenylethylamine and 2-naphthalenemethylamine was used in step b instead of 1-adamantanemethylamine, $^1$H NMR (d$^6$-DMSO) δ 12.9 (1H, br s), 10.1 (1H, s), 9.3 (1H, t), 8.9 (1H, d), 8.7 (2H, s), 8.4 (2H, s), 8.1 (1H, s), 8.0 (1H, m), 7.7 (4H, m), 7.4 (8H, m), 4.8 (3H, m), 3.0 (2H, m).

The compound was further characterised and tested as the di-N-methyl-D-glucamine salt. Found: C, 54.92; H, 6.35 N, 8.95. $C_{51}H_{63}N_7O_{17}$.3.7 H$_2$O requires C, 55.06 H, 6.38; N, 8.81%

EXAMPLE 131

5-(1S-(3,5-dicarboxyphenylaminocarbonyl)-2-(3-fluorophenyl)ethylaminocarbonyl)-6-(1-adamantanemethylaminocarbonyl)-benzimidazole This was prepared essentially as in example 79 except that 1S-(3,5-di-benzyloxycarbonylphenylaminocarbonyl)-2-(3-fluorophenyl)ethylamine was used in step a instead of 1S-(3-benzyloxycarbonylphenylaminocarbonyl)-2-phenylethylamine. The 1S-(3,5-dibenzyloxycarbonylphenylaminocarbonyl)-2-(3-fluorophenyl)ethylamine was prepared by coupling BOC-L-3-fluorophenylalanine and 3,5-dibenzyloxycarbonylaniline in the presence of PyBROP, followed by treatment with trifluoroacetic acid, $^1$H NMR (d$^6$-DMSO) δ 13.0 (3H, br s), 10.2 (1H, s), 8.9 (1H, d), 8.7 (2H, s), 8.5 (1H, t), 8.4 (1H, s), 8.2 (1H, s), 7.9 (1H, s), 7.4 (1H, m), 7.2 (4H, m), 4.8 (1H, m), 3.6–2.9 (4H, m), 1.8 (3H, s), 1.7 (6H, q), 1.5 (6H, s).

The compound was further characterised and tested as the di-N-methyl-D-glucamine salt

EXAMPLE 132

5-(1S-(3,5-dicarboxyphenylaminocarbonyl)-2-(4-fluorophenyl)ethylaminocarbonyl)-6-(1-adamantanemethylaminocarbonyl)-benzimidazole This was prepared essentially as in example 79 except that 1S-(3,5-di-benzyloxycarbonylphenylaminocarbonyl)-2-(4-fluorophenyl)ethylamine was used in step a instead of 1S-(3-benzyloxycarbonylphenylaminocarbonyl)-2-phenylethylamine.

The 1S-(3,5-di-benzyloxycarbonylphenylaminocarbonyl)-2-(4-fluorophenyl)ethylamine was prepared by coupling BOC-L-4-fluorophenylalanine and 3,5-dibenzyloxycarbonylaniline in the presence of PyBROP, followed by treatment with trifluoroacetic acid, $^1$H NMR (d$^6$-DMSO) δ 13.0 (3H, br s), 10.2 (1H, s), 8.9 (1H, d), 8.7 (2H, s), 8.5 (1H, t), 8.4 (1H, s), 8.2 (1H, s), 7.9 (1H, s), 7.4 (2H, m), 7.2 (3H, m), 4.8 (1H, m), 3.6–2.9 (4H, m), 1.8 (3H, s), 1.7 (6H, q), 1.5 (6H, s).

The compound was further characterised and tested as the di-N-methyl-D-glucamine salt

EXAMPLE 133
5-(1S-(3,5-dicarboxyphenylaminocarbonyl)-2-(2-trifluoromethylphenyl)ethylaminocarbonyl)-6-(1-adamantanemethylaminocarbonyl)-benzimidazole This was prepared essentially as in example 79 except that 1S-(3,5-di-benzyloxycarbonylphenylaminocarbonyl)-2-(2-trifluoromethylphenyl)ethylamine was used in step a instead of 1S-(3-benzyloxycarbonylphenylaminocarbonyl)-2-phenylethylamine. The 1S-(3,5-di-benzyloxycarbonylphenylaminocarbonyl)- 2-(2-trifluoromethylphenyl)-ethylamine was prepared by coupling BOC-L-2-trifluoromethylphenylalanine and 3,5-dibenzyloxycarbonylaniline in the presence of PyBROP, followed by treatment with trifluoroacetic acid, $^1$H NMR (d$^6$-DMSO) δ 13.0 (3H, br s), 10.2 (1H, s), 9.0 (1H, d), 8.7 (2H, s), 8.6 (1H, t), 8.4 (1H, s), 8.2 (1H, s), 7.9 (1H, s), 7.7 (4H, m), 7.2 (1H, m), 4.9 (1H, m), 3.8–3.0 (4H, m), 1.8 (3H, s), 1.6 (6H, q), 1.5 (6H, s).

The compound was further characterised and tested as the di-N-methyl-D-glucamine salt Found: C, 52.67; H, 6.57; N, 8.25. $C_{52}H_{70}F_3N_7O_{17}$.3.5 H$_2$O requires C, 52.70 H, 6.55; N, 8.27%

EXAMPLE 134
5-(1S-(3,5-dicarboxyphenylaminocarbonyl)-2-(4-iodophenyl)ethylaminocarbonyl)-6-(1-adamantanemethylaminocarbonyl)-benzimidazole 5-(1S-(3,5-di-allyloxyphenylaminocarbonyl)-2-(4-iodophenyl)ethylaminocarbonyl)-6-(1-adamantanemethylaminocarbonyl)-benzimidazole This was prepared essentially as in example 79 steps a and b except that 1S-(3,5-di-allyloxycarbonylphenylaminocarbonyl)-2-(4-iodophenyl)ethylamine was used in step a instead of 1S-(3-benzyloxycarbonylphenylaminocarbonyl)-2-phenylethylamine. The 1S-(3,5-di-allyloxycarbonylphenylaminocarbonyl)-2-(4-iodophenyl)ethylamine was prepared by coupling BOC-L-4-iodophenylalanine and 3,5-diallyloxycarbonylaniline in the presence of PyBROP, followed by treatment with trifluoroacetic acid.

b 5-(1S-(3,5-dicarboxyphenylaminocarbonyl)-2-(4-iodophenyl)ethylaminocarbonyl)-6-(1-adamantanemethylaminocarbonyl)-benzimidazole This was prepared essentially as in example 122 step b but using the product of step a above as substrate instead of 5-(1S-(3,5-di-allyloxycarbonylphenylaminocarbonyl)-2-phenylethylaminocarbonyl)-6-(1-adamantanemethylaminocarbonyl)-benzofuran. The compound was isolated and characterised as a bis dietylamine salt $^1$H NMR (d$^6$-DMSO) δ 10.1 (1H, s), 8.8 (1H, d), 8.4 (4H, s), 8.2 (1H, s), 7.9 (1H, s), 7.7 (2H, m), 7.3 (1H, m), 7.2 (2H, m), 4.7 (1H, m), 3.5–2.9 (4H, m), 1.8 (3H, s), 1.7 (6H, q), 1.5 (6H, s).

EXAMPLE 135
5-(1S-(3,5-dicarboxyphenylaminocarbonyl)-2-(2-chlorophenyl) ethylaminocarbonyl)-6-(1-adamantanemethylaminocarbonyl)-benzimidazole This was prepared essentially as in example 134 except that 1S-(3,5-di-allyloxycarbonylphenylaminocarbonyl)-2-(2-chlorophenyl)ethylamine instead of 1S-(3,5-di-allyloxycarbonylphenylaminocarbonyl)-2-(4-iodophenyl)ethylamine in step a. The 1S-(3,5-di-allyloxycarbonylphenylaminocarbonyl)-2-(2-chlorophenyl)ethylamine was prepared by coupling BOC-L-2-chlorophenylalanine and 3,5-diallyloxycarbonylaniline in the presence of PyBROP, followed by treatment with trifluoroacetic acid. The title compound was isolated and characterised as a bis dietylamine salt. Found: C, 62.21; H, 7.05; N, 11.22. $C_{45}H_{58}ClN_7O_7$.1.5 H$_2$O requires C, 62.02 H, 7.06; N, 11.25% $^1$H NMR (d$^6$-DMSO) δ 10.1 (1H, s), 8.8 (1H, d), 8.5 (3H, s), 8.4 (1H, s), 8.2 (1H, s), 7.9 (1H, s), 7.5–7.2 (7H, m), 4.8 (1H, m), 3.6–2.9 (4H, m), 1.8 (3H, s), 1.6 (6H, q), 1.5 (6H, s).

EXAMPLE 136
(±)-5-(1-(3,5-dicarboxyphenylaminocarbonyl)-2-pentafluorophenylethylaminocarbonyl)-6-(1-adamantanemethylaminocarbonyl)-benzimidazole This was prepared essentially as in example 79 except that (±)-1-(3,5-dibenzyloxycarbonylphenylaminocarbonyl)-2-pentafluorophenylethylamine was used in step a instead of 1S-(3-benzyloxycarbonylphenylaminocarbonyl)-2-phenylethylamine. (±)-1-(3,5-dibenzyloxycarbonylphenylaminocarbonyl)-2-pentafluorophenylethylamine was prepared by coupling BOC-pentafluorophenylalanine with 3,5-dibenzyloxycarbonylaniline using PyBrOP, followed by treatment with trifluoroacetic acid, $^1$H NMR (d$^6$-DMSO) δ 13.0 (2H, br s), 10.2 (1H, s), 8.9 (1H, d), 8.6 (2H, d), 8.5 (1H, t), 8.4 (1H, s), 8.2 (1H, d), 7.9 (1H, s), 7.4 (1H, s), 4.8 (1H, m), 3.5 (1H, dd), 3.2 (1H, dd), 3.0 (2H, d), 1.9 (3H, s), 1.5 (6H, q), 1.4 (6H, s).

The compound was further characterised and tested as the di-N-methyl-D-glucamine salt. Found: C, 50.83; H, 6.04; N, 8.17. $C_{51}H_{66}F_5N_7O_{17}$.3.3H$_2$O requires C, 50.87; H, 6.08; N, 8.14%

EXAMPLE 137
5-(1S-(3-acetylaminosulphonylphenylaminocarbonyl)-2-phenylethylaminocarbonyl)-6-(1-adamantanemethylaminocarbonyl)-benzimidazole a 1S-(3-acetylaminosulphonylphenylaminocarbonyl)-2-phenylethylamine This was prepared as in example 99 step a except that acetic anhydride was used to acylate the sulphonamide instead of trifluoroacetic anhydride.

b. 5-(1S-(3-acetylaminosulphonylphenylaminocarbonyl)-2-phenylethylaminocarbonyl)-6-(1-adamantanemethylaminocarbonyl)-benzimidazole This was prepared essentially as in example 128 except that the product of step a above was used as substrate instead of 1S-(3-trifluoroacetylaminosulphonylphenylaminocarbonyl)-2-phenylethylamine in step b, $^1$H NMR (d$^6$-DMSO) δ 12.1 (1H, br s), 10.2 (1H, s), 8.9 (1H, d), 8.6 (3H, m), 8.0–7.2 (10H, m), 4.8 (1H, m), 3.6–2.9 (4H, m), 1.9 (6H, m), 1.6 (6H, m), 1.5 (6H, m).

EXAMPLE 138
5-(1S-(3-acetylaminosulphonylphenylamino carbonyl)-2-phenylethylaminocarbonyl)-6-(1-adamantanemethylaminocarbonyl)-indole. Mixture of regioisomers at positions 5 and 6

This was prepared essentially as in example 99 except that 1S-(3-acetylaminosulphonylphenylaminocarbonyl)-2-phenylethylamine was used in step b instead of 1S-(3-trifluoroacetylaminosulphonylphenylaminocarbonyl)-2-phenylethylamine, $^1$H NMR (d$^6$-DMSO) δ 12.1 (1H, br s), 11.5 (1H, s), 10.3 (1H, 2×s), 8.8 (1H, 2×d), 8.7–7.2 (13H, m), 6.6 and 6.5 (1H, m), 4.8 (1H, m), 3.6–2.8 (4H, m), 1.9 (6H, m), 1.6 (6H, m), 1.5 (6H, m).

EXAMPLE 139

5-(1S-(3-benzoylaminosulphonylphenylaminocarbonyl)-2-phenylethylaminocarbonyl)-6-(1-adamantanemethylaminocarbonyl)-benzimidazole This was prepared essentially as in example 137 except that benzoyl chloride was used as acylating agent during the course of step a instead of acetic anhydride, $^1$H NMR (d$^6$-DMSO) δ 12.8 (1H, br s), 10.1 (1H, s), 8.8 (1H, d), 8.5 (3H, m), 8.3–7.2 (16H, m), 4.8 (1H, m), 3.6–2.9 (4H, m), 1.9 (3H, m), 1.6 (6H, m), 1.5 (6H, m).

EXAMPLE 140

5-(1S-(2-methoxy-5-carboxyphenylaminocarbonyl)-2-phenylethylaminocarbonyl)-6-(1-adamantanemethylaminocarbonyl)-benzimidazole This was prepared essentially as in example 79 except that 1S-(2-methoxy-5-benzyloxycarbonylphenylaminocarbonyl)-2-phenylethylamine was used in step a instead of 1S-(3-benzyloxycarbonylphenylaminocarbonyl)-2-phenylethylamine. The 1S-(2-methoxy-5-benzyloxycarbonylphenylaminocarbonyl)-2-phenylethylamine was prepared by coupling BOC-L-phenyl-alanine and 2-methoxy-5-benzyloxycarbonylaniline in the presence of PyBROP, followed by treatment with trifluoroacetic acid, $^1$H NMR (d$^6$-DMSO) δ 12.7 (2H, br s), 9.4 (1H, s), 8.8 (1H, d), 8.5 (1H, s), 8.4 (1H, s), 8.2 (1H, t), 7.7 (2H, m), 7.3 (7H, m), 4.8 (1H, m), 3.9 (3H, s), 3.4–2.8 (4H, m), 1.9 (3H, s), 1.6 (6H, q), 1.4 (6H, s).

The compound was further characterised and tested as the N-methyl-D-glucamine salt. Found: C, 59.15; H, 7.00; N, 9.41. C$_{44}$H$_{56}$N$_6$O$_{11}$.2.75 H$_2$O requires C, 59.08 H, 6.93; N, 9.40%

EXAMPLE 141

5-(1S-(3,5-dicarboxyphenylaminocarbonyl)-2-phenylethylaminocarbonyl)-6-(2-naphthalenenemethylaminocarbonyl)-indole. Mixture of regioisomers at positions 5 and 6

This compound was prepared essentially as in example 130 except that indole-5,6-dicarboxylic acid anhydride was used in step a instead of benzimidazole-5,6-dicarboxylic acid anhydride $^1$H NMR (d$^6$-DMSO) δ 11.6 (1H, br s), 10.2 (1H, s), 9.3 (1H, t), 8.8 (1H, d), 8.7 (2H, s), 8.4 (2H, s), 8.1 (1H, s), 7.8 (4H, m), 7.6–7.2 (11H, m), 6.5 (1H, s), 4.8 (3H, m), 3.5 (1H, dd), 3.0 (1H, dd).

The compound was further characterised and tested as the di-N-methyl-D-glucamine salt

EXAMPLE 142

(±)-5-(1-(3,5-dicarboxyphenylaminocarbonyl)-2-(2,6-difluorophenyl)ethylaminocarbonyl)-6-(1-adamantanemethylaminocarbonyl)-benzimidazole This was prepared essentially as in example 79 except that (±)-1-(3,5-dibenzyloxycarbonylphenylaminocarbonyl)-2-(2,6-difluorophenyl)ethylamine was used in step a instead of 1S-(3-benzyloxycarbonylphenylaminocarbonyl)-2-phenylethylamine. (±)-1-(3,5-dibenzyloxycarbonylphenylaminocarbonyl)-2-(2,6-difluorophenyl)ethylamine was prepared by coupling BOC-2,6-difluorophenylalanine with 3,5-dibenzyloxycarbonylaniline using PyBrOP, followed by treatment with trifluoroacetic acid, $^1$H NMR (d$^6$-DMSO) δ 13.3 (2H, br s), 12.9 (1H, br s), 10.2 (1H, s), 8.9 (1H, d), 8.7 (2H, d), 8.6 (1H, t), 8.4 (1H, s), 8.2 (1H, d), 7.9 (1H, m), 7.4 (1H, m), 7.3 (1H, m), 7.1 (2H, m), 4.8 (1H, m), 3.5 (1H, dd), 3.1 (1H, dd), 2.9 (2H, d), 1.9 (3H, s), 1.6 (6H, m), 1.5 (6H, s)

The compound was further characterised and tested as the di-N-methyl-D-glucamine salt

EXAMPLE 143

5-(1R-(3,5-dicarboxyphenylaminocarbonyl)-2-(2-fluorophenyl)ethylaminocarbonyl)-6-(1-adamantanemethylaminocarbonyl)-benzimidazole This was prepared essentially as in example 79 except that 1R-(3,5-di-benzyloxycarbonylphenylaminocarbonyl)-2-(2-fluorophenyl)ethylamine was used in step a instead of 1S-(3-benzyloxycarbonylphenylaminocarbonyl)-2-phenylethylamine.

The 1R-(3,5-di-benzyloxycarbonylphenylaminocarbonyl)-2-(2-fluorophenyl)ethylamine was prepared by coupling BOC-D-2-fluorophenylalanine and 3,5-dibenzyloxycarbonylaniline in the presence of PyBROP, followed by treatment with trifluoroacetic acid, $^1$H NMR (d$^6$-DMSO) δ 13.0 (3H, br s), 10.2 (1H, s), 8.9 (1H, d), 8.7 (2H, s), 8.6 (1H, t), 8.4 (1H, s), 8.2 (1H, s), 7.9 (1H, d), 7.4–7.2 (4H, m), 7.1 (1H, s), 4.8 (1H, m), 3.6–2.9 (4H, m), 1.8 (3H, s), 1.6 (6H, m), 1.3 (6H, m).

The compound was further characterised and tested as the di-N-methyl-D-glucamine salt

EXAMPLE 144

5-(1S-(3,5-dicarboxyphenylaminocarbonyl)-2-(2,4-difluorophenyl) ethylaminocarbonyl)-6-(1-adamantanemethylaminocarbonyl)-benzimidazole This was prepared essentially as in example 79 except that 1S-(3,5-dibenzyloxycarbonylphenylaminocarbonyl)-2-(2,4-difluorophenyl)ethylamine was used in step a instead of 1S-(3-benzyloxycarbonylphenylaminocarbonyl)-2-phenylethylamine. 1S-(3,5-dibenzyloxycarbonylphenylaminocarbonyl)-2-(2,4-difluorophenyl)ethylamine was prepared by coupling BOC-L-2,4-difluorophenylaianine with 3,5-dibenzyloxycarbonylaniline using PyBrOP, followed by treatment with trifluoroacetic acid, $^1$H NMR (d$^6$-DMSO) δ 13.2 (3H, br s), 10.2 (1H, s), 8.9 (1H, d), 8.7 (2H, d), .8.6 (1H, t), 8.4 (1H, s), 8.2 (1H, t), 7.5 (1H, m), 7.3 (2H, m), 7.2 (1H, s), 7.1 (1H, m), 4.8 (1H, m), 3.5 (1H, dd), 3.0 (3H, m), 1.9 (3H, s), 1.6 (6H, q), 1.5 (6H, s).

The compound was further characterised and tested as the di-N-methyl-D-glucamine salt

EXAMPLE 145

5-(1R-(3,5-dicarboxyphenylaminocarbonyl)-2-(2,4-difluorophenyl)ethylaminocarbonyl)-6-(1-adamantanemethylaminocarbonyl)-benzimidazole This was prepared essentially as in example 79 except that 1R-(3,5-dibenzyloxycarbonylphenylaminocarbonyl)-2-(2,4-difluorophenyl)ethylamine was used in step a instead of 1S-(3-benzyloxycarbonylphenylaminocarbonyl)-2-phenylethylamine. 1R-(3,5-dibenzyloxycarbonylphenylaminocarbonyl)-2-(2,4-difluorophenyl)ethylamine was prepared by coupling BOC-D-2,4-difluorophenylalanine with 3,5-dibenzyloxycarbonylaniline using PyBrOP, followed by treatment with trifluoroacetic acid, $^1$H NMR (d$^6$-DMSO) δ 13.2 (3H, br s), 10.2 (1H, s), 8.9 (1H, d), 8.7 (2H, d), 8.6 (1H, t), 8.4 (1H, s), 8.2 (1H; t), 7.5 (1H, m), 7.3 (2H, m), 7.2 (1H, s), 7.1 (1H, m), 4.8 (1H, m), 3.5 (1H, dd), 3.0 (3H, m), 1.9 (3H, s), 1.6 (6H, q), 1.5 (6H, s).

The compound was further characterised and tested as the di-N-methyl-D-glucamine salt

EXAMPLE 146

5-(1S-(3,5-dicarboxyphenylaminocarbonyl)-2-(2,6-difluorophenyl)ethylaminocarbonyl)-6-(1-adamantanemethylaminocarbonyl)-benzimidazole This was prepared essentially as in example 79 except that 1S-(3,5-dibenzyloxycarbonylphenylaminocarbonyl)-2-(2,6-difluorophenyl)ethylamine was used in step a instead of 1S-(3-benzyloxycarbonylphenylaminocarbonyl)-2-phenylethylamine. 1S-(3,5-dibenzyloxycarbonylphenylaminocarbonyl)-2-(2,6-difluorophenyl)ethylamine was prepared by coupling BOC-L-2,6-difluorophenylalanine with 3,5-dibenzyloxycarbonylaniline using PyBrOP, followed by treatment with trifluoroacetic acid, $^1$H NMR (d$^6$-DMSO) δ 13.3 (2H, br s), 12.9 (1H, br s), 10.2 (1H, s), 8.9 (1H, d), 8.7 (2H, d), 8.6 (1H, t), 8.4 (1H, s), 8.2 (1H, d), 7.9 (1H, m), 7.4 (1H, m), 7.3 (1H, m), 7.1 (2H, m), 4.8 (1H, m), 3.5 (1H, dd), 3.1 (1H, dd), 2.9 (2H, d), 1.9 (3H, s), 1.6 (6H, m), 1.5 (6H, s).

The compound was further characterised and tested as the di-N-methyl-D-glucamine salt

EXAMPLE 147

5-(1R-(3,5-dicarboxyphenylaminocarbonyl)-2-(2,6-difluorophenyl)ethylaminocarbonyl)-6-(1-adamantanemethylaminocarbonyl)-benzimidazole This was prepared essentially as in example 79 except that 1R-(3,5-dibenzyloxycarbonylphenylaminocarbonyl)-2-(2,6-difluorophenyl)ethylamine was used in step a instead of 1S-(3-benzyloxycarbonylphenylaminocarbonyl)-2-phenylethylamine. 1R-(3,5-dibenzyloxycarbonylphenylaminocarbonyl)-2-(2,6-difluorophenyl)ethylamine was prepared by coupling BOC-D-2,6-difluorophenylalanine with 3,5-dibenzyloxycarbonylaniline using PyBrOP, followed by treatment with trifluoroacetic acid, $^1$H NMR (d$^6$-DMSO) δ 13.3 (2H, br s), 12.9 (1H, br s), 10.2 (1H, s), 8.9 (1H, d), 8.7 (2H, d), 8.6 (1H, t), 8.4 (1H, s), 8.2 (1H, d), 7.9 (1H, m), 7.4 (1H, m), 7.3 (1H, m), 7.1 (2H, m), 4.8 (1H, m), 3.5 (1H, dd), 3.1 (1H, dd), 2.9 (2H, d), 1.9 (3H, s), 1.6 (6H, m), 1.5 (6H, s).

The compound was further characterised and tested as the di-N-methyl-D-glucamine salt

EXAMPLE 148

5-(1S-(3,5-dicarboxyphenylaminocarbonyl)-2-pentafluorophenylethylaminocarbonyl)-6-(1-adamantanemethylaminocarbonyl)-benzimidazole This was prepared essentially as in example 79 except that 1S-(3,5-dibenzyloxycarbonylphenylaminocarbonyl)-2-pentafluorophenylethylamine was used in step a instead of 1S-(3-benzyloxycarbonylphenylaminocarbonyl)-2-phenylethylamine. 1S-(3,5-dibenzyloxycarbonylphenylaminocarbonyl)-2-pentafluorophenylethylamine was prepared by coupling BOC-L-pentafluorophenylalanine with 3,5-dibenzyloxycarbonylaniline using PyBrOP, followed by treatment with trifluoroacetic acid, $^1$H NMR (d$^6$-DMSO) δ 13.0 (2H, br s), 10.2 (1H, s), 8.9 (1H, d), 8.6 (2H, d), 8.5 (1H, t), 8.4 (1H, s), 8.2 (1H, d), 7.9 (1H, s), 7.4 (1H, s), 4.8 (1H, m), 3.5 (1H, dd), 3.2 (1H, dd), 3.0 (2H, d), 1.9 (3H, s), 1.5 (6H, q), 1.4 (6H, The compound was further characterised and tested as the di-N-methyl-D-glucamine salt

EXAMPLE 149

5-(1R-(3,5-dicarboxyphenylaminocarbonyl)-2-pentafluorophenylethylaminocarbonyl)-6-(1-adamantanemethylaminocarbonyl)-benzimidazole This was prepared essentially as in example 79 except that 1R-(3,5-dibenzyloxycarbonylphenylaminocarbonyl)-2-pentafluorophenylethylamine was used in step a instead of 1S-(3-benzyloxycarbonylphenylaminocarbonyl)-2-phenylethylamine. 1R-(3,5-dibenzyloxycarbonylphenylaminocarbonyl)-2-pentafluorophenylethylamine was prepared by coupling BOC-pentafluorophenylalanine with 3,5-dibenzyloxycarbonylaniline using PyBrOP, followed by treatment with trifluoroacetic acid, $^1$H NMR (d$^6$-DMSO) δ 13.0 (2H, br s), 10.2 (1H, s), 8.9 (1H, d), 8.6 (2H, d), 8.5 (1H, t), 8.4 (1H, s), 8.2 (1H, d), 7.9 (1H, s), 7.4 (1H, s), 4.8 (1H, m), 3.5 (1H, dd), 3.2 (1H, dd), 3.0 (2H, d), 1.9 (3H, s), 1.5 (6H, q), 1.4 (6H, s).

The compound was further characterised and tested as the di-N-methyl-D-glucamine salt

EXAMPLE 150

5-(1R-(3,5-dicarboxyphenylaminocarbonyl)-2-(3-fluorophenyl)ethylaminocarbonyl)-6-(1-adamantanemethylaminocarbonyl)-benzimidazole This was prepared essentially as in example 79 except that 1R-(3,5-di-benzyloxycarbonylphenylaminocarbonyl)-2-(3-fluorophenyl)ethylamine was used in step a instead of 1S-(3-benzyloxycarbonylphenylaminocarbonyl)-2-phenylethylamine. The 1R-(3,5-di-benzyloxycarbonylphenylaminocarbonyl)-2-(3-fluorophenyl)ethylamine was prepared by coupling BOC-D-3-fluorophenylalanine and 3,5-dibenzyloxycarbonylaniline in the presence of PyBROP, followed by treatment with trifluoroacetic acid, $^1$H NMR (d$^6$-DMSO) δ 13.0 (3H, br s), 10.2 (1H, s), 8.9 (1H, d), 8.7 (2H, s), 8.5 (1H, t), 8.4 (1H, s), 8.2 (1H, s), 7.9 (1H, s), 7.4 (1H, m), 7.2 (4H, m), 4.8 (1H, m), 3.6–2.9 (4H, m), 1.8 (3H, s), 1.7 (6H, q), 1.5 (6H, s).

The compound was further characterised and tested as the di-N-methyl-D-glucamine salt The compounds of the examples were tested for binding at the CCKO receptor in mouse cortical membranes by means of a radioligand binding assay. The procedure was as follows:

The whole brains from male mice (CD1 22–25 g; Charles River) were removed and placed in ice-cold buffer (pH7.2@21±3°) of the following composition (mM); 10 HEPES, 130 NaCl, 4.7 KCl, 5 MgCl$_2$, 1 EDTA and containing 0.25 g.l$^{-1}$ bacitracin The cortex was dissected, weighed and homogenised in 40 ml ice-cold buffer using a Teflon-in-glass homogeniser. The homogenate was centrifuged at 39,800 g for 20 min at 4°, the supernatant discarded and the pellet resuspended by homogenisation in fresh buffer. The homogenate was recentrifuged (39,800 g; 20 min@4°) and the final pellet was resuspended in HEPES buffer to give a tissue concentration of 2 mg.ml$^{-1}$ (original wet weight).

The membranes (400 ml) were incubated for 150 min at 21±3° in a final volume of 0.5 ml with HEPES buffer containing [$^{125}$I]-CCK8S (0.05 ml; 200 pM NEN 2200 Ci.mmol$^{-1}$) and competing compound. Total and non-specific binding of [$^{125}$I]-CCK8S were defined using 0.05 ml of buffer and 0.05 ml of 10 mM L-365,260, respectively. The assay was terminated by rapid filtration through presoaked Whatman GF/B filters using a Brandell Cell harvester. The filters were washed (3×3 ml) with ice-cold 50 mM Tris-HCl (pH7.4@4° C.) and bound radioactivity determined by counting (1 min.) in a gamma-counter.

The results obtained from the CCK$_B$ assays are set out in Table 1.

TABLE 1

| Example | CCK$_8$ pK$_i$ | Example | CCK$_8$ pK$_i$ |
|---|---|---|---|
| 1 | 5.5 | 73 | 6.3 |
| 2 | 5.5 | 74 | 7.6 |
| 3 | 6.4 | 75 | 7.8 |
| 4 | 5.5 | 76 | 6.2 |
| 5 | 6.0 | 77 | 6.6 |
| 6 | 6.0 | 78 | 7.3 |
| 7 | 5.8 | 79 | 7.7 |
| 8 | 5.3 | 80 | 8.4 |
| 9 | 6.6 | 81 | 6.1 |
| 10 | 5.8 | 82 | 7.0 |
| 11 | 5.9 | 83 | 7.8 |
| 12 | 5.9 | 84 | 8.6 |
| 13 | 5.7 | 85 | 8.3 |
| 14 | 6.0 | 86 | 7.5 |
| 15 | 7.9 | 87 | 9.1 |
| 16 | 5.6 | 88 | 8.3 |
| 19 | 5.7 | 89 | 6.2 |
| 20 | 5.0 | 90 | 8.2 |
| 22 | 5.9 | 91 | 7.4 |
| 24 | 8.9 | 92 | 6.5 |
| 26 | 7.9 | 93 | 8.1 |
| 27 | 8.5 | 94 | 6.7 |
| 28 | 8.5 | 95 | 5.9 |
| 29 | 8.1 | 96 | 6.3 |
| 30 | 7.6 | 97 | 9.1 |
| 31 | 7.9 | 98 | 8.4 |
| 32 | 8.4 | 99 | 8.4 |
| 33 | 5.6 | 100 | 7.9 |
| 34 | 8.1 | 101 | 7.4 |
| 35 | 7.2 | 102 | 7.4 |
| 36 | 9.4 | 103 | 7.0 |
| 37 | 8.4 | 104 | 8.9 |
| 38 | 7.5 | 105 | 8.3 |
| 39 | 6.4 | 106 | 5.7 |
| 40 | 6.8 | 108 | 5.9 |
| 41 | 7.8 | 109 | 6.7 |
| 42 | 7.8 | 110 | 6.4 |
| 43 | 5.8 | 111 | 5.8 |
| 44 | 8.7 | 112 | 8.1 |
| 45 | 7.1 | 113 | 6.9 |
| 46 | 6.7 | 114 | 6.0 |
| 47 | 6.8 | 115 | 7.6 |
| 48 | 6.2 | 116 | 8.5 |
| 49 | 5.6 | 117 | 6.1 |
| 50 | 6.6 | 118 | 6.7 |
| 51 | 8.0 | 119 | 6.2 |
| 52 | 7.2 | 120 | 6.2 |
| 53 | 8.1 | 122 | 8.3 |
| 54 | 8.1 | 123 | 7.9 |
| 55 | 8.2 | 124 | 6.5 |
| 56 | 7.0 | 125 | 8.9 |
| 57 | 7.7 | 126 | 6.3 |
| 58 | 6.5 | 127 | 7.6 |
| 59 | 6.9 | 128 | 8.2 |
| 60 | 7.8 | 129 | 6.7 |
| 61 | 8.4 | 130 | 7.6 |
| 62 | 7.8 | 131 | 8.4 |
| 63 | 8.4 | 132 | 8.4 |
| 64 | 7.2 | 134 | 7.6 |
| 65 | 7.3 | 135 | 8.3 |
| 66 | 5.8 | 136 | 8.9 |
| 67 | 6.3 | 137 | 7.7 |
| 68 | 5.9 | 138 | 8.1 |
| 69 | 6.5 | 139 | 7.8 |
| 70 | 8.1 | | |
| 71 | 6.4 | | |
| 72 | 6.0 | | |

The compounds of the examples were also tested for gastrin antagonist activity in an immature rat stomach assay. The procedure was as follows:

The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing $3 \times 10^{-8}$M 5-methylfurmethide, maintained at 37° and gassed vigorously with 95% $O_2$/5% $CO_2$. The stomach was continuously perfused at a rate of 1 ml min$^{-1}$ with unbuffered solution gassed with 100% $O_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et.al., Br. J. Pharmacol., 1985, 86, 581.

The results obtained from the gastrin assays are set out in Table 2.

TABLE 2

| Example | Gastrin pK$_B$ | Example | Gastrin pK$_B$ |
|---|---|---|---|
| 1 | 5.8 | 80 | 8.2 |
| 2 | 6.0 | 81 | 6.9 |
| 3 | 6.7 | 82 | 6.9 |
| 4 | 6.3 | 83 | 7.2 |
| 5 | 6.8 | 85 | 8.9 |
| 7 | 6.4 | 86 | 7.7 |
| 8 | 5.9 | 87 | 9.6 |
| 9 | 6.3 | 88 | 8.6 |
| 10 | 6.5 | 89 | 6.8 |
| 11 | 6.6 | 90 | 8.0 |
| 12 | 5.9 | 91 | 8.0 |
| 13 | 6.4 | 92 | 6.8 |
| 14 | 6.5 | 93 | 7.7 |
| 15 | 8.2 | 95 | 5.9 |
| 16 | 6.2 | 100 | 7.5 |
| 21 | 5.3 | 103 | 7.8 |
| 23 | 7.4 | 104 | 8.6 |
| 24 | 9.5 | 105 | 8.5 |
| 26 | 9.3 | 108 | 6.1 |
| 27 | 9.2 | 109 | 6.9 |
| 28 | 9.7 | 110 | 6.9 |
| 29 | 9.2 | 112 | 8.2 |
| 30 | 9.1 | 113 | 7.2 |
| 31 | 8.9 | 115 | 8.2 |
| 32 | 9.1 | 116 | 9.0 |
| 33 | 7.7 | 118 | 6.7 |
| 34 | 8.7 | 122 | 9.1 |
| 35 | 8.7 | 123 | 8.5 |
| 37 | 8.4 | 124 | 6.8 |
| 38 | 7.1 | 125 | 9.4 |
| 39 | 6.8 | 126 | 7.0 |
| 40 | 7.3 | 127 | 7.5 |
| 41 | 7.8 | 128 | 8.6 |
| 42 | 9.3 | 131 | 9.7 |
| 44 | 8.7 | 132 | 9.0 |
| 46 | 7.1 | 133 | 8.1 |
| 47 | 8.3 | 134 | 8.8 |
| 48 | 7.0 | 135 | 8.9 |
| 50 | 6.9 | 136 | 9.5 |
| 51 | 7.6 | 137 | 7.8 |
| 53 | 7.9 | 139 | 7.1 |
| 54 | 8.1 | | |
| 55 | 8.3 | | |
| 56 | 7.1 | | |
| 57 | 7.7 | | |
| 58 | 7.5 | | |
| 59 | 7.5 | | |
| 60 | 8.1 | | |
| 61 | 8.7 | | |
| 62 | 8.2 | | |
| 63 | 9.1 | | |
| 65 | 8.2 | | |

TABLE 2-continued

| Example | Gastrin pK$_B$ |
|---|---|
| 67 | 6.8 |
| 69 | 7.1 |
| 70 | 7.8 |
| 71 | 7.0 |
| 72 | 6.3 |
| 73 | 7.2 |
| 74 | 9.0 |
| 75 | 7.7 |
| 76 | 6.9 |
| 77 | 7.0 |
| 78 | 8.6 |
| 79 | 7.0 |

The compounds of the examples were also tested in a CCK$_A$ binding assay as follows:

The pancreatata were removed from male guinea-pigs (200–300 g; Dunkin Hartley) and placed in ice-cold HEPES buffer (pH 7.2@21±3°). The pancreatata were homogenised in 40 ml ice-cold HEPES buffer using a polytron (Brinkmann, PT10, setting 10) 4×1 second. The homogenate was centrifuged at 39,800 g for 15 min at 4°. The supernatant was discarded and the pellet re-suspended using a Teflon-in-glass homogeniser in 20 volumes of fresh buffer and re-centrifuged as above.

The final pellet was re-suspended using a Teflon-in-glass homogeniser to a tissue concentration of 1 mg.ml$^{-1}$ (original wet weight), and filtered through 500 μm pore-size Nytex mesh.

The membranes (400 μl; containing 0.375 μM PD134, 308) are incubated for 150 minutes at 21±3° in a final volume of 0.5 ml with HEPES buffer containing [$^{125}$I]-CCK$_8$(S) (50 μl; 200 pM) and competing compound. Total and non-specific binding of [$^{125}$I]-CCK$_8$(S) are defined using 50 μl of buffer and 50 μl of 100 nM L-364, 718 respectively. The assay is terminated by rapid filtration through pre-soaked Whatman GF/B filters using a Brandell Cell Harvester. The filters were washed (3×3 ml) with ice-cold 50 mM Tris HCl (pH 7.4 at 4°) and bound radioactivity is determined by counting (1 min) in a gamma counter.

The results are set out in Table 3.

TABLE 3

| Example | CCK$_A$ pK$_i$ | Example | CCK$_A$ pK$_i$ |
|---|---|---|---|
| 1 | 5.1 | 82 | 5.7 |
| 2 | 4.9 | 83 | 6.4 |
| 3 | 5.5 | 84 | 6.2 |
| 4 | 5.4 | 85 | 5.5 |
| 5 | 5.2 | 86 | 5.0 |
| 6 | 5.6 | 87 | 5.5 |
| 7 | 5.8 | 88 | 5.6 |
| 8 | 6.0 | 89 | 5.1 |
| 15 | 6.1 | 90 | 5.3 |
| 16 | 5.5 | 91 | 5.3 |
| 17 | 4.8 | 92 | 4.9 |
| 18 | 6.3 | 93 | 5.6 |
| 19 | 5.3 | 94 | 5.0 |
| 20 | 5.0 | 95 | 5.8 |
| 21 | 5.2 | 96 | 5.7 |
| 22 | 5.4 | 97 | 6.3 |
| 24 | 5.7 | 98 | 6.7 |
| 26 | 5.5 | 99 | 5.4 |
| 27 | 5.6 | 100 | 6.4 |
| 28 | 5.4 | 101 | 6.6 |
| 29 | 5.4 | 102 | 5.9 |
| 30 | 5.2 | 103 | 5.2 |
| 31 | 5.5 | 104 | 6.5 |
| 33 | 5.2 | 105 | 6.8 |
| 34 | 6.1 | 108 | <5.0 |
| 36 | 5.5 | 109 | <5.0 |
| 37 | 5.6 | 110 | <5.0 |
| 39 | 4.9 | 111 | <5.0 |
| 40 | 6.3 | 112 | <5.0 |
| 41 | 5.7 | 113 | 5.2 |
| 42 | 5.5 | 114 | 5.5 |
| 44 | 5.6 | 115 | 5.6 |
| 45 | 6.1 | 116 | 5.6 |
| 46 | 5.1 | 117 | 5.8 |
| 47 | 5.2 | 118 | 6.3 |
| 48 | 5.5 | 119 | 5.6 |
| 49 | 5.6 | 120 | 6.0 |
| 50 | 6.1 | 121 | 5.1 |
| 52 | 5.9 | 122 | 5.4 |
| 53 | 6.1 | 123 | 6.3 |
| 54 | 5.9 | 124 | 5.7 |
| 55 | 5.8 | 125 | 5.7 |
| 57 | 5.7 | 126 | 5.3 |
| 58 | 5.0 | 127 | 5.9 |
| 59 | 5.1 | 128 | 5.7 |
| 60 | 5.6 | 129 | 5.1 |
| 61 | 5.2 | 130 | 5.4 |
| 62 | 5.4 | 131 | 5.3 |
| 66 | 5.0 | 132 | 5.4 |
| 67 | 5.7 | 133 | 5.1 |
| 68 | 5.9 | 134 | 6.1 |
| 69 | 5.1 | 135 | 5.1 |
| 70 | 5.1 | 136 | <5.0 |
| 71 | 5.3 | | |
| 72 | 5.6 | | |
| 73 | 5.2 | | |
| 74 | 5.3 | | |
| 75 | 6.1 | | |
| 76 | <5.0 | | |
| 77 | <5.0 | | |
| 78 | 5.3 | | |
| 79 | 6.0 | | |
| 80 | 6.1 | | |
| 81 | 5.5 | | |

We claim:
1. A compound of the formula

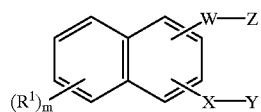

wherein
W and X replace hydrogen on adjacent carbon atoms of the naphthalene moiety,
m is from 0 to 6, provided that m is not more than 2 unless R$^1$ is exclusively halo,
each R$^1$ is independently selected from the group consisting of halo, amino, amidino, nitro, cyano, hydroxy, sulphamoyl, hydroxysulphonyl, carboxy, esterified carboxy, amidated carboxy, tetrazolyl, C$_1$ to C$_8$ alkyl, aryl, substituted aryl, C$_1$ to C$_6$ hydroxyalkyl, C$_1$ to C$_6$ haloalkyl, C$_1$ to C$_6$ alkoxy, C$_1$ to C$_6$ alkylcarboxyamino, HON=C—, R$^{27}$—SO$_2$—NH—, R$^{27}$—SO$_2$—NH—CO—, R$^{27}$—CO—, R$^{27}$—CO—NH—, R$^{27}$—CO—NH—SO$_2$—, R$^{27}$—CO—NH—SO— and R$^{28}$—NH—SO$_2$—,
wherein R$^{27}$ is H, C$_1$ to C$_6$ alkyl, C$_1$ to C$_6$ haloalkyl, aryl and substituted aryl, and R$^{28}$ is H, C$_1$ to C$_6$ alkyl, C$_1$ to C$_6$ haloalkyl, aryl, substituted aryl, —OH or —CN, except that R$^{27}$ cannot be H when attached to a sulphur atom, W is a carbonyl, sulphonyl or sulphinyl group, and X is a carbonyl, sulphonyl or sulphinyl group, provided that at least one of W and X contains carbonyl, Y is $R^3$—N ($R^4$)— or $R^{3A}$—O—, wherein $R^3$ is H or $C_1$ to $C_{15}$ hydrocarbyl, optionally substituted by halogen, wherein up to two CH groups of the hydrocarbyl moiety optionally may be replaced by a nitrogen atom, and wherein up to two $CH_2$ groups of the hydrocarbyl moiety may be replaced by an oxygen or sulphur atom, $R^{3A}$ is $C_6$ to $C_{15}$ hydrocarbyl, optionally substituted by halogen, wherein up to two carbon atoms of the hydrocarbyl moiety optionally may be replaced by a nitrogen, oxygen or sulphur atom, and $R^4$ is H, $C_1$ to $C_3$ alkyl, carboxymethyl or esterified carboxymethyl, provided that Y does not contain a —O—O— group, and Z is selected from i) 

—O—$R^5$ wherein $R^5$ is H, $C_1$ to $C_5$ alkyl, phenyl, substituted phenyl, benzyl or substituted benzyl;

ii) 

—N(Q)—H wherein Q is H, $C_1$ to $C_5$ hydrocarbyl, or —$R^6$—U, wherein $R^6$ is a bond or $C_1$ to $C_5$ alkylene and U is aryl, substituted aryl, heterocyclic, substituted heterocyclic or cycloalkyl, iii)

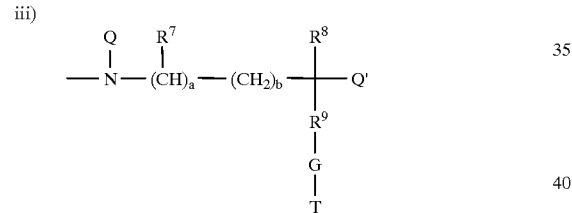

wherein a is 0 or 1 and b is from 0 to 3, $R^7$ is H or methyl, $R^8$ is H or methyl; or $R^8$ is $CH_2$= and Q' is absent; or $R^7$ and $R^8$ are linked to form a 3- to 7-membered ring, $R^9$ is a bond or $C_1$ to $C_5$ hydrocarbylene, G is a bond, —CHOH— or —C(O)—, Q' is as recited above for Q, or Q' is —$R^6$—(C(O))$_d$—L—(C(O))$_e$—$R^5$ wherein $R^5$ and $R^6$ are as defined above, L is O, S or —N($R^{10}$)—, wherein $R^{10}$ is as defined above for $R^4$, and d and e are 0 or 1, provided that d+e<2;

or Q' and $R^8$, together with the carbon atom to which they are attached, form a 3- to 7-membered ring, Q is as defined above;

or Q and $R^8$ together form a group of the formula —(CH$_2$)$_f$—V—(CH$_2$)$_g$— wherein V is —S—, —S(O)—, —S(O)$_2$—, —CH$_2$—, —CHOH— or —C(O)—, f is from 0 to 2 and g is from 0 to 3;

or, when Q' is —$R^6$—U and U is an aromatic group, Q may additionally represent a methylene link to U, which link is ortho to the $R^6$ link to U, T is H, cyano, $C_1$ to $C_4$ alkyl, —CH$_2$OH, carboxy, esterified carboxy, amidated carboxy or tetrazolyl; and iv) 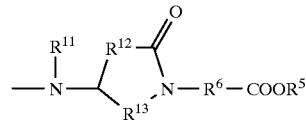

wherein $R^5$ and $R^6$ are as defined above, $R^{11}$ is as defined above for $R^4$, and $R^{12}$ and $R^{13}$ are independently a bond or $C_1$ to $C_3$ alkylene, provided that $R^{12}$ and $R^{13}$ together provide from 2 to 4 carbon atoms in the ring, wherein said heterocyclic groups are selected from the group consisting of benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzafuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl, and wherein said substituted aryl, benzyl, phenyl or heterocyclic groups independently are substituted with up to 3 substituents, independently selected from the group consisting of halo, amino, amidino, nitro, cyano, hydroxy, sulphamoyl, hydroxysulphonyl, carboxy, esterified carboxy, amidated carboxy, tetrazolyl, $C_1$ to $C_8$ alkyl, $C_1$ to $C_6$ hydroxyalkyl, $C_1$ to $C_6$ haloalkyl, $C_1$ to $C_6$ alkoxy, $C_1$ to $C_6$ alkylcarboxyamino, HON=C—, $R^{27}$—SO$_2$—NH—, $R^{27}$—SO$_2$—NH—CO—, $R^{27}$—CO—, $R^{27}$—CO—NH—, $R^{27}$—CO—NH—SO$_2$—, $R^{27}$—CO—NH—SO— and $R^{28}$—NH—SO$_2$—, or a pharmaceutically acceptable salt thereof.

2. A compound according to claim 1 wherein $R^3$ is $C_6$ to $C_8$ straight or branched chain alkyl, or $R^{23}$—(CH$_2$)$_p$—, wherein $R^{23}$ is selected from phenyl, 1-naphthyl, 2-naphthyl, indolyl, norbornyl, adamantyl, cyclohexyl and cycloheptyl, and p is from 0 to 3.

3. A compound according to claim 1 wherein W is carbonyl and X is sulphonyl.

4. A compound according to claim 1 wherein W is carbonyl and X is carbonyl.

5. A compound according to claim 1 wherein W is sulphonyl and X is carbonyl.

6. A compound according to claim 1 wherein m is 0.

7. A compound according to claim 1 wherein

—X—Y is —CONR$^3$R$^4_1$, and

—W—Z is

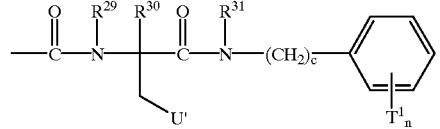

wherein $R^{29}$, $R^{30}$ and $R^{31}$ independently are H or $C_1$ to $C_3$ alkyl;

U' is an aromatic group;

n is 1 or 2;

T' is —CO$_2$H, tetrazolyl, esterified carboxy, amidated carboxy, R$^{27}$—SO$_2$—NH—, R$^{27}$—SO$_2$—NH—CO—, R$^{27}$—CO—, R$^{27}$—CO—NH—, R$^{27}$—CO—NH—SO$_2$—, R$^{27}$—CO—NH—SO— or R$^{28}$—NH—SO$_2$—, each T' being independently selected from the foregoing when n is 2; and c is from 0 to 2.

8. A pharmaceutical composition comprising a compound according to claim 1, together with a pharmaceutically acceptable diluent or carrier.

9. A method of making a compound according to claim 1 wherein W is carbonyl, said method comprising the step of reacting a compound of the formula YH, with a compound of the formula

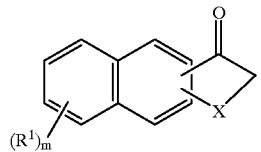

10. A method of making a compound according to claim 1 wherein W is sulphonyl, said method comprising the step of reacting a compound of the formula R$^3$—Hal with a compound of the formula

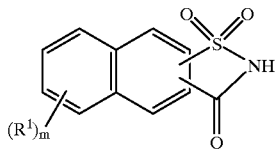

wherein Hal represents a halogen atom, and then reacting the product with an alkoxide.

11. A method of making a compound according to claim 1 wherein W or X is sulphoxide, said method comprising the step of reacting a compound of the formula R$^3$—Hal with a compound of the formula:

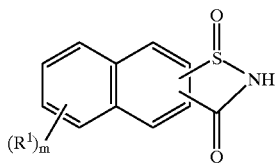

wherein Hal represents a halogen atom, and then reacting the product with an alkoxide.

* * * * *